United States Patent
Dai et al.

(10) Patent No.: US 11,279,695 B2
(45) Date of Patent: Mar. 22, 2022

(54) ANDROGRAPHOLIDE COMPOUND AND METHOD FOR TREATMENT OR PREVENTION OF FIBROTIC DISEASE USING THE SAME

(71) Applicant: Zhengzhou University, Zhengzhou (CN)

(72) Inventors: Guifu Dai, Zhengzhou (CN); Di Wu, Zhengzhou (CN); Haiwei Xu, Zhengzhou (CN); Jiazhen Zhu, Zhengzhou (CN); Zibo Fu, Zhengzhou (CN); Zhenzhen Guan, Zhengzhou (CN); Xiaopei Zhang, Zhengzhou (CN); Ning Shang, Zhengzhou (CN); Shuqiu Zhang, Zhengzhou (CN); Guangming Yan, Zhengzhou (CN)

(73) Assignee: ZHENGZHOU UNIVERSITY, Zhengzhou (CN)

( * ) Notice: Subject to any disclaimer, the term of this patent is extended or adjusted under 35 U.S.C. 154(b) by 65 days.

(21) Appl. No.: 17/009,821

(22) Filed: Sep. 2, 2020

(65) Prior Publication Data
US 2021/0047307 A1    Feb. 18, 2021

Related U.S. Application Data

(63) Continuation-in-part of application No. PCT/CN2019/076608, filed on Mar. 1, 2019.

(30) Foreign Application Priority Data

Mar. 2, 2018 (CN) .......................... 201810174787.1
Mar. 2, 2018 (CN) .......................... 201810174797.5

(51) Int. Cl.
| | | |
|---|---|---|
| C07D 407/04 | (2006.01) | |
| C07D 307/58 | (2006.01) | |
| A61P 1/16 | (2006.01) | |
| A61P 13/12 | (2006.01) | |
| A61P 11/00 | (2006.01) | |

(52) U.S. Cl.
CPC .............. *C07D 407/04* (2013.01); *A61P 1/16* (2018.01); *A61P 11/00* (2018.01); *A61P 13/12* (2018.01); *C07D 307/58* (2013.01)

(58) Field of Classification Search
CPC ....... C07D 407/04; C07D 307/58; A61P 1/16; A61P 13/12; A61P 11/00
See application file for complete search history.

(56) References Cited

U.S. PATENT DOCUMENTS 10,064,841 B1 * 9/2018 Al-Dhabi ............. A61K 31/365

* cited by examiner

*Primary Examiner* — Timothy R Rozof
(74) *Attorney, Agent, or Firm* — Matthias Scholl P.C.; Matthias Scholl

(57) ABSTRACT

A compound represented by formula I or II. $R_1$ and $R_2$ are at each occurrence selected from the group consisting of hydrogen, methyl, phenyl, 2-methoxyphenyl, 3-methoxyphenyl, 4-methoxyphenyl, 3,4,5-trimethoxyphenyl, 2-hydroxyphenyl, 3-hydroxyphenyl, 4-hydroxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromobenzene group, 3-fluoro-4-bromophenyl, 3-chloro-4-bromophenyl, 2,3,4-trichlorophenyl, 2-methoxy-4-chlorophenyl, 2-hydroxy-4-chlorophenyl, 2-hydroxy-4-methoxyphenyl, 3-fluoro-4-(4-methylpiperazinyl)phenyl, 4-(N,N-dimethylamino)phenyl, and 3-fluoro-4-(4-morpholinyl)phenyl. $R_3$ and $R_4$ are hydrogen, or $R_3$ and $R_4$ are at each occurrence selected from the group consisting of —$CH_2CH_2COOH$, —$CH_2CH_2CH_2CH_2COOH$, —$CH_2CH=CHCH_2COOH$, and —$CH_2CH_2CH_2CH_2CH_2CH_2COOH$; or $R_3$ and $R_4$ are —$COR_5$, and $R_5$ is selected from the group consisting of 3-pyridyl, —$CH_2CH_2COOH$, —$CH_2CH_2CH_2CH_2COOH$, —$CH_2CH=CHCH_2COOH$, and —$CH_2CH_2CH_2CH_2CH_2CH_2CH_2COOH$.

13 Claims, 20 Drawing Sheets

ANDROGRAPHOLIDE COMPOUND AND METHOD FOR TREATMENT OR PREVENTION OF FIBROTIC DISEASE USING THE SAME

CROSS-REFERENCE TO RELATED APPLICATIONS

This application is a continuation-in-part of International Patent Application No. PCT/CN2019/076608 with an international filing date of Mar. 1, 2019, designating the United States, now pending, and further claims foreign priority benefits to Chinese Patent Application No. 201810174787.1 filed Mar. 2, 2018, and to Chinese Patent Application No. 201810174797.5 filed Mar. 2, 2018. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to 14-deoxy-11,12-didehydro-8,12-epoxyandrographolide, 14-deoxy-11,12-didehydro-7,8-eneandrographolide, and 15-substituted derivatives thereof. Also, the disclosure relates to the use of andrographolide derivatives in the treatment of a variety of fibrotic diseases.

SUMMARY

The disclosure provides a compound of 14-deoxy-11,12-didehydro-8,12-epoxyandrographolide (ADY):

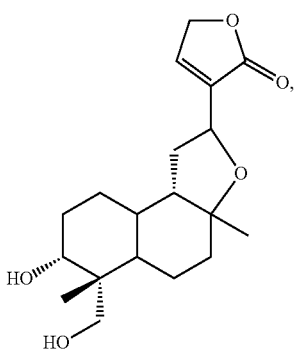

ADY and a 15-substituted derivative of ADY as shown in the following formula I:

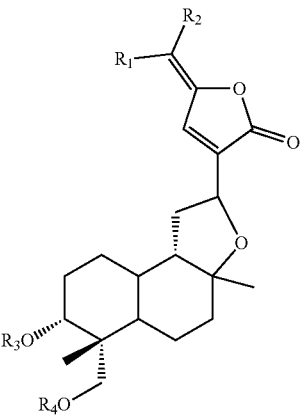

I where $R_1$ and $R_2$ are at each occurrence selected from the group consisting of hydrogen, methyl, substituted or unsubstituted aromatic ring, or substituted or unsubstituted heteroaromatic ring; and the aromatic ring and heteroaromatic ring include, but are not limited to, the following: phenyl, pyridyl, furyl, thienyl, and pyrrolyl. The substituted groups mentioned herein can be substituted with one or more substituents which may be the same or different. Optionally, $R_1$ and $R_2$ are at each occurrence selected from a cyclic amino comprising a $C_{3-6}$-cycloalkyl or a $C_{2-5}$-alkyl and a nitrogen atom, such as cyclopentyl and cyclohexyl. $R_1$ and $R_2$ are the same or different substituents. $R_3$ and $R_4$ are at each occurrence selected from hydrogen, —$COR_5$, —$CH_2CH_2COOH$, —$CH_2CH_2CH_2CH_2COOH$, —$CH_2CH=CHCH_2COOH$, and —$CH_2CH_2CH_2CH_2CH_2CH_2COOH$, where $R_5$ is selected from the group consisting of substituted or unsubstituted aromatic heterocyclic group, carbon ring, heterocyclic structure, and saturated or unsaturated $C_{1-18}$ carbon chain; and the aromatic heterocyclic group includes, but is not limited to, the following: phenyl, pyridyl, pyrrolyl, and furyl; and the carbon ring and the heterocyclic structure include, but are not limited to, the following: cyclohexyl, cyclopentyl, cyclopropyl, morpholinyl, and piperidinyl. $R_3$ and $R_4$ are the same or different substituent groups.

In a class of this embodiment, $R_1$ and $R_2$ are at each occurrence selected from the group consisting of hydrogen, methyl, phenyl, 2-methoxyphenyl, 3-methoxyphenyl, 4-methoxyphenyl, 3,4,5-trimethoxyphenyl, 2-hydroxyphenyl, 3-hydroxyphenyl, 4-hydroxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromobenzene group, 3-fluoro-4-bromophenyl, 3-chloro-4-bromophenyl, 2,3,4-trichlorophenyl, 2-methoxy-4-chlorophenyl, 2-hydroxy-4-chlorophenyl, 2-hydroxy-4-methoxyphenyl, 3-fluoro-4-(4-methylpiperazinyl)phenyl, 4-(N,N-dimethylamino)phenyl, and 3-fluoro-4-(4-morpholinyl)phenyl; $R_3$ and $R_4$ are hydrogen, or $R_3$ and $R_4$ are at each occurrence selected from the group consisting of —$CH_2CH_2COOH$, —$CH_2CH_2CH_2CH_2COOH$, —CH$_2$CH=CHCH$_2$COOH, and —CH$_2$CH$_2$CH$_2$CH$_2$CH$_2$CH$_2$COOH; or R$_3$ and R$_4$ are —COR$_5$; R$_5$ is selected from the group consisting of 3-pyridyl, —CH$_2$CH$_2$COOH, —CH$_2$CH$_2$CH$_2$CH$_2$COOH, —CH$_2$CH=CHCH$_2$COOH, and —CH$_2$CH$_2$CH$_2$CH$_2$CH$_2$CH$_2$COOH.

In a class of this embodiment, R$_1$ and R$_2$ are at each occurrence selected from the group consisting of hydrogen, phenyl, 2-methoxyphenyl, 3-methoxyphenyl, 4-methoxyphenyl, 3,4,5-trimethoxyphenyl, 2-hydroxyphenyl, 3-hydroxyphenyl, 4-hydroxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorobenzene group, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromophenyl, 3-fluoro-4-bromophenyl, 3-chloro-4-bromophenyl, 2,3,4-trichlorophenyl, 2-methoxy-4-chlorophenyl, 2-hydroxy-4-chlorophenyl, 2-hydroxy-4-methoxyphenyl, 3-fluoro-4-(4-methylpiperazinyl)phenyl, 4-(N,N-dimethylamino)phenyl, and 3-fluoro-4-(4-morpholinyl)phenyl; R$_1$ is different from R$_2$; R$_3$ and R$_4$ are hydrogen; or R$_3$ and R$_4$ are at each occurrence selected from the group consisting of CH$_2$CH$_2$COOH, CH$_2$CH$_2$CH$_2$CH$_2$COOH, CH$_2$CHCHCH$_2$COOH, and CH$_2$CH$_2$CH$_2$CH$_2$CH$_2$CH$_2$CH$_2$COOH; or R$_3$ and R$_4$ are COR$_5$; R$_5$ is 3-pyridyl or CH$_2$CH$_2$COOH; and R$_3$ is the same as R$_4$.

In a class of this embodiment, one of R$_1$ and R$_2$ is hydrogen, and the other is selected from the group consisting of phenyl, 2-methoxyphenyl, 3-methoxyphenyl, 4-methoxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromophenyl, 3-fluoro-4-bromophenyl, 3-chloro-4-bromophenyl, 2-methoxy-4-chlorophenyl, 4-hydroxyphenyl, 3,4,5-trimethoxyphenyl, 3-fluoro-4-(4-methylpiperazinyl)phenyl, 4-(N,N-dimethylamino)phenyl, and 3-fluoro-4-(4-morpholinyl)phenyl; R$_3$ and R$_4$ are hydrogen; or R$_3$ and R$_4$ are at each occurrence selected from the group consisting of CH$_2$CH$_2$COOH, CH$_2$CH$_2$CH$_2$CH$_2$COOH, CH$_2$CHCHCH$_2$COOH, and CH$_2$CH$_2$CH$_2$CH$_2$CH$_2$CH$_2$CH$_2$COOH; or R$_3$ and R$_4$ are COR$_5$; where R$_5$ is selected from 3-pyridyl and CH$_2$CH$_2$COOH; and R$_3$ is the same as R$_4$.

In a class of this embodiment, the compounds having the structure of Formula I is as defined herein:

ADY-1: R$_1$=H, R$_2$=4-Cl—C$_6$H$_4$, R$_3$=R$_4$=H;
ADY-2: R$_1$=H, R$_2$=4-Br—C$_6$H$_4$, R$_3$=R$_4$=H;
ADY-3: R$_1$=H, R$_2$=4-F—C$_6$H$_4$, R$_3$=R$_4$=H;
ADY-4: R$_1$=H, R$_2$=2-Cl—C$_6$H$_4$, R$_3$=R$_4$=H;
ADY-5: R$_1$=H, R$_2$=C$_6$H$_5$, R$_3$=R$_4$=H;
ADY-6: R$_1$=H, R$_2$=3,4-difluorophenyl, R$_3$=R$_4$=H;
ADY-7: R$_1$=H, R$_2$=3-CH$_3$O—C$_6$H$_4$, R$_3$=R$_4$=H;
ADY-8: R$_1$=H, R$_2$=4-OH—C$_6$H$_4$, R$_3$=R$_4$=H;
ADY-9: R$_1$=H, R$_2$=3,4,5-trimethoxyphenyl, R$_3$=R$_4$=H;
ADY-10: R$_1$=H, R$_2$=3-Cl—C$_6$H$_4$, R$_3$=R$_4$=H;
ADY-11: R$_1$=H, R$_2$=3-F-4-(N-methylpiperidine)-C$_6$H$_3$, R$_3$=R$_4$=H;
ADY-12: R$_1$=H, R$_2$=4-CH$_3$O—C$_6$H$_4$, R$_3$=R$_4$=H;
ADY-13: R$_1$=H, R$_2$=3-F-4-morpholine-C$_6$H$_3$, R$_3$=R$_4$=H;
ADY-14: R$_1$=H, R$_2$=4-(N—(CH$_3$)$_2$)-C$_6$H$_4$, R$_3$=R$_4$=H;
ADY-15: R$_1$=H, R$_2$=3,4-difluorophenyl, R$_3$=R$_4$=COR$_5$, R$_5$=3-pyridyl;
ADY-16: R$_1$=H, R$_2$=C$_6$H$_5$, R$_3$=R$_4$=COR$_5$, R$_5$=3-pyridyl;
ADY-17: R$_1$=H, R$_2$=4-Cl—C$_6$H$_4$, R$_3$=R$_4$=COR$_5$, R$_5$=CH$_2$CH$_2$COOH.

The structural data parameters of the compounds are described as follows:

ADY-1: mp 197-199° C.; IR 3415, 2931, 1762, 1650, 1587, 1491, 1091, 1041, 1021, 921 cm$^{-1}$; $^1$H NMR (400 MHz, CDCl$_3$) δ 7.69 (d, J=8.6 Hz, 2H), 7.36 (d, J=8.6 Hz, 2H), 7.28 (d, J=1.7 Hz, 1H), 5.93 (s, 1H), 4.83 (t, J=8.4 Hz, 1H), 4.28 (d, J=10.6 Hz, 1H), 3.48 (d, J=11.3 Hz, 1H), 3.43-3.34 (m, 1H), 3.02 (d, J=8.0 Hz, 1H), 2.85 (d, J=3.5 Hz, 1H), 2.48 (dd, J=13.8, 8.1 Hz, 1H), 2.23 (m, 1H), 2.15-2.05 (m, 1H), 1.89-1.72 (m, 3H), 1.58-1.43 (m, 4H), 1.28 (s, 3H), 1.13 (s, 3H), 1.09-0.99 (m, 2H), 0.97 (s, 3H); $^{13}$C NMR (100 MHz, CDCl$_3$) δ 168.75, 147.62, 137.25, 137.14, 134.85, 131.61, 131.57 (2C), 129.05 (2C), 111.76, 82.93, 80.89, 72.85, 64.22, 57.92, 52.75, 42.56, 38.99, 36.26, 35.66, 33.26, 31.45, 27.48, 22.78, 18.18, 16.45.

ADY-2: mp 189-190° C.; IR 3343, 2922, 2872, 1754, 1644, 1581, 1486, 1451, 1039, 1019, 920 cm$^{-1}$; $^1$H NMR (400 MHz, CDCl$_3$) δ 7.53 (d, J=8.6 Hz, 2H), 7.42 (d, J=8.5 Hz, 2H), 7.19 (d, J=1.6 Hz, 1H), 5.83 (s, 1H), 4.73 (t, J=8.5 Hz, 1H), 4.19 (d, J=11.0 Hz, 1H), 3.38 (d, J=10.4 Hz, 1H), 3.34-3.25 (m, 1H), 2.39 (dd, J=13.8, 8.1 Hz, 1H), 2.14 (m, 1H), 2.06-1.99 (m, 1H), 1.74-1.59 (m, 3H), 1.50-1.32 (m, 4H), 1.19 (s, 3H), 1.04 (s, 3H), 1.00-0.90 (m, 2H), 0.88 (s, 3H); $^{13}$C NMR (100 MHz, CDCl$_3$) δ 168.74, 147.72, 137.32, 137.16, 132.01 (3C), 131.78 (2C), 123.25, 111.83, 82.94, 80.83, 72.84, 64.22, 57.91, 52.73, 42.51, 38.99, 36.25, 35.65, 33.24, 31.45, 27.44, 22.80, 18.18, 16.45.

ADY-3: mp 180-182° C.; IR 3403, 2931, 1765, 1654, 1599, 1508, 1451, 1365, 1236, 1041, 1019, 921 cm$^{-1}$; $^1$H NMR (400 MHz, CDCl$_3$) δ 7.66 (dd, J=7.5, 5.6 Hz, 2H), 7.20 (s, 1H), 6.98 (dd, J=12.4, 4.8 Hz, 2H), 5.87 (s, 1H), 4.74 (t, J=8.5 Hz, 1H), 4.19 (d, J=8.6 Hz, 1H), 3.44-3.33 (m, 1H), 2.38 (dd, J=13.7, 8.1 Hz, 1H), 2.17-2.11 (m, 1H), 2.04-2.00 (m, 1H), 1.74-1.60 (m, 3H), 1.53-1.40 (m, 4H), 1.18 (s, 3H), 1.05 (s, 3H), 0.95 (m, 2H), 0.88 (s, 3H); $^{13}$C NMR (100 MHz, CDCl$_3$) δ 168.92, 162.85 (d, J=250 Hz), 146.99 (d, J=2 Hz), 137.23, 136.79, 132.38, 132.29, 129.39 (d, J=3 Hz), 116.07, 115.85, 111.91, 82.90, 80.90, 72.84, 64.21, 57.94, 52.76, 42.57, 39.00, 36.26, 35.66, 33.27, 31.45, 27.48, 22.77, 18.18, 16.45.

ADY-4: mp 248-249° C.; IR 3374, 2967, 2931, 1764, 1644, 1611, 1469, 1363, 1036, 1015, 922, 755, 693 cm$^{-1}$; $^1$H NMR (400 MHz, DMSO) δ 8.05 (d, J=7.8 Hz, 1H), 7.78 (s, 1H), 7.54 (d, J=8.0 Hz, 1H), 7.44 (t, J=7.6 Hz, 1H), 7.37 (t, J=7.6 Hz, 1H), 6.60 (s, 1H), 5.08 (d, J=4.7 Hz, 1H), 4.68 (t, J=8.4 Hz, 1H), 4.12 (dd, J=7.7, 2.5 Hz, 1H), 3.93 (dd, J=10.9, 2.5 Hz, 1H), 3.31-3.15 (m, 2H), 2.31-2.21 (m, 1H), 2.15-2.03 (m, 2H), 1.71-1.59 (m, 2H), 1.54 (m, 2H), 1.49-1.35 (m, 3H), 1.10 (s, 3H), 1.08 (s, 3H), 1.03-0.90 (m, 2H), 0.89 (s, 3H); $^{13}$C NMR (100 MHz, DMSO) δ 168.70, 149.33, 138.58, 137.55, 133.53, 131.73, 131.25, 130.65, 130.28, 128.13, 107.46, 82.85, 79.36, 72.29, 63.32, 57.77, 52.27, 42.39, 39.06, 36.44, 35.65, 32.81, 31.44, 27.63, 23.65, 18.64, 16.43.

ADY-5: mp 242-243° C.; IR 3277, 2968, 2932, 1747, 1653, 1610, 1451, 1365, 1034, 1017, 922, 774, 691 cm$^{-1}$; $^1$H NMR (400 MHz, CDCl$_3$) δ 7.68 (d, J=7.3 Hz, 2H), 7.31 (t, J=7.4 Hz, 2H), 7.25 (d, J=6.0, 3.8 Hz, 1H), 7.21 (d, J=1.7 Hz, 1H), 5.90 (s, 1H), 4.76 (t, J=8.5 Hz, 1H), 4.20 (d, J=11.1 Hz, 1H), 3.40 (d, J=11.1 Hz, 1H), 3.34-3.26 (m, 1H), 2.83 (d, J=8.0 Hz, 1H), 2.59 (s, 1H), 2.40 (dd, J=13.8, 8.1 Hz, 1H), 2.16 (m, 1H), 2.03 (m, 1H), 1.73-1.59 (m, 3H), 1.54-1.38 (m, 4H), 1.20 (s, 3H), 1.06 (s, 3H), 1.01-0.91 (m, 2H), 0.89 (s, 3H); $^{13}$C NMR (100 MHz, CDCl$_3$) δ 169.03, 147.37, 137.32, 136.84, 133.10, 130.47 (2C), 129.00, 128.81 (2C), 113.22, 82.88, 80.94, 72.87, 64.22, 57.95, 52.78, 42.60, 39.00, 36.28, 35.67, 33.29, 31.46, 27.50, 22.76, 18.19, 16.45.

ADY-6: mp 185-186° C.; IR 3374, 2927, 1762, 1654, 1602, 1517, 1431, 1302, 1277, 1039, 1019, 917 cm$^{-1}$; $^1$H NMR (400 MHz, CDCl$_3$) δ 7.59 (ddd, J=11.3, 7.8, 1.8 Hz, 1H), 7.37-7.30 (m, 1H), 7.19 (d, J=1.5 Hz, 1H), 7.08 (dd, J=18.3, 8.5 Hz, 1H), 5.81 (s, 1H), 4.74 (t, J=8.5 Hz, 1H), 4.19 (d, J=10.9 Hz, 1H), 3.38 (d, J=9.8 Hz, 1H), 3.33-3.25 (m, 1H), 2.39 (dd, J=13.7, 8.1 Hz, 1H), 2.19-2.10 (m, 1H), 2.06-1.96 (m, 1H), 1.78-1.59 (m, 3H), 1.51-1.30 (m, 4H), 1.19 (s, 3H), 1.05 (s, 3H), 1.00-0.90 (m, 2H), 0.89 (s, 3H); $^{13}$C NMR (100 MHz, CDCl$_3$) δ 168.56, 151.66 (t, J=12 Hz), 149.16 (dd, J=8, 13 Hz), 147.67 (d, J=3 Hz), 137.52, 137.00, 130.23 (dd, J=4, 7 Hz), 126.90 (dd, J=3, 6 Hz), 118.84 (d, J=18 Hz), 117.60 (d, J=17 Hz), 110.70, 82.98, 80.81, 72.81, 64.22, 57.89, 52.71, 42.49, 38.98, 36.23, 35.65, 33.23, 31.43, 27.42, 22.80, 18.17, 16.44.

ADY-7: mp 214-215° C.; IR 3353, 2933, 1759, 1596, 1573, 1463, 1266, 1019, 928 cm$^{-1}$; $^1$H NMR (400 MHz, CDCl$_3$) δ 7.24 (d, J=3.3 Hz, 2H), 7.22 (s, 1H), 7.20 (s, 1H), 6.84-6.78 (m, 1H), 5.87 (s, 1H), 4.75 (t, J=8.5 Hz, 1H), 4.20 (d, J=11.1 Hz, 1H), 3.77 (s, 3H), 3.40 (dd, J=11.6, 3.9 Hz, 1H), 3.30 (d, J=11.0 Hz, 1H), 2.84 (s, 1H), 2.60 (s, 1H), 2.40 (dd, J=13.8, 8.1 Hz, 1H), 2.15 (dd, J=11.2, 3.6 Hz, 1H), 2.08-1.99 (m, 1H), 1.72-1.61 (m, 3H), 1.51-1.36 (m, 4H), 1.20 (s, 3H), 1.05 (s, 3H), 0.95 (m, 2H), 0.89 (s, 3H); $^{13}$C NMR (100 MHz, CDCl$_3$) δ 168.89, 159.75, 147.51, 137.30, 136.96, 134.33, 129.73, 123.20, 115.26, 115.07, 113.09, 82.88, 80.94, 72.87, 64.22, 57.94, 55.35, 52.77, 42.59, 39.00, 36.28, 35.67, 33.28, 31.46, 27.49, 22.76, 18.19, 16.45.

ADY-8: mp 224-226° C.; IR 3380, 2933, 1727, 1597, 1458, 1264, 1021, 921 cm$^{-1}$; $^1$H NMR (400 MHz, DMSO) δ 10.16 (s, 1H), 7.88 (dd, J=7.8, 1.4 Hz, 1H), 7.70 (d, J=1.3 Hz, 1H), 7.17 (m, 1H), 6.90 (d, J=3.2 Hz, 1H), 6.88 (d, J=2.6 Hz, 1H), 6.59 (s, 1H), 5.10 (d, J=4.7 Hz, 1H), 4.66 (t, J=8.2 Hz, 1H), 4.13 (dd, J=7.7, 2.6 Hz, 1H), 3.94 (dd, J=10.9, 2.5 Hz, 1H), 3.28-3.20 (m, 2H), 2.25 (dd, J=13.5, 8.0 Hz, 1H), 2.15-2.02 (m, 2H), 1.65 (dd, J=14.8, 6.5 Hz, 1H), 1.53 (d, J=7.5 Hz, 2H), 1.43 (m, 3H), 1.10 (s, 3H), 1.07 (s, 3H), 0.93 (m, 2H), 0.89 (s, 3H); $^{13}$C NMR (100 MHz, DMSO) δ 169.20, 156.47, 147.14, 139.03, 135.35, 130.83, 120.56, 120.00, 116.01, 110.32, 107.45, 82.74, 79.37, 72.19, 63.32, 57.86, 52.25, 42.38, 39.08, 36.43, 35.65, 32.89, 31.40, 27.63, 23.64, 18.64, 16.46.

ADY-9: mp 225-226° C.; IR 3416, 2940, 1762, 1578, 1504, 1247, 1126, 1086, 1018, 921 cm$^{-1}$; $^1$H NMR (400 MHz, DMSO) δ 7.05 (s, 1H), 6.81 (s, 1H), 6.75 (s, 2H), 5.08 (d, J=4.7 Hz, 1H), 4.69 (t, J=8.4 Hz, 1H), 4.12 (dd, J=7.6, 2.7 Hz, 1H), 3.93 (dd, J=11.0, 2.6 Hz, 1H), 3.81 (s, 9H), 3.28-3.21 (m, 2H), 2.25-2.16 (m, 2H), 2.09-2.04 (m, 1H), 1.69-1.63 (m, 2H), 1.56-1.53 (m, 2H), 1.50-1.43 (m, 3H), 1.10 (s, 3H), 1.08 (s, 3H), 1.01-0.92 (m, 2H), 0.90 (s, 3H); $^{13}$C NMR (100 MHz, DMSO) δ 168.02, 153.57 (2C), 153.40, 148.48, 139.88, 133.26, 128.86, 115.25, 107.06 (2C), 82.91, 79.35, 72.27, 63.32, 60.64, 60.59, 57.78, 56.33, 52.20, 42.37, 42.32, 39.06, 36.36, 35.66, 32.66, 31.39, 27.59, 23.62, 18.60, 16.45.

ADY-10: mp 229-230° C.; IR 3347, 2908, 1768, 1476, 1036, 1017, 924 cm$^{-1}$; $^1$H NMR (400 MHz, DMSO) δ 7.76 (s, 1H), 7.65 (d, J=7.7 Hz, 1H), 7.60 (s, 1H), 7.47 (t, J=7.8 Hz, 1H), 7.41 (d, J=8.1 Hz, 1H), 6.32 (s, 1H), 5.09 (d, J=4.7 Hz, 1H), 4.67 (t, J=8.4 Hz, 1H), 4.12 (dd, J=7.7, 2.6 Hz, 1H), 3.93 (dd, J=10.9, 2.5 Hz, 1H), 3.31-3.18 (m, 2H), 2.26 (dd, J=13.5, 8.1 Hz, 1H), 2.17-2.03 (m, 2H), 1.64 (dd, J=15.2, 6.7 Hz, 2H), 1.54 (t, J=7.4 Hz, 2H), 1.44 (dd, J=12.0, 5.8 Hz, 3H), 1.10 (s, 3H), 1.06 (s, 3H), 0.95 (dd, J=17.4, 6.6 Hz, 2H), 0.89 (s, 3H); $^{13}$C NMR (100 MHz, DMSO) δ 168.59, 148.66, 138.20, 137.40, 135.69, 134.00, 131.24, 129.56, 129.05, 128.90, 110.99, 82.84, 79.36, 72.29, 63.32, 57.76, 52.25, 42.39, 39.06, 36.42, 35.65, 32.76, 31.40, 27.63, 23.65, 18.63, 16.43.

ADY-11: mp 219-221° C.; IR 3425, 2933, 1756, 1599, 1511, 1252, 1142, 1022, 923 cm$^{-1}$; $^1$H NMR (400 MHz, DMSO) δ 7.56 (s, 1H), 7.49 (dd, J=14.9, 1.4 Hz, 1H), 7.41 (d, J=8.6 Hz, 1H), 7.04 (t, J=9.0 Hz, 1H), 6.24 (s, 1H), 5.09 (d, J=4.7 Hz, 1H), 4.65 (t, J=8.3 Hz, 1H), 4.12 (d, J=5.7 Hz, 1H), 3.98-3.89 (m, 1H), 3.30-3.19 (m, 2H), 3.12-3.06 (m, 4H), 2.49-2.42 (m, 4H), 2.29-2.23 (m, 1H), 2.22 (s, 3H), 2.14-2.02 (m, 2H), 1.70-1.57 (m, 2H), 1.54 (dd, J=11.3, 5.8 Hz, 2H), 1.49-1.35 (m, 3H), 1.10 (s, 3H), 1.05 (s, 3H), 1.01-0.90 (m, 2H), 0.88 (s, 3H); $^{13}$C NMR (100 MHz, DMSO) δ 168.81, 154.55 (d, J=242 Hz), 146.87, 140.58 (d, J=8 Hz), 138.28, 135.63, 127.74, 127.17 (d, J=9 Hz), 119.49 (d, J=4 Hz), 117.31 (d, J=22 Hz), 111.98, 82.74, 79.36, 72.25, 63.32, 57.83, 54.96, 52.24, 49.95, 49.91, 49.06, 46.21, 42.38, 39.08, 36.41, 35.64, 32.85, 31.42, 27.63, 23.64, 18.63, 16.45.

ADY-12: mp 215-216° C.; IR 3329, 2939, 1749, 1598, 1511, 1463, 1303, 1255, 1175, 1020, 921 cm$^{-1}$; $^1$H NMR (400 MHz, DMSO) δ 7.68 (d, J=8.8 Hz, 2H), 7.57 (s, 1H), 7.01 (d, J=8.8 Hz, 2H), 6.27 (s, 1H), 5.08 (d, J=4.7 Hz, 1H), 4.66 (t, J=8.3 Hz, 1H), 4.12 (dd, J=7.6, 2.4 Hz, 1H), 3.93 (dd, J=10.9, 2.4 Hz, 1H), 3.80 (s, 3H), 3.24 (ddd, J=15.7, 10.6, 6.3 Hz, 2H), 2.25 (dd, J=13.5, 8.0 Hz, 1H), 2.15-2.01 (m, 2H), 1.64 (dd, J=14.4, 6.2 Hz, 2H), 1.55 (dd, J=16.5, 9.0 Hz, 2H), 1.41 (dd, J=29.2, 5.2 Hz, 3H), 1.10 (s, 3H), 1.06 (s, 3H), 1.02-0.90 (m, 2H), 0.89 (s, 3H); $^{13}$C NMR (100 MHz, DMSO) δ 169.05, 160.23, 146.24, 138.53, 135.16, 132.25 (2C), 126.26, 115.01 (2C), 112.99, 82.72, 79.36, 72.24, 63.31, 57.85, 55.73, 52.23, 42.38, 39.09, 36.42, 35.65, 32.89, 31.44, 27.63, 23.64, 18.64, 16.46.

ADY-13: mp 213-214° C.; IR 3372, 2943, 1750, 1598, 1513, 1446, 1252, 1123, 1020, 923 cm$^{-1}$; $^1$H NMR (400 MHz, DMSO) δ 7.56 (d, J=1.2 Hz, 1H), 7.50 (dd, J=14.8, 1.5 Hz, 1H), 7.43 (dd, J=8.5, 1.4 Hz, 1H), 7.06 (t, J=9.0 Hz, 1H), 6.25 (s, 1H), 5.09 (d, J=4.7 Hz, 1H), 4.65 (t, J=8.2 Hz, 1H), 4.13 (dd, J=7.6, 2.5 Hz, 1H), 3.93 (dd, J=11.0, 2.5 Hz, 1H), 3.77-3.71 (m, 4H), 3.30-3.19 (m, 2H), 3.12-3.06 (m, 4H), 2.24 (dd, J=13.4, 8.0 Hz, 1H), 2.14-2.01 (m, 2H), 1.68-1.60 (m, 2H), 1.56-1.50 (m, 2H), 1.49-1.39 (m, 3H), 1.10 (s, 3H), 1.05 (s, 3H), 0.99-0.90 (m, 2H), 0.88 (s, 3H); $^{13}$C NMR (100 MHz, CDCl$_3$) δ 168.39, 154.19 (d, J=243 Hz), 146.56, 140.01 (d, J=8 Hz), 137.87, 135.32, 127.35, 127.08 (d, J=9 Hz), 118.92 (d, J=3 Hz), 116.95 (d, J=22 Hz), 111.44, 82.35, 78.95, 71.82, 66.06 (2C), 62.90, 57.41, 51.81, 50.04, 50.00, 41.96, 38.66, 35.97, 35.22, 32.42, 30.99, 27.19, 23.21, 18.20, 16.02.

The disclosure also provides 14-deoxy11,12-didehydro-7,8-ene-andrographolide (ADC):

ADC and a 15-substituted derivative of ADC as shown in formula II:

II where: $R_1$ and $R_2$ are at each occurrence selected from the group consisting of hydrogen, methyl, substituted or unsubstituted aromatic ring, and substituted or unsubstituted heteroaromatic ring; the aromatic ring and heteroaromatic ring include, but are not limited to, the following: phenyl, pyridyl, furyl, thienyl, and pyrrolyl. The substituted groups mentioned herein can be substituted with one or more of appropriate substituents which may be the same or different. Optionally, $R_1$ is connected to $R_2$ to form a substituted cyclic ring such as cyclohexane and cyclopentane; and $R_1$ and $R_2$ are the same or different substituents.

In a class of this embodiment, $R_1$ and $R_2$ are at each occurrence selected from the group consisting of hydrogen, phenyl, methyl, 2-furyl, 2-methoxyphenyl, 3-methoxyphenyl, 4-methoxyphenyl, 3,4,5-trimethoxyphenyl, 2-hydroxyphenyl, 3-hydroxyphenyl, 4-hydroxyphenyl, 2-nitrophenyl, 3-nitrophenyl, 4-nitrophenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromobenzene group, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromophenyl, 3-fluoro-4-bromophenyl, 3-chloro-4-bromophenyl, 2,3,4-trichlorophenyl, 2-methoxy-4-chlorophenyl, 2-hydroxy-4-chlorophenyl, 2-hydroxy-4-methoxyphenyl, 3-amino-4-chlorophenyl, 2-amino-4-chlorophenyl, 4-(N,N-dimethylamino)phenyl, 3-fluoro-4-(4-morpholinyl)phenyl, and 3-fluoro-4-(4-methylpiperazinyl)phenyl; or $R_1$ is connected to $R_2$ to form a cyclohexyl or cyclopentyl.

In a class of this embodiment, one of $R_1$ and $R_2$ is hydrogen, and the other is selected from the group consisting of methyl, 2-furyl, phenyl, 2-methoxyphenyl, 3-methoxyphenyl, 4-methoxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 3,4,5-trimethoxybenzene group, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromophenyl, 3-fluoro-4-bromophenyl, 3-chloro-4-bromophenyl, 2-methoxy-4-chlorophenyl, 4-(N,N-dimethylamino)phenyl, 3-fluoro-4-(4-morpholinyl)phenyl, 3-fluoro-4-(4-methylpiperazinyl)phenyl, 2-hydroxyphenyl, 3-hydroxyphenyl, 4-hydroxyphenyl, 2-nitrophenyl, 3-nitrophenyl, and 4-nitrophenyl; or $R_1$ is connected to $R_2$ to form a cyclohexyl.

The preferred compounds having the structure of Formula II is as defined herein:
  ADC-1: $R_1$=H, $R_2$=4-Cl—$C_6H_4$;
  ADC-2: $R_1$=H, $R_2$=$C_6H_5$;
  ADC-3: $R_1$=H, $R_2$=3-Cl—$C_6H_4$;
  ADC-4: $R_1$=H, $R_2$=4-Br—$C_6H_4$;
  ADC-5: $R_1$=H, $R_2$=4-F—$C_6H_4$;
  ADC-6: $R_1$=H, $R_2$=3,4-difluorophenyl;
  ADC-7: $R_1$=H, $R_2$=2-Cl—$C_6H_4$;
  ADC-8: $R_1$=H, $R_2$=3-$CH_3$O—$C_6H_4$;
  ADC-9: $R_1$=H, $R_2$=4-N($CH_3$)$_2$—$C_6H_4$;
  ADC-10: $R_1$=H, $R_2$=3-F-4-(4-morpholinyl)-$C_6H_3$;
  ADC-11: $R_1$=H, $R_2$=4-$CH_3$O—$C_6H_4$;
  ADC-12: $R_1$=H, $R_2$=2-HO—$C_6H_4$;
  ADC-13: $R_1$=H, $R_2$=4-HO—$C_6H_4$;
  ADC-14: $R_1$=H, $R_2$=3-$NO_2$—$C_6H_4$;
  ADC-15: $R_1$=H, $R_2$=3,4,5-trimethoxyphenyl;
  ADC-16: $R_1$=H, $R_2$=2-furyl;
  ADC-17: $R_1$ is connected to $R_2$ to form a cyclohexyl.

The structural data parameter of the compounds are as follows:
  ADC: $^1$H NMR (400 MHz, CDCl$_3$) δ 7.21 (s, 1H), 6.64 (dd, J=15.7, 10.6 Hz, 1H), 6.17 (d, J=15.8 Hz, 1H), 5.52 (s, 1H), 4.85 (d, J=1.6 Hz, 2H), 4.30 (d, J=11.0 Hz, 1H), 3.51 (t, J=9.5 Hz, 2H), 2.94 (d, J=7.6 Hz, 1H), 2.63 (s, 1H), 2.44 (d, J=10.8 Hz, 1H), 2.12 (d, J=17.3 Hz, 1H), 1.97-1.86 (m, 1H), 1.85-1.76 (m, 1H), 1.75-1.66 (m, 2H), 1.53 (s, 3H), 1.36 (dd, J=12.4, 4.6 Hz, 1H), 1.27 (s, 3H), 1.24-1.14 (m, 1H), 0.84 (s, 3H). $^{13}$C NMR (100 MHz, DMSO-d$_6$) δ 172.87, 147.12, 136.32, 132.56, 127.48, 122.64, 122.15, 79.37, 70.65, 62.99, 59.98, 49.97, 42.08, 38.27, 35.94, 27.80, 23.70, 23.23, 22.67, 15.95. HRMS (ESI): m/z calcd for $C_{24}H_{28}NaO_4$(M+Na)$^+$, 355.1880; found, 355.1878.
  ADC-1: $R_1$=H, $R_2$=4-O—Cl—$C_6H_4$; $^1$H NMR (400 MHz, DMSO-d$_6$) δ 7.76 (d, J=8.6 Hz, 2H), 7.74 (s, 1H), 7.52 (d, J=8.6 Hz, 2H), 6.62 (dd, J=15.7, 10.6 Hz, 1H), 6.33 (d, J=17.3 Hz, 2H, overlap), 5.51 (s, 1H), 5.12 (s, 1H), 4.31 (s, 1H), 3.94 (d, J=10.9 Hz, 1H), 3.41 (d, J=10.5 Hz, 1H), 3.28-3.18 (m, 1H), 2.48 (s, 1H, overlap), 2.02 (s, 2H), 1.70-1.50 (m, 3H), 1.48 (s, 3H), 1.26 (dd, J=10.4, 6.5 Hz, 1H), 1.22-1.13 (m, 1H), 1.08 (s, 3H), 0.81 (s, 3H). $^{13}$C NMR (100 MHz, DMSO-$d_6$) δ 168.81, 148.37, 139.47, 137.27, 133.81, 132.71, 132.40, 132.18 (2C, overlap), 129.50 (2C, overlap), 126.75, 122.81, 122.20, 111.86, 79.35, 62.98, 60.23, 49.97, 42.13, 38.31, 36.23, 27.81, 23.72, 23.23, 22.70, 16.03. HRMS (ESI): m/z calcd for $C_{27}H_{31}ClNaO_4$ (M+Na)$^+$, 477.1809; found, 477.1810.

ADC-2: $R_1$=H, $R_2$=$C_6H_5$; $^1$H NMR (400 MHz, DMSO-$d_6$) δ 7.80 (d, J=7.6 Hz, 2H), 7.60 (s, 1H), 7.44 (t, J=7.6 Hz, 2H), 7.35 (t, J=7.4 Hz, 1H), 6.74 (dd, J=15.7, 10.7 Hz, 1H), 6.38 (d, J=15.7 Hz, 1H), 6.25 (s, 1H), 5.54 (s, 1H), 4.62 (s, 1H), 4.21 (d, J=10.8 Hz, 1H), 3.84 (d, J=7.6 Hz, 1H), 3.50-3.38 (m, 2H), 2.55 (d, J=10.4 Hz, 1H), 2.15-2.08 (m, 1H), 2.03-1.91 (m, 1H), 1.84-1.74 (m, 1H), 1.74-1.68 (m, 1H), 1.68-1.61 (m, 1H), 1.53 (s, 3H), 1.37 (dd, J=12.3, 4.8 Hz, 1H), 1.32-1.22 (m, 1H), 1.21 (s, 3H), 0.88 (s, 3H). $^{13}$C NMR (100 MHz, DMSO-$d_6$) δ 168.92, 148.50, 139.56, 136.85, 134.28, 132.88, 130.73 (2C, overlap), 129.27 (2C, overlap), 129.16, 127.11, 122.62, 122.52, 112.99, 80.62, 63.86, 60.97, 50.56, 42.42, 38.65, 36.49, 28.11, 23.64, 22.71, 22.27, 15.83. HRMS (ESI): m/z calcd for $C_{27}H_{32}NaO_4$(M+Na)$^+$, 443.2198; found, 443.2168.

ADC-3: $R_1$=H, $R_2$=3-O—$C_6H_4$; $^1$H NMR (400 MHz, Acetone-$d_6$) δ 8.22 (d, J=7.9 Hz, 1H), 7.74 (s, 1H), 7.53 (d, J=8.0 Hz, 1H), 7.47 (t, J=7.6 Hz, 1H), 7.42-7.35 (m, 1H), 6.79 (dd, J=15.7, 10.7 Hz, 1H), 6.59 (s, 1H), 6.42 (d, J=15.7 Hz, 1H), 5.57 (s, 1H), 4.65 (s, 1H), 4.24 (d, J=10.8 Hz, 1H), 3.87 (d, J=6.8 Hz, 1H), 3.60 (d, J=6.8 Hz, 1H), 3.52-3.46 (m, 1H), 2.59 (d, J=10.3 Hz, 1H), 2.14 (d, J=18.0 Hz, 1H), 2.00 (t, J=14.9 Hz, 1H), 1.86-1.77 (m, 1H), 1.76-1.71 (m, 1H), 1.70-1.63 (m, 1H), 1.56 (s, 3H), 1.39 (dd, J=12.3, 4.7 Hz, 1H), 1.34-1.25 (m, 1H), 1.22 (s, 3H), 0.90 (s, 3H). $^{13}$C NMR (100 MHz, Acetone-$d_6$) δ 168.24, 149.45, 139.93, 136.37, 133.62, 132.34, 131.60, 131.43, 129.92, 129.77, 127.54, 127.46, 122.25, 121.96, 107.09, 80.17, 63.42, 60.52, 50.12, 41.99, 38.21, 36.09, 27.67, 23.20, 22.28, 21.82, 15.40. HRMS (ESI): m/z calcd for $C_{27}H_{31}ClNaO_4$(M+Na)$^+$, 477.1809; found, 477.1807.

ADC-4: $R_1$=H, $R_2$=4-Br—$C_6H_4$; $^1$H NMR (400 MHz, DMSO-$d_6$) δ 7.73 (s, 1H), 7.69 (d, J=8.7 Hz, 2H), 7.65 (d, J=8.7 Hz, 2H), 6.62 (dd, J=15.7, 10.6 Hz, 1H), 6.32 (t, J=7.8 Hz, 2H), 5.51 (s, 1H), 5.13 (d, J=4.8 Hz, 1H), 4.31 (d, J=5.1 Hz, 1H), 3.94 (d, J=10.7 Hz, 1H), 3.41 (dd, J=10.7, 7.8 Hz, 1H), 3.27-3.19 (m, 1H), 2.51-2.47 (m, 1H, overlap), 2.02 (s, 2H), 1.71-1.50 (m, 3H), 1.47 (s, 3H), 1.26 (dd, J=10.4, 6.4 Hz, 1H), 1.23-1.12 (m, 1H), 1.08 (s, 3H), 0.81 (s, 3H). $^{13}$C NMR (100 MHz, DMSO-$d_6$) δ 168.81, 148.44, 139.50, 137.27, 133.01, 132.42 (2C, overlap), 132.39 (3C, overlap), 126.79, 122.80, 122.65, 122.21, 111.95, 79.35, 62.98, 60.24, 49.96, 42.13, 38.30, 36.22, 27.81, 23.71, 23.23, 22.70, 16.03. HRMS (ESI): m/z calcd for $C_{27}H_{31}BrNaO_4$(M+Na)$^+$, 521.1303; found, 521.1306.

ADC-5: $R_1$=H, $R_2$=4-F—$C_6H_4$; $^1$H NMR (400 MHz, Acetone-$d_6$) δ 7.88 (dd, J=8.6, 5.7 Hz, 2H), 7.61 (s, 1H), 7.25 (t, J=8.8 Hz, 2H), 6.76 (dd, J=15.7, 10.7 Hz, 1H), 6.39 (d, J=15.7 Hz, 1H), 6.28 (s, 1H), 5.56 (s, 1H), 4.63 (d, J=4.3 Hz, 1H), 4.24 (d, J=10.8 Hz, 1H), 3.86 (d, J=8.1 Hz, 1H), 3.53-3.39 (m, 2H), 2.57 (d, J=10.3 Hz, 1H), 2.14 (d, J=17.8 Hz, 1H), 2.00 (t, J=14.9 Hz, 1H), 1.86-1.77 (m, 1H), 1.76-1.71 (m, 1H), 1.70-1.63 (m, 1H), 1.55 (s, 3H), 1.39 (dd, J=12.3, 4.7 Hz, 1H), 1.33-1.26 (m, 1H), 1.23 (s, 3H), 0.90 (s, 3H). $^{13}$C NMR (100 MHz, Acetone-$d_6$) δ 168.40, 162.64 (d, J=247 Hz), 147.76 (d, J=3 Hz), 139.17, 136.31, 132.43, 132.42, 132.35, 130.41 (d, J=3 Hz), 126.64, 122.20, 122.04, 115.90, 115.68, 111.24, 80.18, 63.43, 60.54, 50.13, 41.99, 38.22, 36.06, 27.67, 23.20, 22.27, 21.82, 15.38. HRMS (ESI): m/z calcd for $C_{27}H_{31}FNaO_4$(M+Na)$^+$, 461.2104; found, 461.2106.

ADC-6: $R_1$=H, $R_2$=3,4-diF-$C_6H_3$; $^1$H NMR (400 MHz, DMSO-$d_6$) δ7.79-7.72 (m, 2H), 7.63-7.57 (m, 1H), 7.52 (dd, J=18.9, 8.7 Hz, 1H), 6.63 (dd, J=15.7, 10.6 Hz, 1H), 6.33 (t, J=7.8 Hz, 2H), 5.51 (s, 1H), 5.13 (d, J=4.6 Hz, 1H), 4.31 (d, J=5.3 Hz, 1H), 3.94 (d, J=10.5 Hz, 1H), 3.40 (dd, J=10.7, 7.5 Hz, 1H), 3.27-3.18 (m, 1H), 2.48 (s, 1H, overlap), 2.02 (s, 2H), 1.67-1.49 (m, 3H), 1.47 (s, 3H), 1.26 (dd, J=10.4, 6.5 Hz, 1H), 1.23-1.13 (m, 1H), 1.08 (s, 3H), 0.81 (s, 3H). $^{13}$C NMR (100 MHz, DMSO-$d_6$) δ 168.69, 151.09 (dd, J=8, 13 Hz), 148.69 (d, J=13 Hz), 148.46 (d, J=2 Hz), 139.71, 137.10, 132.37, 131.48 (dd, J=4, 7 Hz), 127.84 (dd, J=3, 6 Hz), 126.97, 122.81, 122.11, 118.85 (d, J=18 Hz), 118.63 (d, J=17 Hz), 110.80, 79.35, 62.98, 60.23, 49.96, 42.13, 38.30, 36.23, 27.80, 23.71, 23.22, 22.68, 16.02. HRMS (ESI): m/z calcd for $C_{27}H_{30}F_2NaO_4$(M+Na)$^+$, 479.2010; found, 479.2013.

ADC-7: $R_1$=H, $R_2$=2-O—$C_6H_4$; $^1$H NMR (400 MHz, Acetone-$d_6$) δ 8.22 (d, J=7.9 Hz, 1H), 7.74 (s, 1H), 7.53 (d, J=8.0 Hz, 1H), 7.47 (t, J=7.6 Hz, 1H), 7.42-7.35 (m, 1H), 6.79 (dd, J=15.7, 10.7 Hz, 1H), 6.59 (s, 1H), 6.42 (d, J=15.7 Hz, 1H), 5.57 (s, 1H), 4.65 (s, 1H), 4.24 (d, J=10.8 Hz, 1H), 3.87 (d, J=6.8 Hz, 1H), 3.60 (d, J=6.8 Hz, 1H), 3.52-3.46 (m, 1H), 2.59 (d, J=10.3 Hz, 1H), 2.14 (d, J=18.0 Hz, 1H), 2.00 (t, J=14.9 Hz, 1H), 1.86-1.77 (m, 1H), 1.76-1.71 (m, 1H), 1.70-1.63 (m, 1H), 1.56 (s, 3H), 1.39 (dd, J=12.3, 4.7 Hz, 1H), 1.34-1.25 (m, 1H), 1.22 (s, 3H), 0.90 (s, 3H). $^{13}$C NMR (100 MHz, Acetone-$d_6$) δ 168.24, 149.45, 139.93, 136.37, 133.62, 132.34, 131.60, 131.43, 129.92, 129.77, 127.54, 127.46, 122.25, 121.96, 107.09, 80.17, 63.42, 60.52, 50.12, 41.99, 38.21, 36.09, 27.67, 23.20, 22.28, 21.82, 15.40. FIRMS (ESI): m/z calcd for $C_{27}H_{31}ClNaO_4$(M+Na)$^+$, 477.1809; found, 477.1807.

ADC-8: $R_1$=H, $R_2$=3-$CH_3$O—$C_6H_4$; $^1$H NMR (400 MHz, DMSO-$d_6$) δ 7.73 (s, 1H), 7.41-7.33 (m, 2H), 7.31 (s, 1H), 6.99-6.93 (m, 1H), 6.61 (dd, J=15.7, 10.6 Hz, 1H), 6.32 (t, J=7.8 Hz, 2H, overlap), 5.51 (s, 1H), 5.12 (s, 1H), 4.31 (d, J=4.9 Hz, 1H), 3.94 (d, J=10.8 Hz, 1H), 3.80 (s, 3H), 3.41 (dd, J=10.6, 6.6 Hz, 1H), 3.23 (d, J=10.3 Hz, 1H), 2.48 (s, 1H, overlap), 2.02 (s, 2H), 1.65-1.49 (m, 3H), 1.48 (s, 3H), 1.26 (dd, J=10.5, 6.4 Hz, 1H), 1.22-1.13 (m, 1H), 1.08 (s, 3H), 0.81 (s, 3H). $^{13}$C NMR (100 MHz, DMSO-$d_6$) δ 168.95, 159.88, 148.14, 139.24, 137.40, 134.98, 132.43, 130.44, 126.51, 123.16, 122.78, 122.20, 115.91, 115.00, 113.22, 79.36, 62.99, 60.22, 55.59, 49.97, 42.13, 38.30, 36.22, 27.82, 23.71, 23.23, 22.70, 16.02. HRMS (ESI): m/z calcd for $C_{28}H_{34}NaO_5$(M+Na)$^+$, 473.2304; found, 473.2306.

ADC-9: $R_1$=H, $R_2$=4-N$(CH_3)_2$—$C_6H_4$; $^1$H NMR (400 MHz, DMSO-$d_6$) δ 7.63 (s, 1H), 7.61 (d, J=9.0 Hz, 2H), 6.76 (d, J=9.0 Hz, 2H), 6.51 (dd, J=15.7, 10.5 Hz, 1H), 6.26 (d, J=15.7 Hz, 1H), 6.21 (s, 1H), 5.50 (s, 1H), 5.08 (s, 1H), 4.31 (s, 1H), 3.95 (d, J=10.9 Hz, 1H), 3.40 (d, J=10.9 Hz, 1H), 3.23 (dd, J=10.8, 4.1 Hz, 1H), 2.99 (s, 6H), 2.47 (d, J=9.8 Hz, 1H), 2.01 (s, 2H), 1.68-1.49 (m, 3H), 1.47 (s, 3H), 1.25 (dd, J=10.5, 6.2 Hz, 1H), 1.22-1.12 (m, 1H), 1.07 (d, J=6.5 Hz, 3H), 0.80 (s, 3H). $^{13}$C NMR (100 MHz, DMSO-$d_6$) δ 174.12, 155.72, 149.67, 142.10, 141.74, 137.42, 137.16 (2C, overlap), 128.16, 127.39, 127.31, 126.10, 119.83, 117.28 (2C, overlap), 84.15, 67.76, 65.01, 54.76, 46.87, 44.85 (2C, overlap), 43.08, 40.92, 32.59, 28.47, 27.98, 27.48, 20.77. HRMS (ESI): m/z calcd for $C_{29}H_{37}NNaO_4$(M+Na)$^+$, 486.2620; found, 486.2619.

ADC-10: $R_1$=H, $R_2$=3-F-4-(4-morpholinyl)-$C_6H_3$; $^1$H NMR (400 MHz, DMSO-$d_6$) δ 7.70 (s, 1H), 7.53 (d, J=14.8 Hz, 1H), 7.48 (d, J=8.6 Hz, 1H), 7.08 (t, J=9.0 Hz, 1H), 6.58 (dd, J=15.7, 10.6 Hz, 1H), 6.30 (d, J=16.0 Hz, 1H), 6.27 (s, 1H), 5.51 (s, 1H), 5.12 (s, 1H), 4.31 (s, 1H), 3.94 (d, J=10.9

Hz, 1H), 3.83-3.70 (m, 4H), 3.40 (d, J=12.2 Hz, 1H), 3.23 (d, J=7.3 Hz, 1H), 3.15-3.03 (m, 4H), 2.48 (s, 1H), 2.02 (s, 2H), 1.68-1.49 (m, 3H), 1.47 (s, 3H), 1.26 (dd, J=10.4, 6.3 Hz, 1H), 1.22-1.13 (m, 1H), 1.08 (s, 3H), 0.80 (s, 3H). $^{13}C$ NMR (100 MHz, DMSO-$d_6$) δ 168.92, 154.61 (d, J=243 Hz), 147.22, 140.50 (d, J=8 Hz), 138.77, 137.17, 132.47, 127.89 (d, J=2 Hz), 127.68 (d, J=8 Hz), 125.73, 122.75, 122.27, 119.36 (d, J=3 Hz), 117.64, 117.41, 112.36, 79.37, 66.48, 62.99, 60.24, 50.48, 50.44, 49.97, 42.12, 38.31, 36.21, 27.81, 23.71, 23.22, 22.70, 16.02. HRMS (ESI): m/z calcd for $C_{31}H_{38}FNNaO_5(M+Na)^+$, 546.2632; found, 546.2634.

ADC-11: $R_1$=H, $R_2$=4-$CH_3O$—$C_6H_4$; $^1H$ NMR (400 MHz, DMSO-$d_6$) δ 7.72 (d, J=8.8 Hz, 2H), 7.70 (s, 1H), 7.03 (d, J=8.8 Hz, 2H), 6.57 (dd, J=15.7, 10.6 Hz, 1H), 6.30 (t, J=7.8 Hz, 2H), 5.51 (s, 1H), 5.13 (s, 1H), 4.31 (s, 1H), 3.94 (d, J=10.8 Hz, 1H), 3.81 (s, 3H), 3.40 (d, J=10.8 Hz, 1H), 3.27-3.19 (m, 1H), 2.48 (s, 1H), 2.02 (s, 2H), 1.69-1.50 (m, 3H), 1.48 (s, 3H), 1.26 (dd, J=10.5, 6.3 Hz, 1H), 1.22-1.13 (m, 1H), 1.06 (s, 3H), 0.81 (s, 3H). $^{13}C$ NMR (100 MHz, DMSO-$d_6$) δ 169.15, 160.34, 146.47, 138.32, 137.49, 132.51, 132.43 (2C, overlap), 126.48, 125.24, 122.73, 122.33, 115.06 (2C, overlap), 113.51, 79.37, 62.99, 60.23, 55.77, 49.98, 42.12, 38.31, 36.19, 27.82, 23.71, 23.23, 22.71, 16.02. HRMS (ESI): m/z calcd for $C_{28}H_{34}NaO_5(M+Na)^+$, 473.2304; found, 473.2303.

ADC-12: $R_1$=H, $R_2$=2-HO—$C_6H_4$; $^1H$ NMR (400 MHz, DMSO-$d_6$) δ 10.19 (s, 1H), 7.91 (dd, J=7.8, 1.3 Hz, 1H), 7.79 (s, 1H), 7.21-7.16 (m, 1H), 6.91 (d, J=8.5 Hz, 2H), 6.62-6.53 (m, 2H), 6.29 (d, J=15.7 Hz, 1H), 5.51 (s, 1H), 5.13 (d, J=4.8 Hz, 1H), 4.31 (d, J=5.0 Hz, 1H), 3.94 (d, J=10.6 Hz, 1H), 3.44-3.38 (m, 1H), 3.26-3.19 (m, 1H), 2.50 (s, 1H), 2.02 (s, 2H), 1.65-1.50 (m, 3H), 1.48 (s, 3H), 1.26 (dd, J=10.5, 6.4 Hz, 1H), 1.23-1.16 (m, 1H), 1.08 (s, 3H), 0.81 (s, 3H). $^{13}C$ NMR (100 MHz, DMSO-$d_6$) δ 169.21, 156.53, 147.33, 138.46, 137.92, 132.50, 130.95, 128.78, 125.45, 122.74, 122.32, 120.75, 120.09, 116.05, 107.83, 79.36, 62.99, 60.20, 49.97, 42.12, 38.32, 36.19, 27.82, 23.71, 23.23, 22.72, 16.03. HRMS (ESI): m/z calcd for $C_{27}H_{32}NaO_5(M+Na)^+$, 459.2147; found, 459.2151.

ADC-13: $R_1$=H, $R_2$=4-HO—$C_6H_4$; $^1H$ NMR (400 MHz, DMSO-$d_6$) δ 10.10 (s, 1H), 7.65 (s, 1H), 7.61 (d, J=8.7 Hz, 2H), 6.85 (d, J=8.6 Hz, 2H), 6.54 (dd, J=15.7, 10.6 Hz, 1H), 6.28 (d, J=15.7 Hz, 1H), 6.24 (s, 1H), 5.49 (s, 1H), 5.17 (d, J=4.9 Hz, 1H), 4.41-4.32 (m, 1H), 3.99-3.90 (m, 1H), 3.40 (dd, J=10.7, 7.5 Hz, 1H), 3.28-3.18 (m, 1H), 2.47 (d, J=10.2 Hz, 1H), 2.01 (s, 2H), 1.69-1.48 (m, 3H), 1.46 (s, 3H), 1.25 (dd, J=10.9, 5.7 Hz, 1H), 1.21-1.11 (m, 1H), 1.07 (s, 3H), 0.79 (s, 3H). $^{13}C$ NMR (100 MHz, DMSO-$d_6$) δ 169.27, 159.02, 145.86, 137.96, 137.54, 132.70 (2C, overlap), 132.54, 124.97, 124.73, 122.69, 122.36, 116.50 (2C, overlap), 114.15, 79.41, 63.02, 60.21, 49.96, 42.08, 38.28, 36.15, 27.77, 23.68, 23.17, 22.69, 16.00. HRMS (ESI): m/z calcd for $C_{27}H_{32}NaO_5(M+Na)^+$, 459.2147; found, 459.2146.

ADC-14: $R_1$=H, $R_2$=3-$NO_2$—$C_6H_4$; $^1H$ NMR (400 MHz, Acetone-$d_6$) δ 8.35 (s, 1H), 8.26 (d, J=7.7 Hz, 1H), 7.94 (d, J=7.6 Hz, 1H), 7.71 (t, J=7.9 Hz, 1H), 7.58 (s, 1H), 6.72 (dd, J=15.7, 10.7 Hz, 1H), 6.32 (d, J=15.7 Hz, 1H), 6.06 (s, 1H), 5.58 (s, 1H), 4.91 (s, 2H), 4.50 (d, J=11.3 Hz, 1H), 3.76 (d, J=4.2 Hz, 1H), 3.73 (d, J=5.2 Hz, 1H), 2.64-2.50 (m, 2H), 2.18 (d, J=17.2 Hz, 1H), 1.91 (t, J=15.0 Hz, 1H), 1.81 (d, J=13.4 Hz, 1H), 1.75-1.66 (m, 1H), 1.56 (s, 3H), 1.53-1.48 (m, 1H), 1.47 (s, 3H), 1.36-1.27 (m, 1H), 1.05 (s, 3H). $^{13}C$ NMR (100 MHz, Acetone-$d_6$) δ 172.05, 148.15, 145.33, 141.91, 136.02, 133.19, 132.76, 129.49, 128.01, 123.21, 122.44, 121.80, 121.08, 93.29, 81.46, 69.81, 69.26, 59.88, 49.45, 37.01, 36.17, 35.99, 25.06, 22.16, 21.84, 21.17, 15.18. HRMS (ESI): m/z calcd for $C_{27}H_{31}NNaO_6(M+Na)^+$, 488.2049; found, 488.2047.

ADC-15: $R_1$=H, $R_2$=3,4,5-tri$CH_3O$—$C_6H_2$; $^1H$ NMR (400 MHz, Acetone-$d_6$) δ 7.58 (s, 1H), 7.16 (s, 2H), 6.74 (dd, J=15.7, 10.7 Hz, 1H), 6.37 (d, J=15.7 Hz, 1H), 6.20 (s, 1H), 5.55 (s, 1H), 4.69 (d, J=4.7 Hz, 1H), 4.23 (d, J=10.7 Hz, 1H), 3.93 (s, 1H), 3.90 (s, 6H), 3.80 (s, 3H), 3.46 (dd, J=18.4, 10.6 Hz, 2H), 2.55 (d, J=10.0 Hz, 1H), 2.17-2.10 (m, 1H), 2.04-1.92 (m, 1H), 1.82-1.65 (m, 3H), 1.54 (s, 3H), 1.37 (dd, J=12.2, 4.7 Hz, 1H), 1.32-1.26 (m, 1H), 1.22 (s, 3H), 0.89 (s, 3H). $^{13}C$ NMR (100 MHz, Acetone-$d_6$) δ 168.47, 153.56 (2C, overlap), 147.40, 139.48, 138.82, 136.40, 132.47, 129.25, 126.07, 122.17, 122.11, 112.97, 108.12 (2C, overlap), 80.18, 63.45, 60.51, 59.84, 55.62 (2C, overlap), 50.11, 41.96, 38.20, 36.04, 27.67, 23.20, 22.29, 21.87, 15.40. HRMS (ESI): m/z calcd for $C_{34}H_{38}NaO_7(M+Na)^+$, 533.2515; found, 533.2513.

ADC-16: $R_1$=H, $R_2$=2-furyl; $^1H$ NMR (400 MHz, DMSO-$d_6$) δ 7.87 (d, J=1.2 Hz, 1H), 7.69 (s, 1H), 6.91 (d, J=3.5 Hz, 1H), 6.68 (dd, J=3.1, 1.8 Hz, 1H), 6.58 (dd, J=15.7, 10.6 Hz, 1H), 6.39 (s, 1H), 6.31 (d, J=15.7 Hz, 1H), 5.51 (s, 1H), 5.13 (d, J=4.3 Hz, 1H), 4.31 (d, J=5.3 Hz, 1H), 3.94 (d, J=10.8 Hz, 1H), 3.45-3.39 (m, 1H), 3.26-3.19 (m, 1H), 2.49 (s, 1H), 2.02 (s, 2H), 1.69-1.49 (m, 3H), 1.47 (s, 3H), 1.26 (dd, J=10.6, 6.3 Hz, 1H), 1.22-1.13 (m, 1H), 1.08 (s, 3H), 0.80 (s, 3H). $^{13}C$ NMR (100 MHz, DMSO-$d_6$) δ 168.74, 149.47, 145.92, 145.68, 138.93, 136.13, 132.45, 126.35, 122.76, 122.35, 115.35, 113.69, 101.65, 79.36, 62.99, 60.22, 49.98, 42.12, 38.30, 36.22, 27.81, 23.71, 23.22, 22.69, 16.02. HRMS (ESI): m/z calcd for $C_{25}H_{30}NaO_5(M+Na)^+$, 433.1991; found, 433.1990.

ADC-17: $R_1$ and $R_2$ are connected to form a cyclohexyl; $^1H$ NMR (400 MHz, DMSO-$d_6$) δ 8.02 (s, 1H), 6.52 (dd, J=15.7, 10.6 Hz, 1H), 6.21 (d, J=15.7 Hz, 1H), 5.50 (s, 1H), 5.12 (s, 1H), 4.30 (s, 1H), 3.94 (d, J=10.9 Hz, 1H), 3.40 (d, J=11.1 Hz, 1H), 3.22 (dd, J=10.9, 4.1 Hz, 1H), 2.48 (d, J=11.0 Hz, 1H), 2.45-2.36 (m, 4H), 2.01 (s, 2H), 1.59 (s, 6H), 1.57-1.47 (m, 3H), 1.46 (s, 3H), 1.26 (dd, J=10.6, 6.3 Hz, 1H), 1.17 (td, J=13.1, 3.7 Hz, 1H), 1.08 (s, 3H), 0.79 (s, 3H). $^{13}C$ NMR (100 MHz, DMSO-$d_6$) δ 169.15, 142.54, 137.70, 132.59, 132.57, 130.84, 126.33, 122.65, 122.33, 79.37, 62.99, 60.16, 49.97, 42.11, 38.28, 36.11, 28.94, 28.72, 28.16, 27.82, 27.49, 26.08, 23.71, 23.22, 22.67, 15.99. HRMS (ESI): m/z calcd for $C_{26}H_{36}NaO_4(M+Na)^+$, 435.2511; found, 435.2516.

To investigate the application effect of the compounds as an active ingredient of anti-fibrotic drugs, human hepatic stellate cells LX-2, as a material, are used to determine the inhibitory effect of the compounds on cell migration and activation, and used in in vitro assays to quantitatively evaluate the anti-hepatic fibrosis activity of the compounds. Human type II alveolar epithelial cells A549 are used to measure the inhibitory effect of the compounds on epithelial-mesenchymal transition (EMT) of A549 cells induced by transforming growth factor beta-1 (TGF-$β_1$), and used in in vitro assays to quantitatively evaluate the anti-pulmonary fibrosis activity of the compounds. Human renal proximal tubule epithelial cells HK-2 are used to measure the inhibitory effect of the compounds on TGF-$β_1$-induced EMT of HK-2 cells, and used in in vitro assays to quantitatively evaluate the anti-renal fibrosis activity of the compounds. Primary human cardiac fibroblasts HCFB are used to measure the inhibitory effect of the compounds on the HCFB migration induced by angiotensin II (Ang II), and develop in vitro assays to quantitatively evaluate the anti-myocardial fibrosis activity of the compounds. Also, the disclosure studies the in vivo anti-fibrotic activity of the compounds by using a model of common bile duct ligation (BDL) in mice, a model of silica-induced pulmonary fibrosis in mice, a model of unilateral ureteral ligation in mice.

The cis and trans forms of the compounds have anti-fibrotic potential for major organs of human body. The compounds or various prodrugs thereof as medicinally effective ingredients may be employed alone, or in combination with one or more other drugs, followed by addition of a pharmaceutically acceptable auxiliary and/or additives by using conventional pharmaceutical methods and processing requirements. The drug products are provided as oral pills, solution for injections, or other dosage forms. The compounds are, preferably, as anti-fibrotic drugs for prevention or treatment of major organs or tissues such as liver, lung, kidney, heart, etc. The oral dosage forms include, but not limited to, tablet, pill, capsule, granule, and syrup forms; the injectable dosage forms include, but not limited to, injection and freeze-dried powder injection.

The following advantages are associated with the compounds of the disclosure: the screening process is used to determine that the above compounds have anti-fibrotic activity. The experiments comparing the compounds disclosed herein to the parent compound andrographolide (AD) suggest that the compounds of the disclosure have a more significant anti-fibrotic effect on the liver, lung, kidney, and myocardium over AD. Therefore, the use of the compounds as active ingredient for preparing various anti-fibrotic drugs in human body provides new opportunity to treat and prevent the diseases associated with fibrosis. The disclosure further broadens possible range of drug options for fibrotic disease and offers the prospect for anti-fibrosis drug development.

BRIEF DESCRIPTION OF DRAWINGS

In FIG. 1A, the representative compounds refer to ADY and derivatives thereof, where, 1. AD; 2. ADY; 3. ADY-1; 4. ADY-2; 5. ADY-3; 6. ADY-4; 7. ADY-5; 8. ADY-6; 9. ADY-7; 10. ADY-8; 11. ADY-9; 12. ADY-10; 13. ADY-11; 14. ADY-12; 15. ADY-13; 16. ADY-14; 17. ADY-15; 18. ADY-16; 19. ADY-17. In FIG. 1B, the representative compounds refer to ADC and derivatives thereof, where, 1. AD; 2. ADC; 3. ADC-1; 4. ADC-2; 5. ADC-3; 6. ADC-4; 7. ADC-5; 8. ADC-6; 9. ADC-7; 10. ADC-8; 11. ADC-9; 12. ADC-10; 13. ADC-11; 14. ADC-12; 15. ADC-13; 16. ADC-14; 17. ADC-15; 18. ADC-16; 19. ADC-17;

In FIG. 2A, the representative compounds refer to ADY and derivatives thereof, where, 1. AD; 2. ADY; 3. ADY-1; 4. ADY-2; 5. ADY-3; 6. ADY-4; 7. ADY-5; 8. ADY-6; 9. ADY-7; 10. ADY-8; 11. ADY-9; 12. ADY-10; 13. ADY-11; 14. ADY-12; 15. ADY-13; 16. ADY-14; 17. ADY-15. In FIG. 2B, the representative compounds refer to ADC and derivatives thereof, where, 1. AD; 2. ADC; 3. ADC-1; 4. ADC-2; 5. ADC-3; 6. ADC-4; 7. ADC-5; 8. ADC-6; 9. ADC-7; 10. ADC-8; 11. ADC-9; 12. ADC-10; 13. ADC-11; 14. ADC-12; 15. ADC-13; 16. ADC-14; 17. ADC-15; 18. ADC-16; 19. ADC-17;

In FIG. 3A, the representative compounds refer to ADY and derivatives thereof, where the concentration of ADY-10 and ADY-11 is 3.00 µM, and other compounds are 30.00 µM; and where, 1. AD; 2. ADY; 3. ADY-1; 4. ADY-2; 5. ADY-3; 6. ADY-4; 7. ADY-5; 8. ADY-6; 9. ADY-7; 10. ADY-8; 11. ADY-9; 12. ADY-10; 13. ADY-11; 14. ADY-12; 15. ADY-13; 16. ADY-14; 17. ADY-15; 18. ADY-16; 19. ADY-17. In FIG. 3B, the representative compounds refer to ADC and derivatives thereof, where the concentration of ADC-9 is 3.00 µM, and other compounds are 30.00 µM; and where, 1. AD; 2. ADC; 3. ADC-1; 4. ADC-2; 5. ADC-3; 6. ADC-4; 7. ADC-5; 8. ADC-6; 9. ADC-7; 10. ADC-8; 11. ADC-9; 12. ADC-10; 13. ADC-11; 14. ADC-12; 15. ADC-13; 16. ADC-14; 17. ADC-15; 18. ADC-16; 19. ADC-17;

In FIG. 4A, 1. Control group; 2. TGF-$\beta_1$ (5 ng/mL); 3. TGF-$\beta_1$+AD; 4. TGF-$\beta_1$+ADY; 5. TGF-$\beta_1$+ADY-1; 6. TGF-$\beta_1$+ADY-2; 7. TGF-$\beta_1$+ADY-3; 8. TGF-$\beta_1$+ADY-4; 9. TGF-$\beta_1$+ADY-5; 10. TGF-$\beta_1$+ADY-6; 11. TGF-$\beta_1$+ADY-7; 12. TGF-$\beta_1$+ADY-8; 13. TGF-$\beta_1$+ADY-9; 14. TGF-$\beta_1$+ADY-10; 15. TGF-$\beta_1$+ADY-11; 16. TGF-$\beta_1$+ADY-12; 17. TGF-$\beta_1$+ADY-13; 18. TGF-$\beta_1$+ADY-14; 19. TGF-$\beta_1$+ADY-15; 20. TGF-$\beta_1$+ADY-16; 21. TGF-$\beta_1$+ADY-17. The representative compounds in FIG. 4B refer to ADC and derivatives thereof, where the compounds AD, ADC-1, ADC-5, ADC-7, ADC-8, ADC-9, ADC-13, ADC-14 and ADC-15 have a low dose of 1.25 µM and a high dose of 2.50 µM. Other compounds have a low dose of 0.63 µM and a high dose of 1.25 µM. In FIG. 4B: 1. Control group; 2. TGF-$\beta_1$; 3. TGF-$\beta_1$+AD; 4. TGF-$\beta_1$+ADC; 5. TGF-$\beta_1$+ADC-1; 6. TGF-$\beta_1$+ADC-2; 7. TGF-$\beta_1$+ADC-3; 8. TGF-$\beta_1$+ADC-4; 9. TGF $\beta_1$+ADC-5; 10. TGF-$\beta_1$+ADC-6; 11. TGF-$\beta_1$+ADC-7; 12. TGF-$\beta_1$+ADC-8; 13. TGF-$\beta_1$+ADC-9; 14. TGF-$\beta_1$+ADC-10; 15. TGF-$\beta_1$+ADC-11; 16. TGF-$\beta_1$+ADC-12; 17. TGF-$\beta_1$+ADC-13; 18. TGF-$\beta_1$+ADC-14; 19. TGF-$\beta_1$+ADC-15; 20. TGF-$\beta_1$+ADC-16; 21. TGF-$\beta_1$+ADC-17;

In FIG. 5A: 1. TGF-$\beta_1$ (5 ng/mL)+AD; 2. TGF-$\beta_1$+ADY; 3. TGF-$\beta_1$+ADY-1; 4. TGF-$\beta_1$+ADY-2; 5. TGF-$\beta_1$+ADY-3; 6. TGF-$\beta_1$+ADY-4; 7. TGF-$\beta_1$+ADY-5; 8. TGF-$\beta_1$+ADY-6; 9. TGF-$\beta_1$+ADY-7; 10. TGF-$\beta_1$+ADY-8; 11. TGF-$\beta_1$+ADY-9; 12. TGF-$\beta_1$+ADY-10; 13. TGF-$\beta_1$+ADY-11; 14 TGF-$\beta_1$+ADY-12; 15. TGF-$\beta_1$+ADY-13 16. TGF-$\beta_1$+ADY-14; 17. TGF-$\beta_1$+ADY-15; 18. TGF-$\beta_1$+ADY-16; 19. TGF-$\beta_1$+ADY-17. The representative compounds in FIG. 5B refer to ADC and derivatives thereof, where the compounds AD, ADC-8, ADC-11, ADC-16 and ADC-17 each has a low dose of 0.31 µM and a high dose of 0.63 µM. Other compounds have a low dose of 0.08 µM and a high dose of 0.16 µM. In FIG. 5B: 1. TGF-$\beta_1$ (5 ng/mL)+AD; 2. TGF-$\beta_1$+ADC; 3. TGF-$\beta_1$+ADC-1; 4. TGF- β$_1$+ADC-2; 5. TGF-β$_1$+ADC-3; 6. TGF-β$_1$+ADC-4; 7. TGF-β$_1$+ADC-5; 8. TGF-β$_1$+ADC-6; 9. TGF-β$_1$+ADC-7; 10. TGF-β$_1$+ADYC-8; 11. TGF-β$_1$+ADC-9; 12. TGF-β$_1$+ADC-10; 13. TGF-β$_1$+ADC-11; 14 TGF-β$_1$+ADC-12; 15. TGF-β$_1$+ADC-13; 16. TGF-β$_1$+ADC-15; 17. TGF-β$_1$+ADC-16; 18. TGF-β$_1$+ADC-17;

In FIG. 6A: 1. AD; 2. ADY; 3. ADY-1; 4. ADY-2; 5. ADY-3; 6. ADY-4; 7. ADY-5; 8. ADY-6; 9. ADY-7; 10. ADY-8; 11. ADY-9; 12. ADY-10; 13. ADY-11; 14. ADY-12; 15. ADY-13; 16. ADY-14; 17. ADY-15; where in the concentration of ADY-2, ADY-5, ADY-6 and ADY-8 is 15.00 μM, the ADY-11 is 3.00 μM, and the other compounds each is 30.00 μM. The representative compounds in FIG. 6B refer to ADC and derivatives thereof. 30.00 μM AD shows a lower inhibitory activity against the cell proliferation then the equivalent dose of ADC-5, ADC-6, ADC-11 and ADC-12. In FIG. 6B: 1. AD; 2. ADC; 3. ADC-1; 4. ADC-2; 5. ADC-3; 6. ADC-4; 7. ADC-5; 8. ADC-6; 9. ADC-7; 10. ADC-8; 11. ADC-9; 12. ADC-10; 13. ADC-11; 14. ADC-12; 15. ADC-13; 16. ADC-14; 17. ADC-15; 18. ADC-16; 19. ADC-17; where the concentration of ADC-5 and ADC-6 is 3.00 μM, and the other compounds are 30.00 μM;

In FIG. 7A, 1. Control group; 2. TGF-β$_1$; 3. TGF-β$_1$+ADY-4 (0.31 μM); 4. TGF-β$_1$+ADY-5 (0.08 μM); 5. TGF-β$_1$+ADY-6 (0.63 μM); 6. TGF-β$_1$+ADY-9 (0.08 μM); 7. TGF-β$_1$+ADY-11 (0.08 μM); 8. TGF β$_1$+AD (1.25 μM). The representative compounds in FIG. 7B refer to ADC and derivatives thereof. In FIG. 7B, 1. Control group; 2. TGF-β$_1$; 3. TGF-β$_1$+AD (1.25 μM); 4. TGF-β$_1$+ADC (0.63 μM); 5. TGF-β$_1$+ADC-2 (0.63 μM); 6. TGF-β$_1$+ADC-12 (0.31 μM); 7. TGF-β$_1$+ADC-14 (0.08 μM); 8. TGF-β$_1$+ADC-15 (0.08 μM);

In FIG. 8A: 1. TGF-β$_1$ (5 ng/mL)+AD; 2. TGF-β$_1$+ADY; 3. TGF-β$_1$+ADY-1; 4. TGF-β$_1$+ADY-2; 5. TGF-β$_1$+ADY-3; 6. TGF-β$_1$+ADY-4; 7. TGF-β$_1$+ADY-5; 8. TGF-β$_1$+ADY-6; 9. TGF-β$_1$+ADY-7; 10. TGF-β$_1$+ADY-8; 11. TGF-β$_1$+ADY-9; 12. TGF-β$_1$+ADY-10; 13. TGF-β$_1$+ADY-11; 14 TGF-β$_1$+ADY-12; 15. TGF-β$_1$+ADY-13; 16. TGF β$_1$+ADY-14; 17. TGF-β$_1$+ADY-15; 18. TGF-β$_1$+ADY-16; 19. TGF-β$_1$+ADY-17. The representative compounds in FIG. 8B refer to ADC and derivatives thereof. The compound AD, ADC-5, ADC-11, ADC-13 and ADC-17 each has a low dose of 0.08 μM and a high dose of 0.16 Other compounds each have a low dose of 0.04 μM and a high dose of 0.08 In FIG. 8B: 1. TGF-β$_1$ (5 ng/mL)+AD; 2. TGF-β$_1$+ADC; 3. TGF-β$_1$+ADC-1; 4. TGF-β$_1$+ADC-2; 5. TGF-β$_1$+ADC-3; 6. TGF-β$_1$+ADC-4; 7. TGF-β$_1$+ADC-5; 8. TGF-β$_1$+ADC-6; 9. TGF-β$_1$+ADC-7; 10. TGF-β$_1$+ADC-8; 11. TGF-β$_1$+ADC-9; 12. TGF-β$_1$+ADC-10; 13. TGF-β$_1$+ADC-11; 14. TGF-β$_1$+ADC-12; 15. TGF-β$_1$+ADC-13; 16. TGF-β$_1$+ADC-15; 17. TGF-β$_1$+ADC-16; 18. TGF-β$_1$+ADC-17;

In FIG. 11A: 1. Model group; 2. AD (15 mg/kg; intragastric administration (ig)); 3. AD (40 mg/kg; ig); 4. ADY (15 mg/kg; ig); 5. ADY-6 (15 mg/kg; ig); 6. ADY-8 (15 mg/kg; ig); 7. ADY-12 (15 mg/kg; ig); 8. ADY-7 (15 mg/kg; ig); where the representative compound in FIG. 11B is ADC and derivatives thereof. In FIG. 11B: 1. Model group; 2. AD (15 mg/kg; ig); 3. AD (40 mg/kg; ig); 4. ADC (15 mg/kg; ig); 5. ADC-2 (15 mg/kg; ig); 6. ADC-4 (40 mg/kg; ig); 7. ADC-10 (15 mg/kg; ig); 8. ADC-12 (15 mg/kg; ig); 9. ADC-15 (40 mg/kg; ig);

In FIG. 12A: 1. Sham-operated control group; 2. Model group; 3. AD (15 mg/kg; ig); 4. ADY (15 mg/kg; ig); 5. ADY-6 (15 mg/kg; ig); 6. ADY-8 (15 mg/kg; ig); 7. ADY-12 (15 mg/kg; ig); 8. ADY-7 (15 mg/kg; ig); where the representative compound in FIG. 12B is ADC and derivatives thereof, in FIG. 12B: 1. Sham operation; 2. Model; 3. AD (15 mg/kg; ig); 4. ADC (15 mg/kg; ig); 5. ADC-2 (15 mg/kg; ig); 6. ADC-4 (40 mg/kg; ig); 7. ADC-10 (15 mg/kg; ig); 8. ADC-12 (15 mg/kg; ig); 9. ADC-15 (40 mg/kg; ig);

Figure 13A:
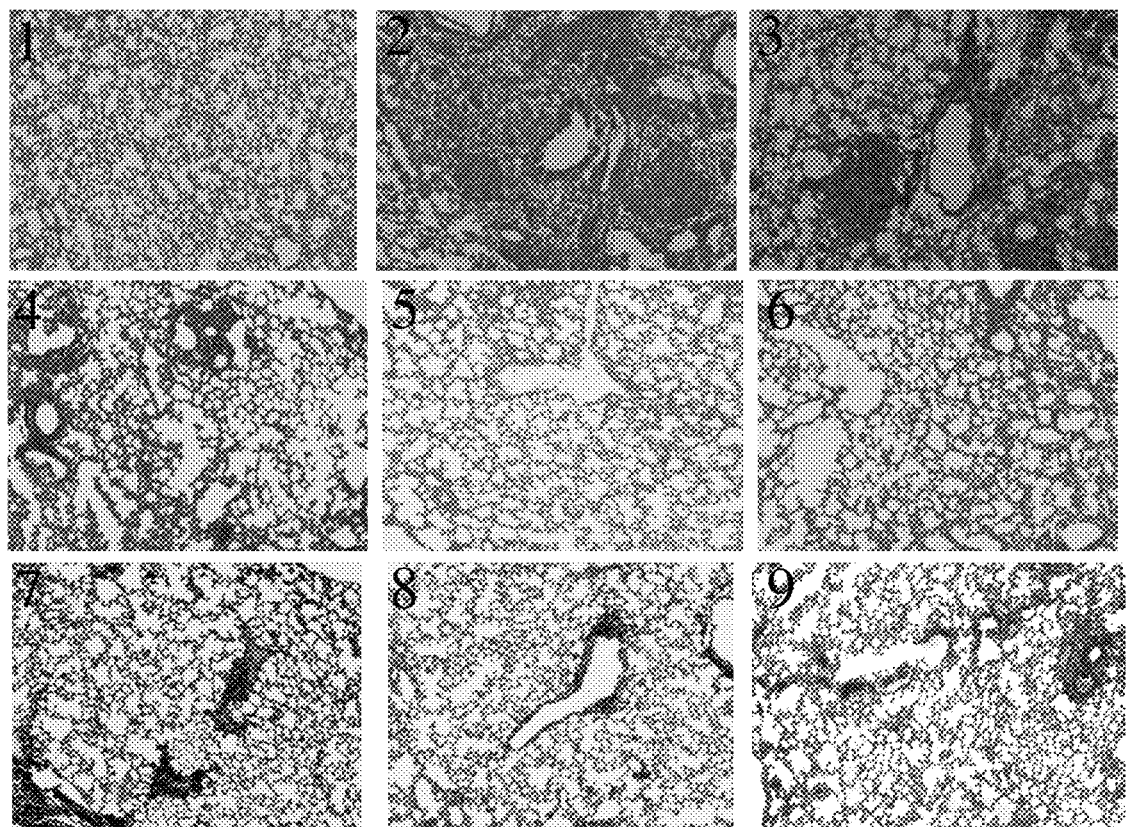
Figure 13B:
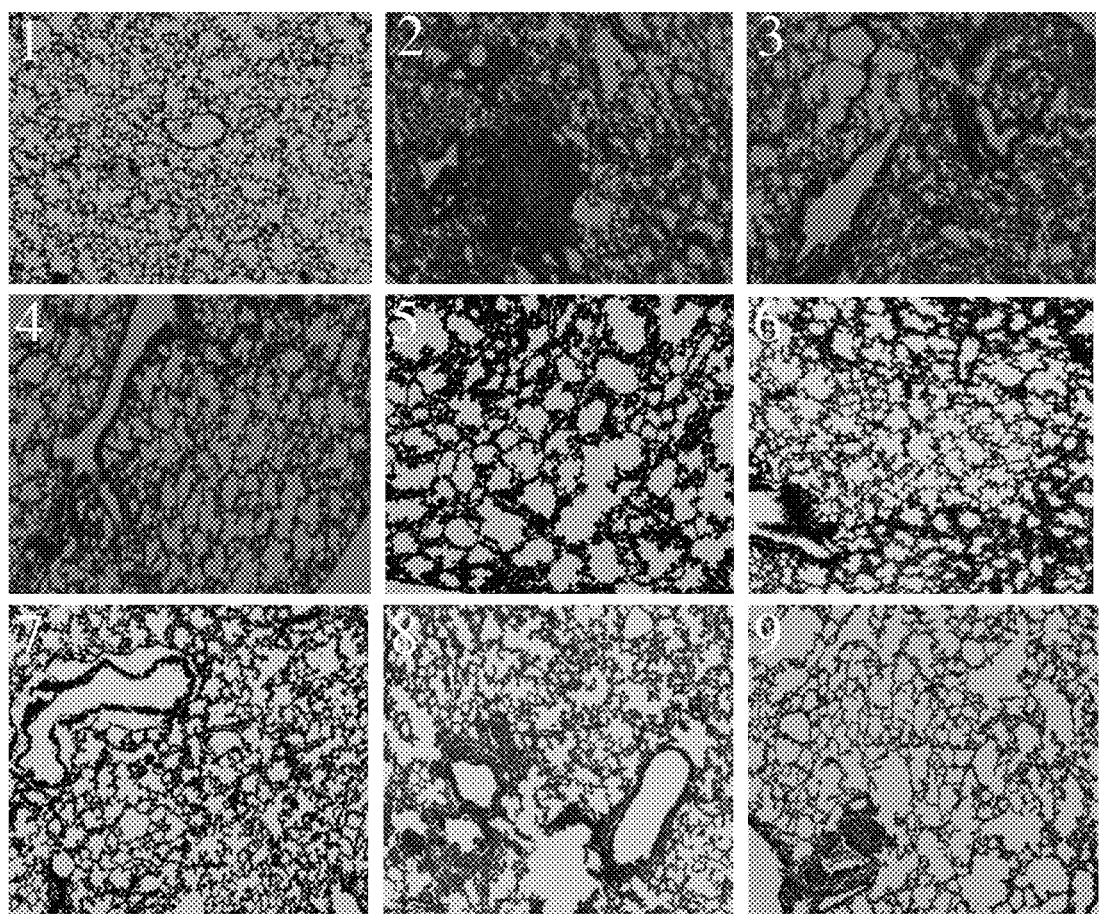
Figure 14A:
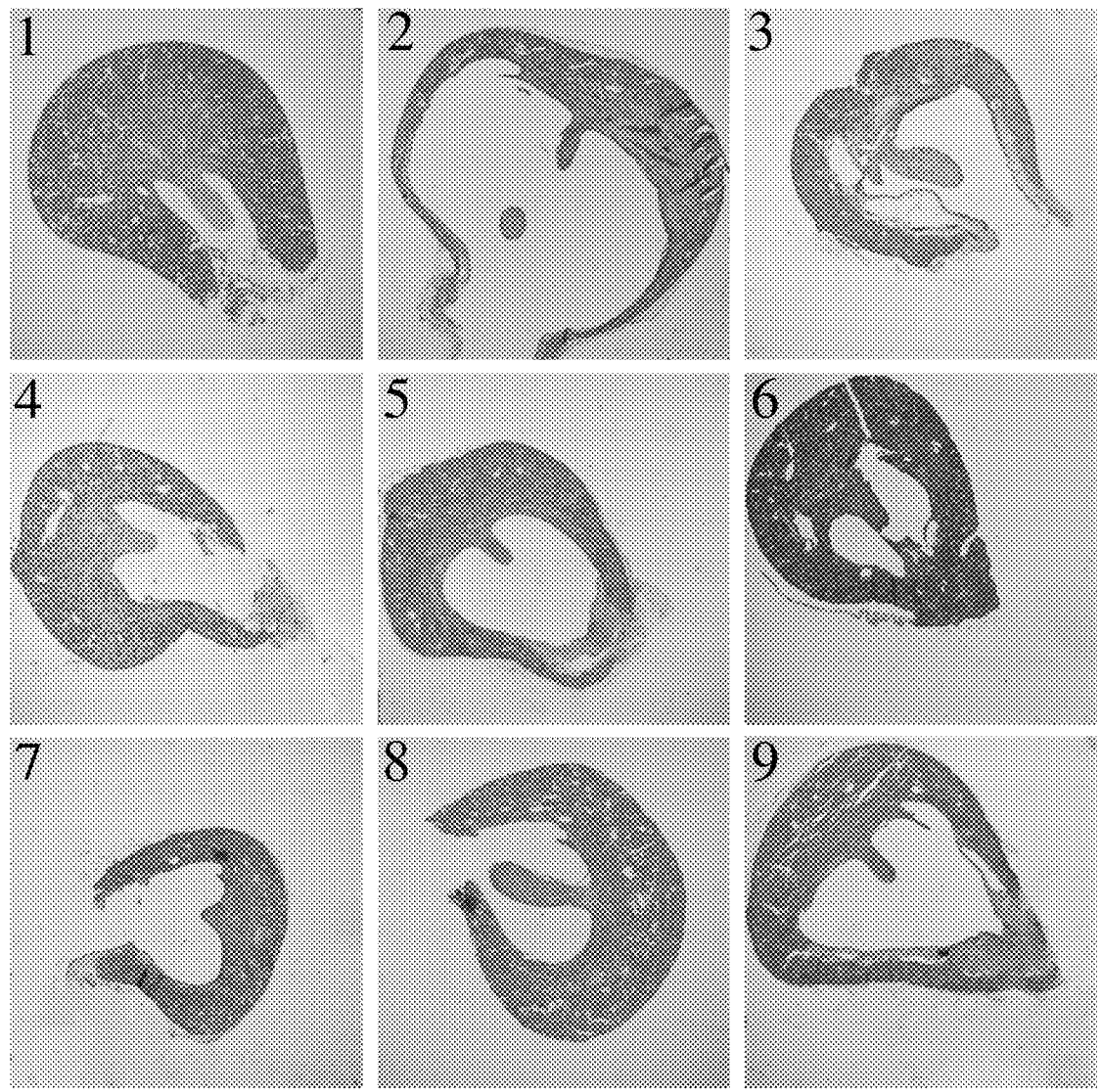
Figure 14B:
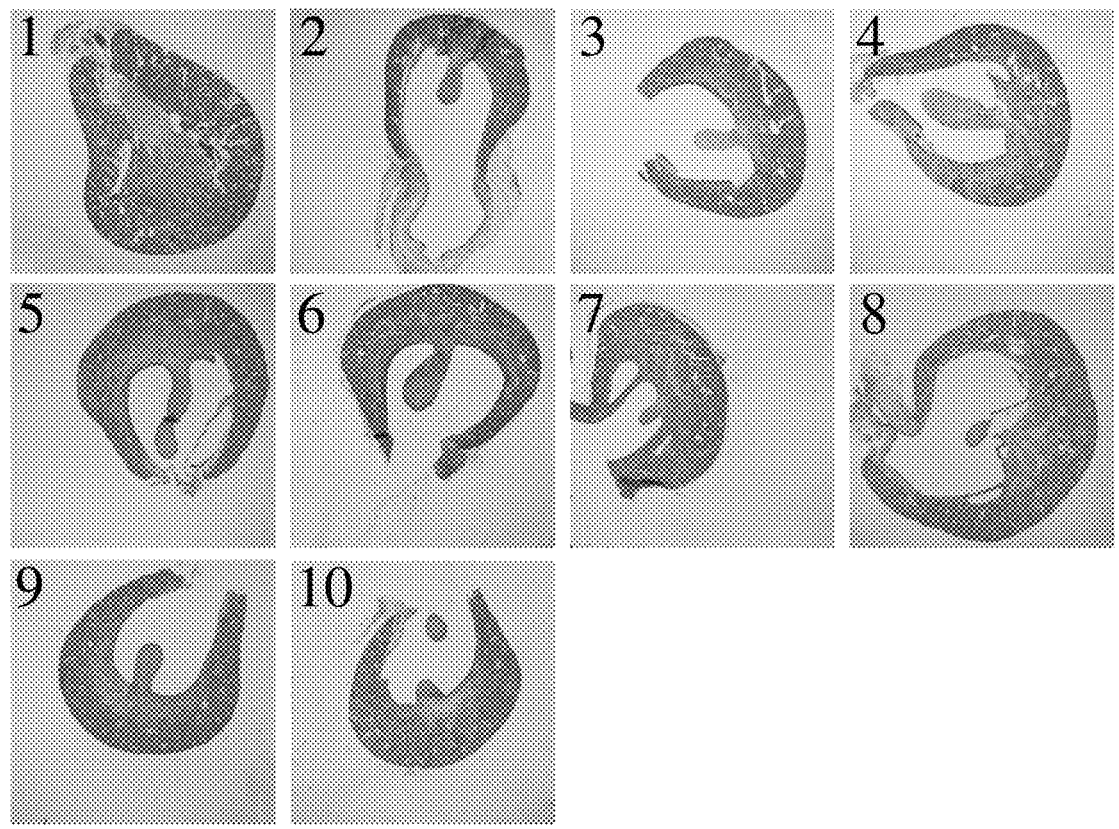
Figure 15A:
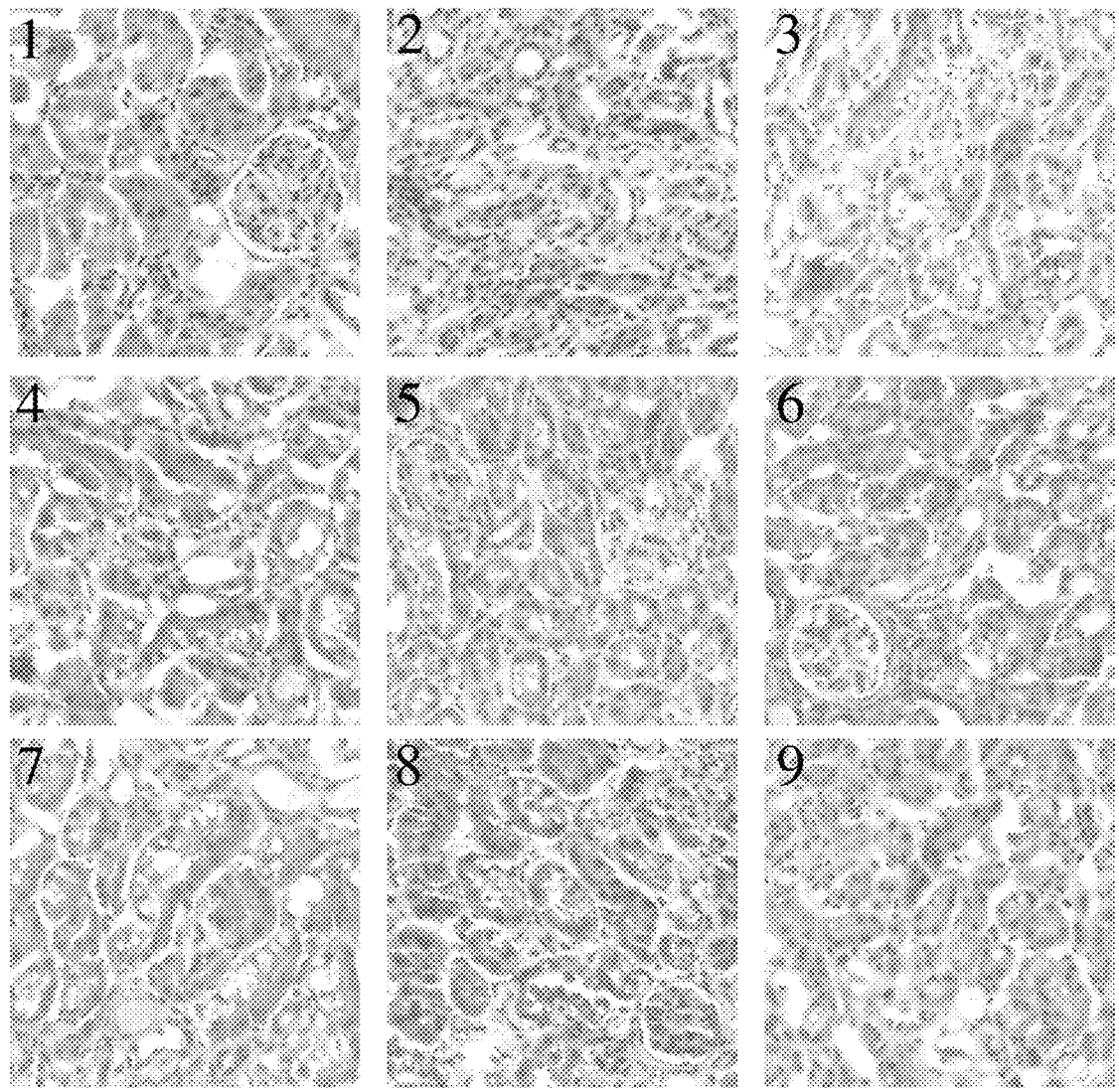
Figure 15B:
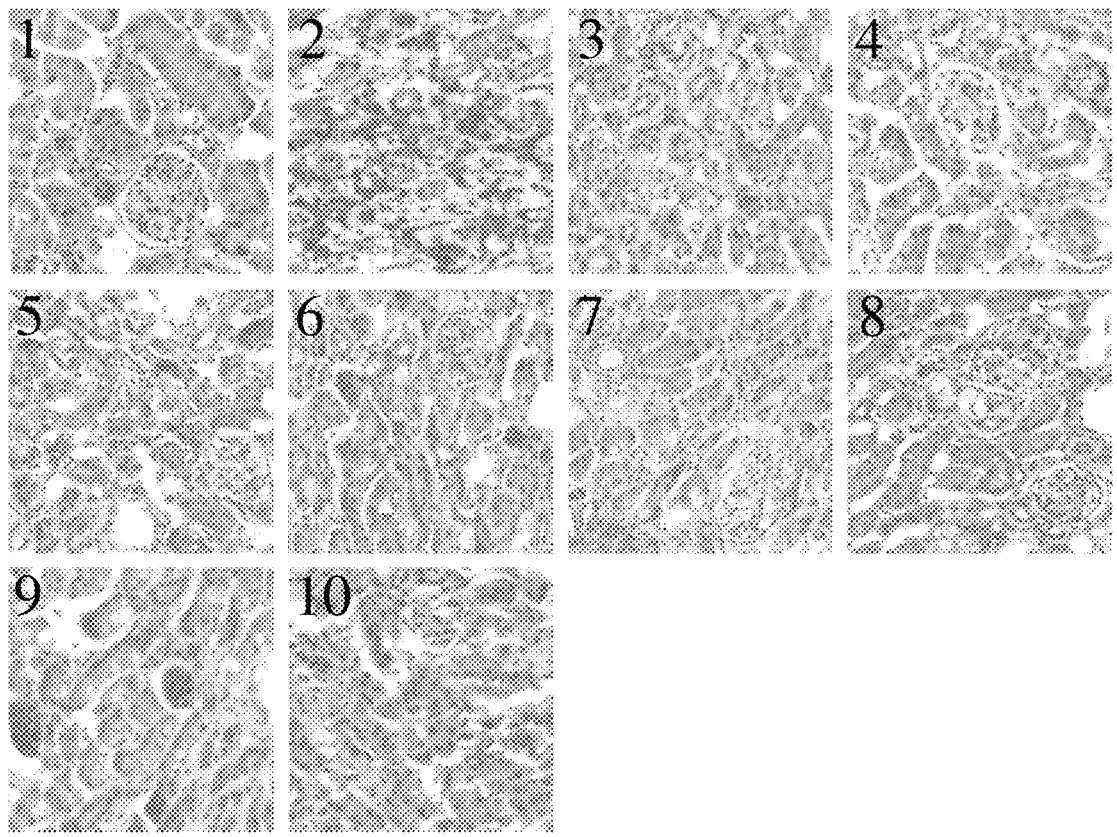
Figure 16A:
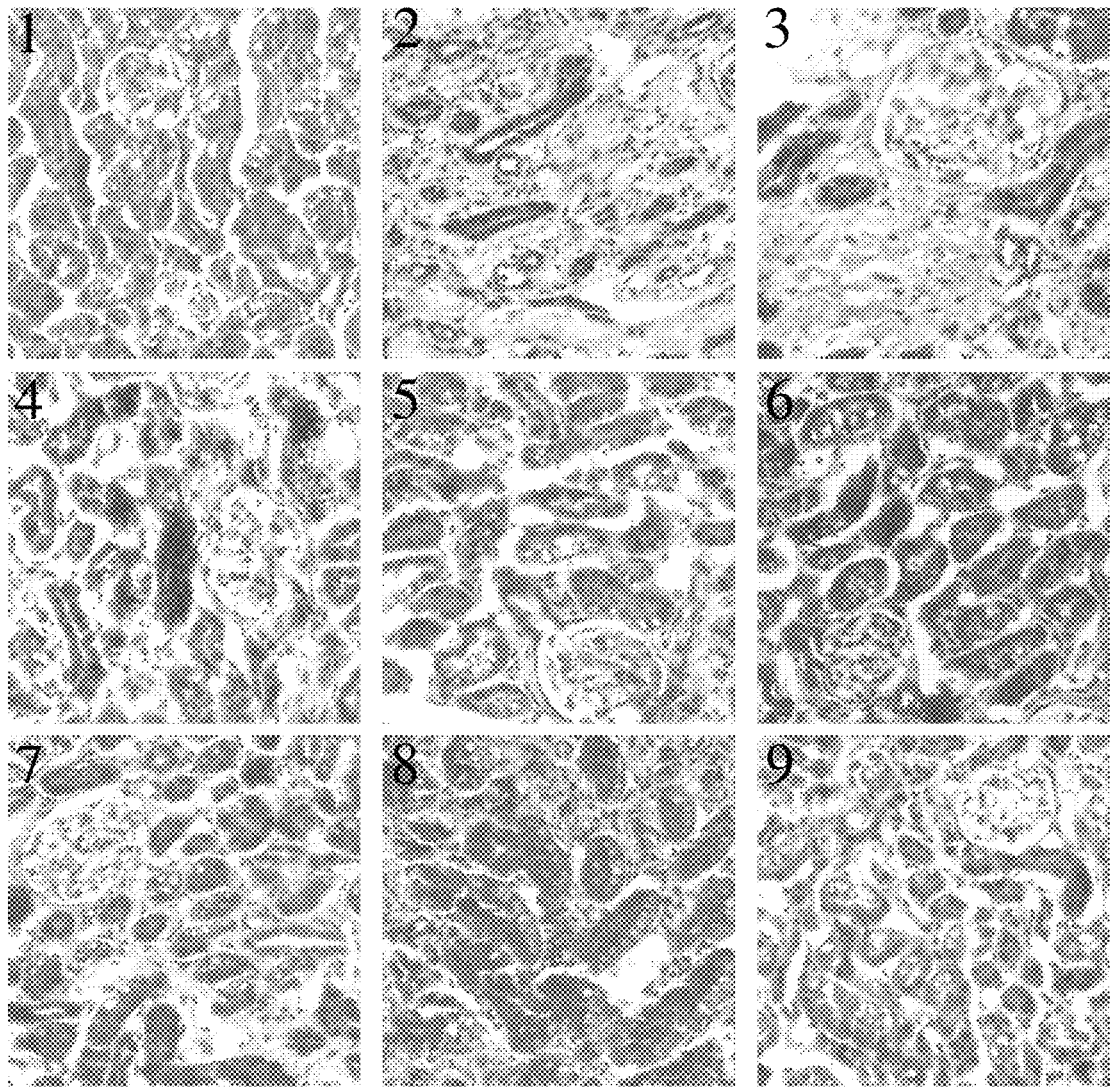
Figure 16B:
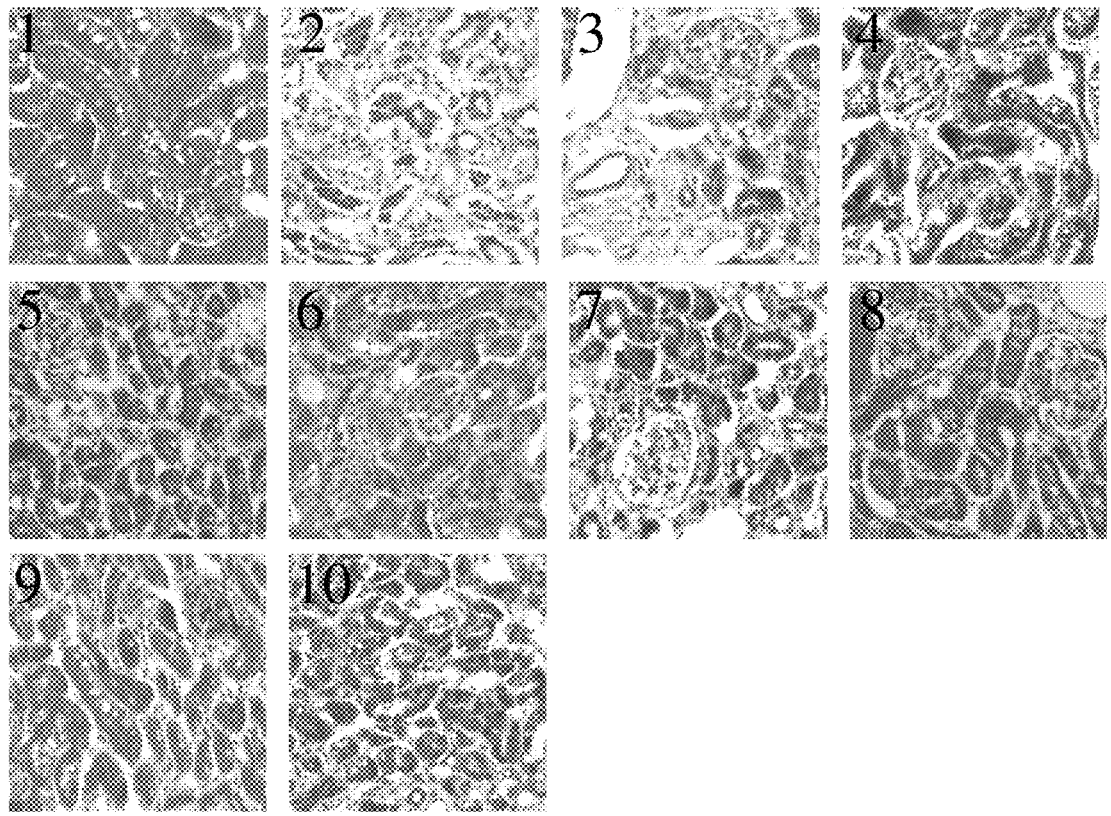

FIGS. 13A-13B show the effect of AD and compound of the disclosure on improvement in the silicon-induced pulmonary fibrosis in KM mice (Masson stain; micrograph, ×100 times). The representative compounds in FIG. 13A refer to ADY and derivatives thereof. In FIG. 13A: 1. Sham-operated control group; 2. Model group; 3. AD (120 mg/kg; ig); 4. ADY (40 mg/kg; ig); 5. ADY-6 (120 mg/kg; ig); 6. ADY-8 (120 mg/kg; ig); 7. ADY-7 (120 mg/kg; ig); 8. ADY-4 (40 mg/kg; ig); 9. ADY-12 (120 mg/kg; ig). The representative compounds in FIG. 13B refer to ADC and derivatives thereof. In FIG. 13B: 1. Sham-operated control group; 2. Model group; 3. AD (120 mg/kg; ig); 4. ADC (120 mg/kg; ig); 5. ADC-2 (40 mg/kg; ig); 6. ADC-4 (120 mg/kg; ig); 7. ADC-10 (40 mg/kg; ig); 8. ADC-12 (120 mg/kg; ig); 9. ADC-15 (40 mg/kg; ig);

FIGS. 14A-14B show the effect of AD and compound of the disclosure on improvement in the renal fibrosis in KM mice induced by unilateral ureteral ligation (HE staining; micrograph, ×40 times). The representative compounds in FIG. 14A refer to ADY and derivatives thereof. In FIG. 14A: 1. Sham-operated control group; 2. Model group; 3. AD (70 mg/kg; ig); 4. ADY (70 mg/kg; ig); 5. ADY-4 (25 mg/kg; ig); 6. ADY-6 (25 mg/kg; ig); 7. ADY-7 (25 mg/kg; ig); 8. ADY-8 (25 mg/kg; ig) 9. ADY-12 (25 mg/kg; ig). The representative compounds in FIG. 14B refer to ADC and derivatives thereof. In FIG. 14B: 1. Sham-operated control group; 2. Model group; 3. AD (70 mg/kg; ig); 4. ADC (70 mg/kg; ig); 5. ADC-2 (25 mg/kg; ig); 6. ADC-4 (70 mg/kg; ig); 7. ADC-10 (25 mg/kg; ig); 8. ADC-12 (25 mg/kg; ig)); 9. ADC-15 (25 mg/kg; ig); 10. ADC-16 (25 mg/kg; ig);

FIGS. 15A-15B show the effect of AD and compound of the disclosure on improvement in the renal fibrosis in KM mice induced by unilateral ureteral ligation (HE staining; micrograph, ×100 times). The representative compounds in FIG. 15A refer to ADY and derivatives thereof. In FIG. 15A: 1. Sham-operated control group; 2. Model group; 3. AD (70 mg/kg; ig); 4. ADY (70 mg/kg; ig); 5. ADY-4 (25 mg/kg; ig); 6. ADY-6 (25 mg/kg; ig); 7. ADY-7 (25 mg/kg; ig); 8. ADY-8 (25 mg/kg; ig) 9. ADY-12 (25 mg/kg; ig). The representative compounds in FIG. 15B refer to ADC and derivatives thereof. In FIG. 15B: 1. Sham-operated control group; 2. Model group; 3. AD (70 mg/kg; ig); 4. ADC (70 mg/kg; ig); 5. ADC-2 (25 mg/kg; ig); 6. ADC-4 (70 mg/kg; ig); 7. ADC-10 (25 mg/kg; ig); 8. ADC-12 (25 mg/kg; ig)); 9. ADC-15 (25 mg/kg; ig); 10. ADC-16 (25 mg/kg; ig);

FIGS. 16A-16B show the effect of AD and compound of the disclosure on improvement in the renal fibrosis in KM mice induced by unilateral ureteral ligation (Masson staining; micrograph, ×100 times). The representative compounds in FIG. 16A refer to ADY and derivatives thereof. In FIG. 16A: 1. Sham-operated control group; 2. Model group; 3. AD (70 mg/kg; ig); 4. ADY (70 mg/kg; ig); 5. ADY-4 (25 mg/kg; ig); 6. ADY-6 (25 mg/kg; ig); 7. ADY-7 (25 mg/kg; ig); 8. ADY-8 (25 mg/kg; ig) 9. ADY-12 (25 mg/kg; ig). The representative compounds in FIG. 16B refer to ADC and derivatives thereof. In FIG. 16B: 1. Sham-operated control group; 2. Model group; 3. AD (70 mg/kg; ig); 4. ADC (70 mg/kg; ig); 5. ADC-2 (25 mg/kg; ig); 6. ADC-4 (70 mg/kg; ig); 7. ADC-10 (25 mg/kg; ig); 8. ADC-12 (25 mg/kg; ig)); 9. ADC-15 (25 mg/kg; ig); 10. ADC-16 (25 mg/kg; ig).

DETAILED DESCRIPTION

To further illustrate the disclosure, embodiments detailing 14-deoxy-11,12-didehydro-8,12-epoxy andrographolide, 14-deoxy-11,12-didehydro-7,8-ene-andrographolide, and 15-substituted derivatives thereof are described below. It should be noted that the following embodiments are intended to describe and not to limit the disclosure.

EXAMPLE 1

The compounds of the disclosure inhibit migration of human hepatic stellate cells LX-2.

Hepatic stellate cells migrate to the inflammatory site of damaged liver tissue under the stimulation of various inflammatory mediators and growth factors, and further proliferate and activate, in which the synthesis of extracellular matrix (ECM) components such as collagen is crucial to the development of hepatic fibrosis. The compounds of the disclosure were compared with andrographolide (AD) to evaluate the anti-hepatic fibrosis activity of the compounds by an in vitro wound healing assay.

1. Cell Culture and Test Compounds

LX-2 cells (provided by Beijing Beina Chuanglian Biotechnology Co. Ltd.) were cultured in a RPMI1640 medium containing 10% (V/V) fetal bovine serum (FBS), 100 μg/mL streptomycin, and 100 IU/mL penicillin, followed by incubation in a 37° C. incubator with a saturated humidity and 5% $CO_2$. Andrographolide (AD) was produced by Sichuan Shifang Jinxin Biotechnology Co., Ltd. (Batch No.: 120822), with a purity greater than 99%; the compounds of the disclosure were synthesized in a laboratory, with a purity greater than 99%.

2. In Vitro Cytotoxicity MTT Assay

Figure 1A:
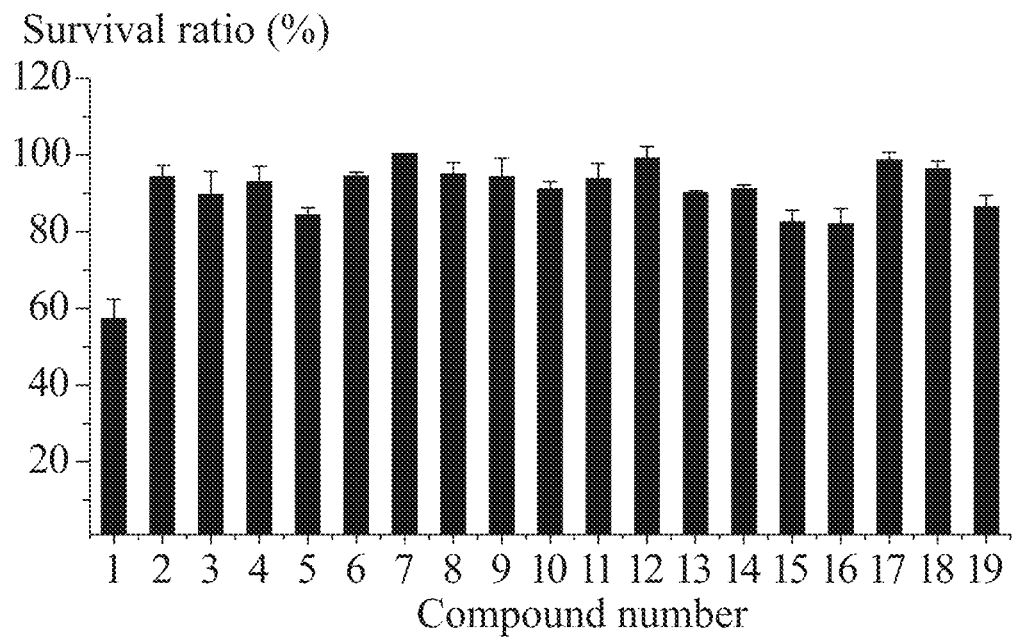
FIGS. 1A-1B show the effect of AD and the representative compounds (30.00 µM) of the disclosure on the viability of human hepatic stellate cells LX-2.
Figure 1B:
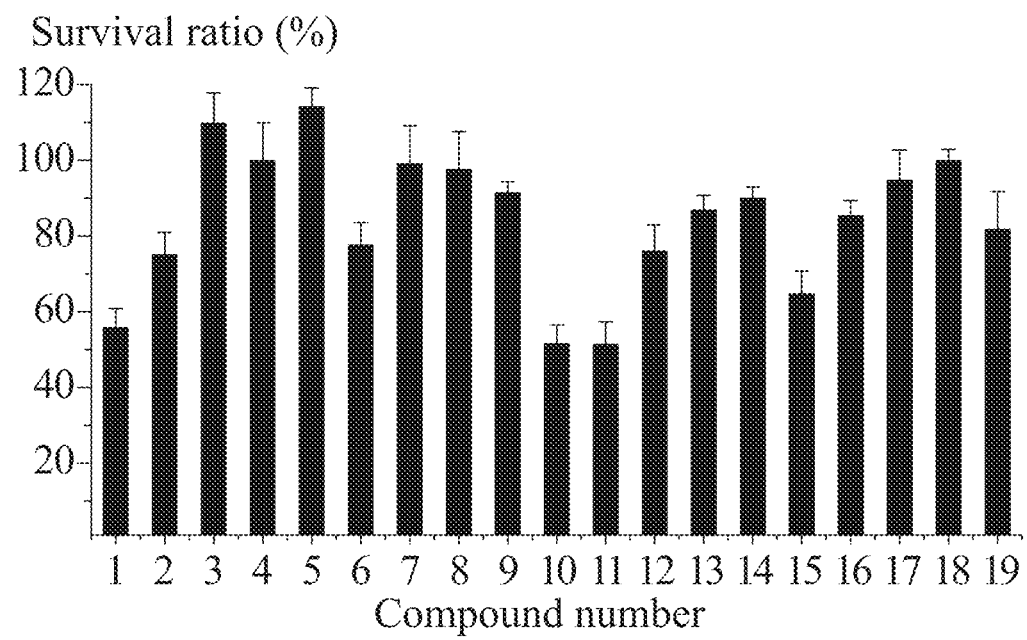

LX-2 cells in the logarithmic growth phase were digested with 0.25% (W/V) trypsin, diluted into $3.5 \times 10^4$ cell/mL cell suspension with RPMI1640 medium containing 10% (V/V) FBS, and transferred into a 96-well plate for 200 μL per well. After incubation in the 37° C. incubator with 5% $CO_2$ for 24 hours, the medium comprising different concentration of drugs were added to the wells. Under these conditions, the maximum final drug concentration in the assay was 30.00 μM. The experiment was performed in triplicate. After further incubation for 48 hours, MTT (5 mg/mL) was added to the 96-well plate for 20 μL per well, followed by incubation for 4 hours and removal of the supernatant. 150 μL of dimethyl sulfoxide (DMSO) was added to each well and shaken for 10 min. Absorbance of each well was measured at 570 nm against a reference wavelength of 450 nm using a microplate reader. After exposure to the test compounds, the relative survival rate of cell was calculated using the following formula: survival rate (%)= $(OD_{administration/570} - OD_{administration/450})/(OD_{control/570} - OD_{control/450}) \times 100\%$, and the survival rates from the four measurements were combined to obtain an average survival rate for each group, as shown in FIGS. 1A and 1B.

3. In Vitro Wound Healing Assay to Detect the Effect of Test Compounds on Migration of LX-2 Cells.

Figure 2A:
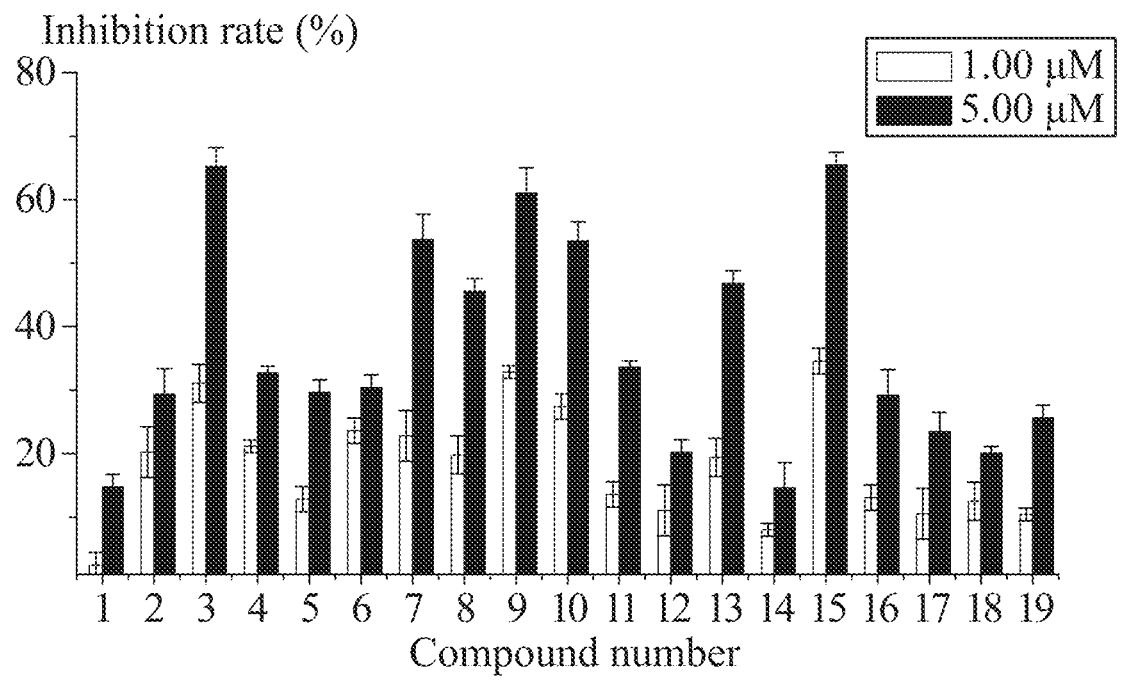
FIGS. 2A-2B show the results of inhibition of AD and the representative compound of the disclosure (5.00 µM and 1.00 µM) on the migration in human hepatic stellate cells LX-2.
Figure 2B:
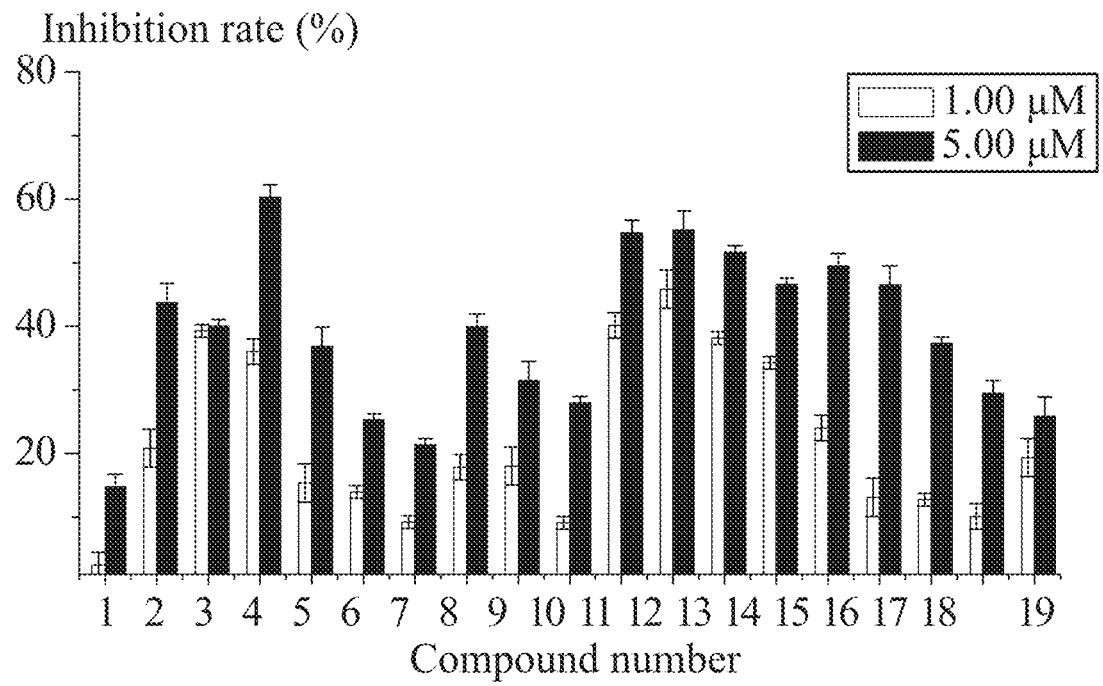

LX-2 cells in logarithmic growth phase were digested with 0.25% (W/V) trypsin, diluted into $1.0 \times 10^5$/mL cell suspension with a RPMI1640 medium containing 10% (V/V) FBS, and transferred into a 96-well plate for 200 μL per well. The cells were cultured as monolayer for 12 hours and grew to confluence, followed by removal of the medium. The medium with 0.5% serum was added and re-synchronized for 12 h. A scratch was created through the cell monolayer, and the monolayer was washed 2 times with PBS to remove floating cells. 200 μL of RPMI1640 medium containing the test compound was added into every well. The wells were immediately photographed under a microscope. Each sample was assayed in triplicate wells of the 96-well plate and a control group was set up. Following 24 h of incubation, the wells were photographed and measured under a microscope. Migration inhibition rate=1−(wound width at 0 h−wound width at 24 h in administration group)/(wound width at 0 h−wound width at 24 h in control group)×100%. As shown in FIGS. 2A and 2B, the migration inhibition rates from the three measurements were combined to obtain an average migration inhibition rate.

4. Results in FIGS. 1A and 1B showed that the compounds ADC-8 and ADC-9 at a concentration of 30 μM showed a similar inhibition compared with parent compound AD on the proliferation of LX-2 cells. In contrary, other compounds disclosed herein each had significantly lower cytotoxicity than AD.

Results in FIGS. 1A, 1B, 2A and 2B showed that the compounds disclosed herein at a non-toxic concentration had significantly inhibition compared with AD on migration of LX-2 cells, and had a higher safety index.

EXAMPLE 2

The compounds of the disclosure inhibit EMT of human type II alveolar epithelial cells A549.

Type II alveolar epithelial cells present in the alveoli are stimulated by cytokines such as inflammatory mediators and growth factors. The change of the cell morphology from cobblestone to fusiform, indicates the completion of epithelial mesenchymal transition (EMT) and the transition to interstitial cell type. Collagen fibers are further synthesized in the cells of fibroblasts, but a large amount of collagen fiber deposition can aggravate the course and severity of interstitial pulmonary fibrosis. The compounds of the disclosure were compared with andrographolide (AD) to determine the anti-pulmonary fibrosis activity of the compounds by morphological observation and wound healing (cell migration) assay.

1. Cell Culture

A549 cells were cultured in a RPMI1640 medium containing 10% (V/V) fetal bovine serum (FBS), 100 μg/mL streptomycin, and 100 IU/mL penicillin, followed by incubation in a 37° C. incubator with a saturated humidity and 5% $CO_2$.

2. In Vitro Cytotoxicity MTT Assay

Figure 3A:
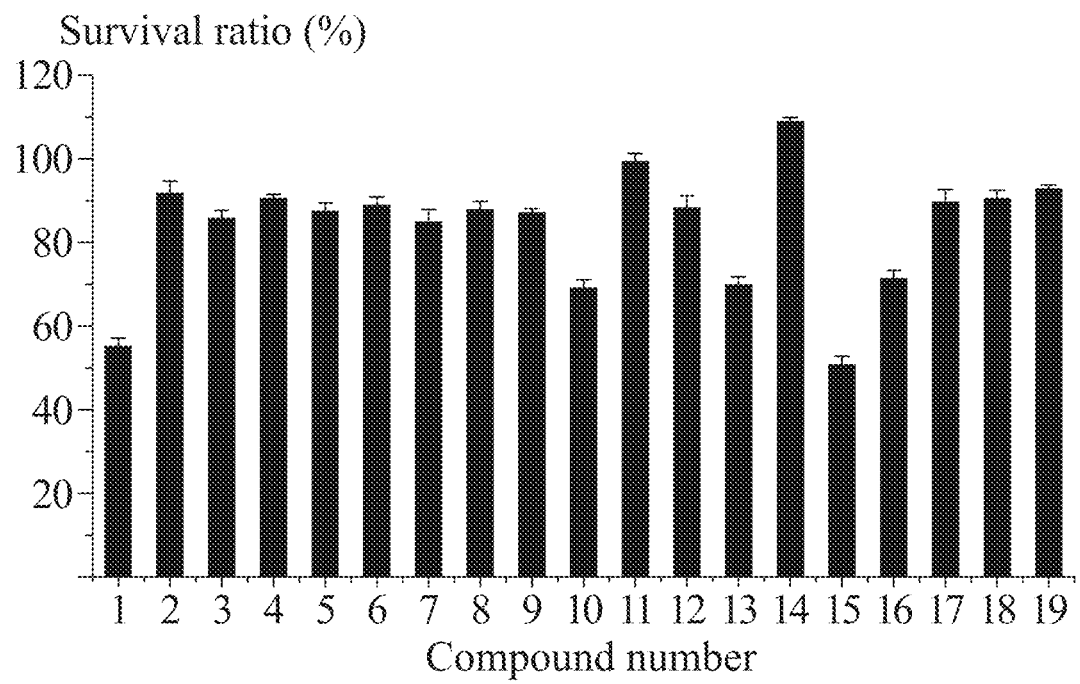
FIGS. 3A-3B show the effect of AD and the representative compounds of the disclosure on the viability of human type II alveolar epithelial cells A549.
Figure 3B:
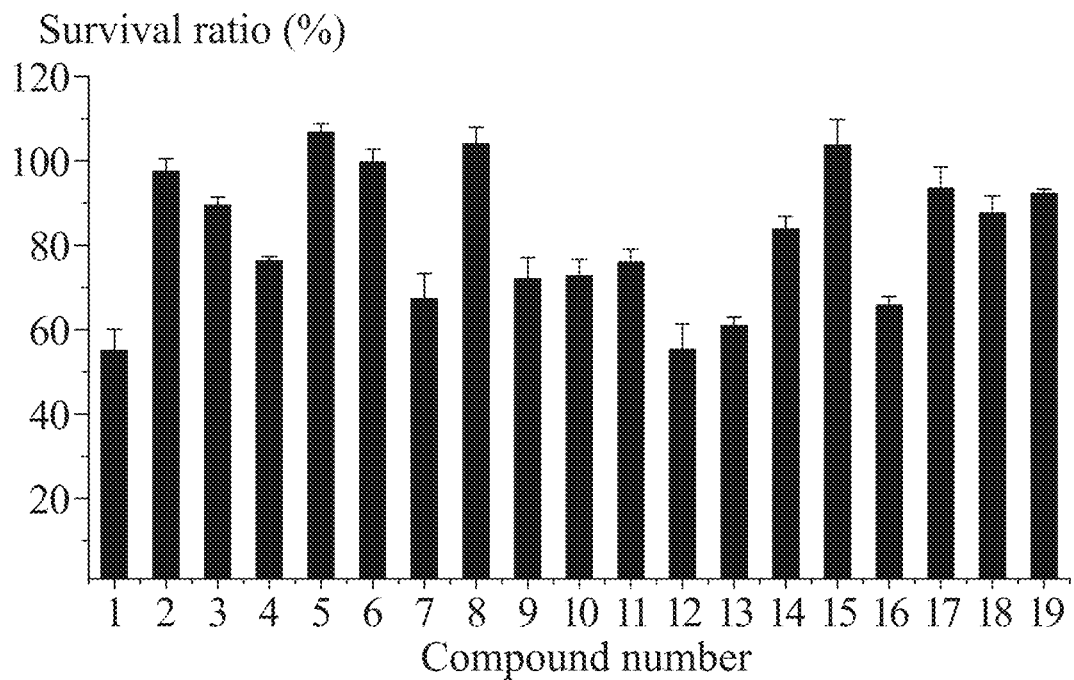

A549 cells in the logarithmic growth phase were digested with 0.25% (W/V) trypsin, diluted into $5.0 \times 10^4$ cell/mL cell suspension with RPMI1640 medium containing 10% (V/V) FBS, and transferred into a 96-well plate for 200 μL per well. After incubation in the 37° C. incubator with 5% $CO_2$ for 24 hours, the medium comprising different concentration of test compounds were added into the wells. Under these conditions, the maximum final drug concentration in the assay was 30.00 μM. The experiment was performed in triplicate. After further incubation for 48 hours, other steps were the same as Example 1. The results were averaged, as shown in FIGS. 3A and 3B.

Figure 4A:
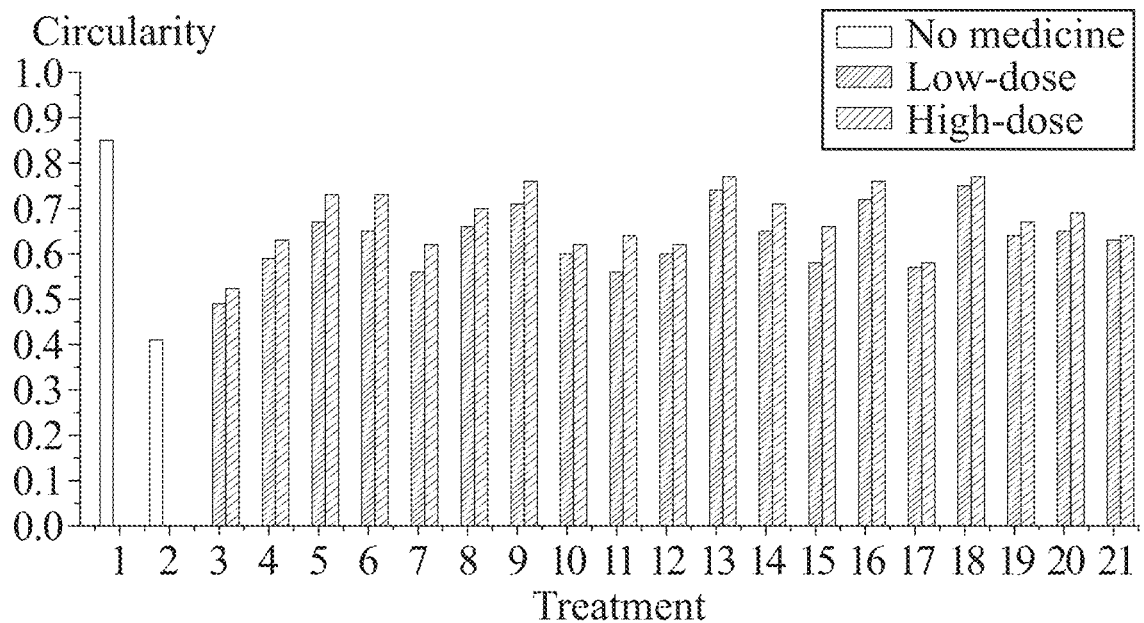
FIGS. 4A-4B show the effect of AD and the representative compounds of the disclosure on the EMT of human type II alveolar epithelial cells A549 induced by TGF-$\beta_1$. The representative compounds in FIG. 4A refer to ADY and derivatives thereof. The compound AD has a low dose of 1.25 µM and a high dose of 2.50 µM. The compound ADY-8 has a low dose of 0.63 µM and a high dose of 1.25 µM. Other compounds have a low dose of 0.31 µM and a high dose of 0.63 µM.
Figure 4B:
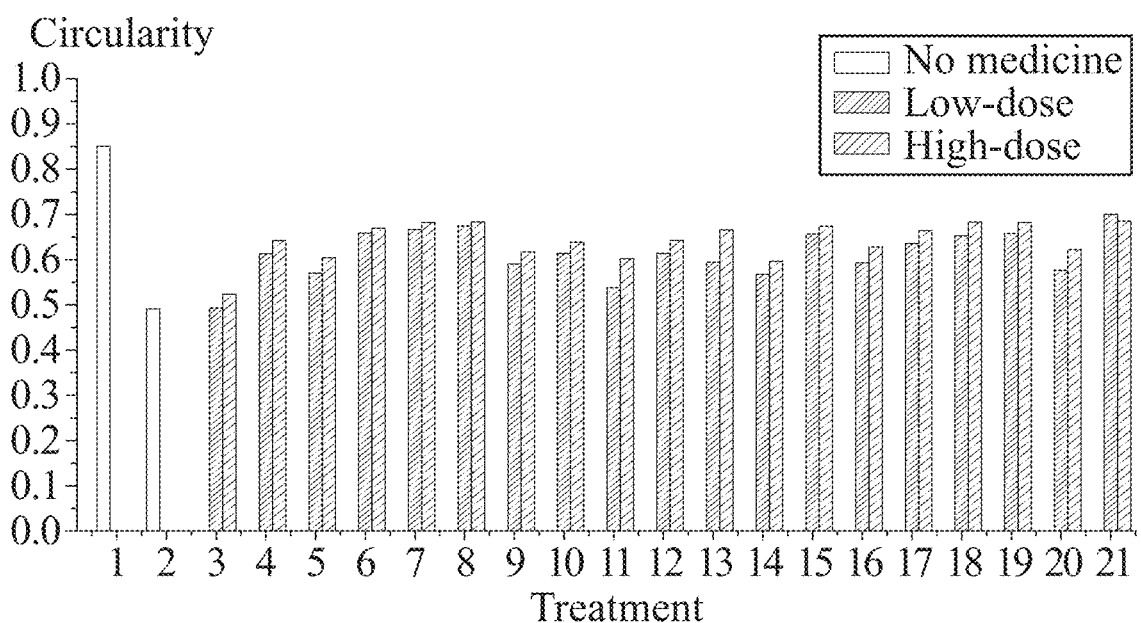

3. Morphological Observation to Detect the Effect of Test Compounds on EMT of A549 Cells A549 cells in logarithmic growth phase were digested with 0.25% (W/V) trypsin, diluted into $3.0 \times 10^5$/mL cell suspension with RPMI1640 medium containing 10% (V/V) FBS, and further transferred into a 96-well plate for 200 μL per well. The cells were cultured as monolayer for 12 hours and grew to 80%-90% confluence, followed by removal of the medium. The serum free medium was added and re-synchronized for 24 h, followed by removal of the medium. The monolayer was washed 2 times with PBS to remove floating cells. 200 μL of RPMI1640 medium containing different concentrations of the test compounds and TGF-$\beta_1$ (5 ng/mL) was added to every well. The wells were immediately photographed under a microscope (100×). Each sample was assayed in triplicate wells of the 96-well plate and a control group was set up. Following 48 h of incubation, the cells were photographed and measured under a microscope. A total of 5 fields were selected from the three wells treated at the same concentration for each compound, and more than 100 cells were measured. The photos were processed using Photoshop CS6 software and the circularity was calculated (Formula $e=4\pi \times S/C^2$, where e represents circularity, S represents area, and C represents perimeter). The results were averaged, as shown in FIGS. 4A and 4B.

4. In Vitro Wound Healing Assay to Detect the Effect of Test Compounds on Migration of A549 Cells.

Figure 5A:
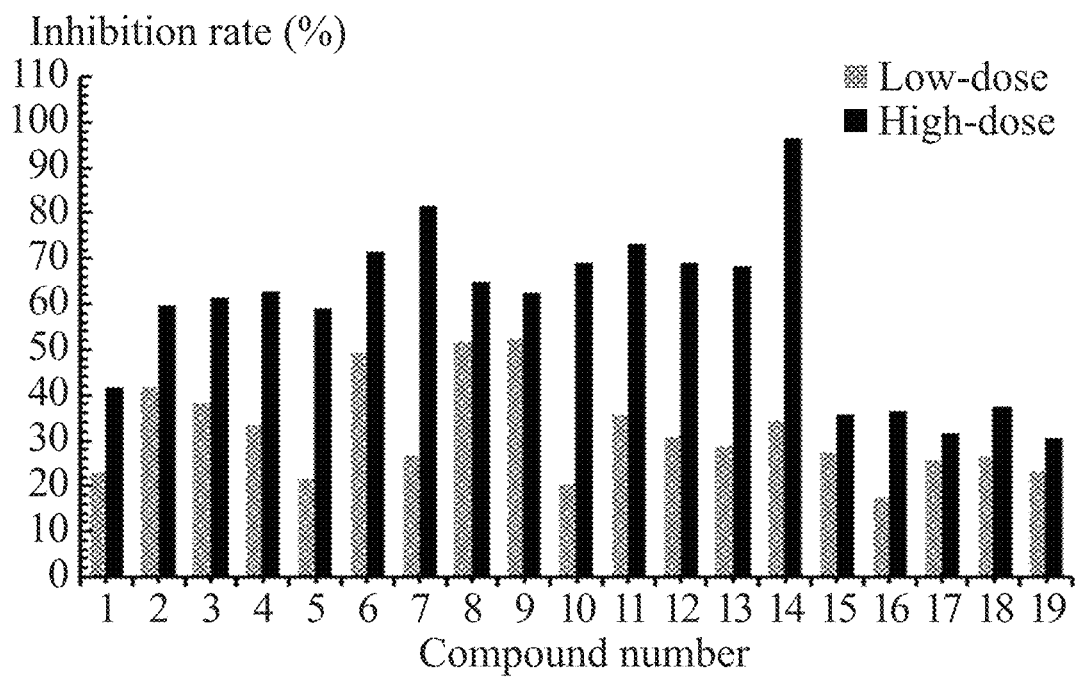
FIGS. 5A-5B show the results of inhibition of AD and the representative compound of the disclosure on the migration in human type II alveolar epithelial cells A549 induced by TGF-$\beta_1$. The representative compounds in FIG. 5A refer to ADY and derivatives thereof. The compound AD has a low dose of 0.31 µM and a high dose of 0.63 µM. The compound ADY, ADY-1, ADY-2, ADY-4, ADY-6, ADY-7, ADY-8 and ADY-13 each has a low dose of 0.08 µM and a high dose of 0.16 µM. Other compounds have a low dose of 0.16 µM and a high dose of 0.32 µM.
Figure 5B:
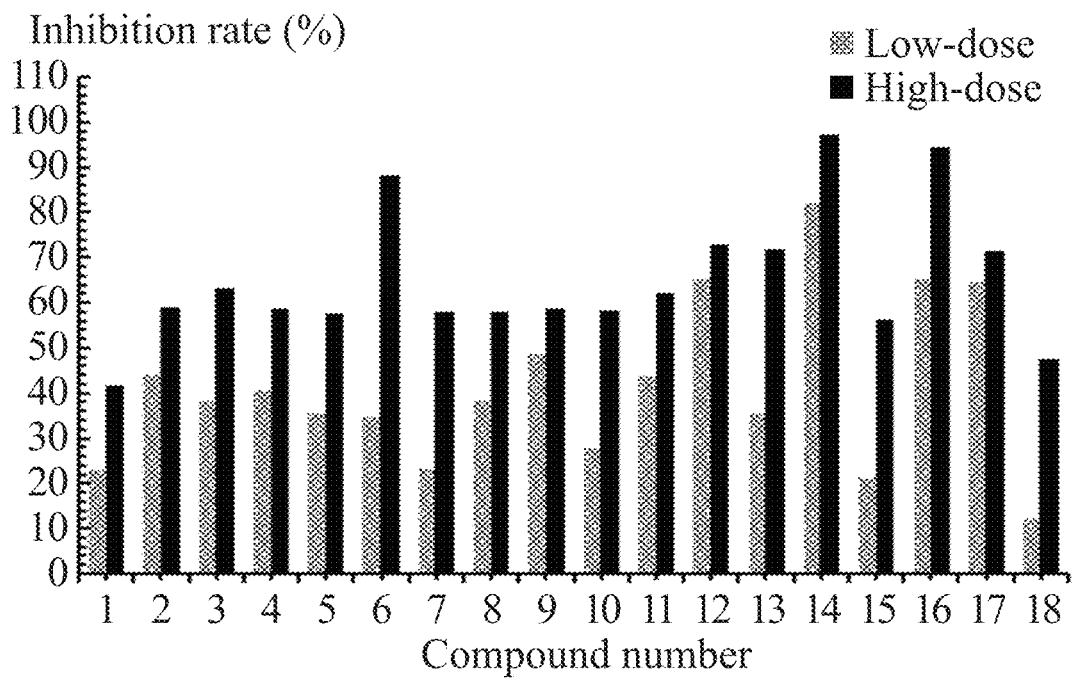

A549 cells in logarithmic growth phase were digested with 0.25% (W/V) trypsin, diluted into $1.0 \times 10^5$/mL cell suspension with RPMI1640 medium containing 10% (V/V) FBS, and further transferred into a 96-well plate for 200 μL per well. The cells were cultured as monolayer for 24 hours and grew to 80%-90% confluence, followed by removal of the medium. The serum free medium was added and re-synchronized for 24 h. A scratch was created through the cell monolayer, and the monolayer was washed twice with PBS to remove floating cells. After the line scratch, 200 μL of RPMI1640 medium containing the test compound was added into every well. The wells were immediately photographed under a microscope. Each sample was assayed in triplicate wells of the 96-well plate and a control group was set up. Following 24 h of incubation, the cells were photographed and measured under a microscope. Migration distance=wound width at 0 h wound width at 24 h. As shown in FIGS. 5A and 5B, migration inhibitory rate=1−(migration distance in TGF-$\beta_1$ treatment group−migration distance in compound-administered group)/migration distance in TGF-$\beta_1$ treatment group−migration distance in control group)× 100%.

5. Experimental Results

Results in FIGS. 3A and 3B showed that the compounds disclosed herein had lower inhibitory effect on A549 cell proliferation than the parent compound AD.

Results in FIGS. 3A, 3B, 4A, 4B, 5A and 5B showed that the compounds disclosed herein at a non-toxic concentration had significantly inhibition compared with AD on EMT of A549 cells and had a higher safety index.

EXAMPLE 3

Compounds of the disclosure inhibit TGF-β1-induced EMT of human proximal tubular epithelial cells HK-2.

Early studies have found that tubular epithelial cells can trans-differentiate to fibroblasts and express their fibroblast-specific protein (FSP1). Epithelial-mesenchymal transition of tubular epithelial cells is one of the important pathogenesis of renal interstitial fibrosis. Following TGF-$\beta_1$ stimulation, human proximal tubular epithelial cells HK-2 (provided by the China Center for Type Culture Collection, Wuhan, China) were used to evaluate the anti-renal fibrosis effect of the compounds compared with andrographolide (AD) by morphological observation and wound healing assay.

1. Cell Culture and Drug Treatment

HK-2 cells were cultured in a DMEM/F12 medium containing 10% (V/V) fetal bovine serum (FBS), 100 μg/mL streptomycin, and 100 IU/mL penicillin, followed by incubation at 37° C. in a humidified atmosphere with 5% $CO_2$.

2. In Vitro Cytotoxicity MTT Assay

Figure 6A:
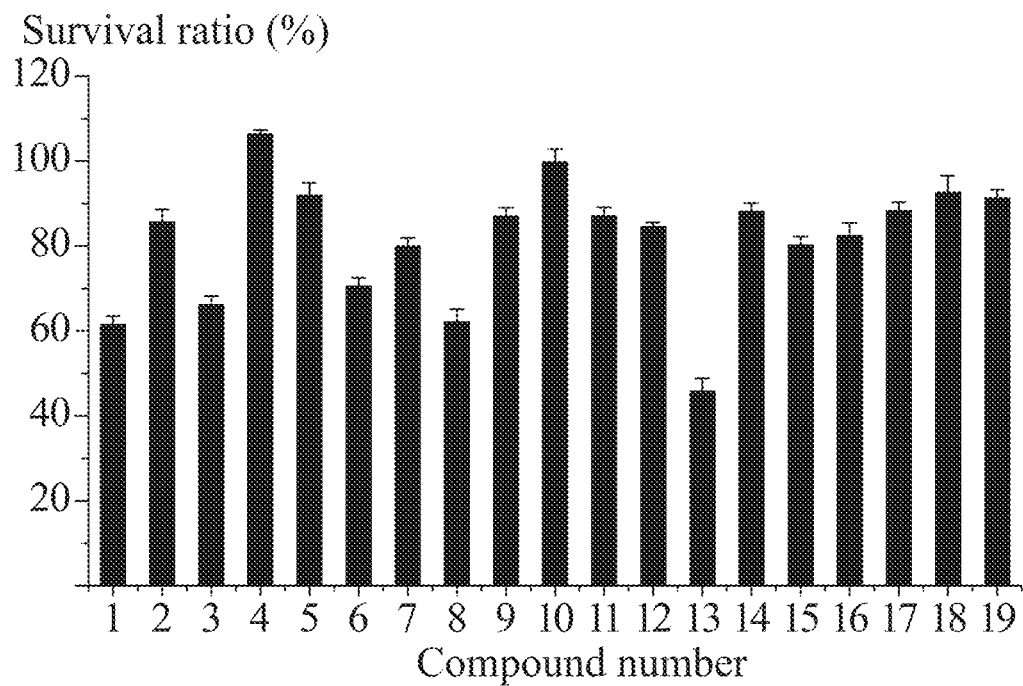
FIGS. 6A-6B show the effect of AD and the representative compounds (30.00 μM) of the disclosure on the viability of human renal proximal tubule epithelial cells HK-2. The representative compounds in FIG. 6A refer to ADY and derivatives thereof. 30.00 μM AD shows a lower inhibitory activity against the cell proliferation then the equivalent dose of ADY-2, ADY-5, ADY-6, ADY-8, and ADY-11.
Figure 6B:
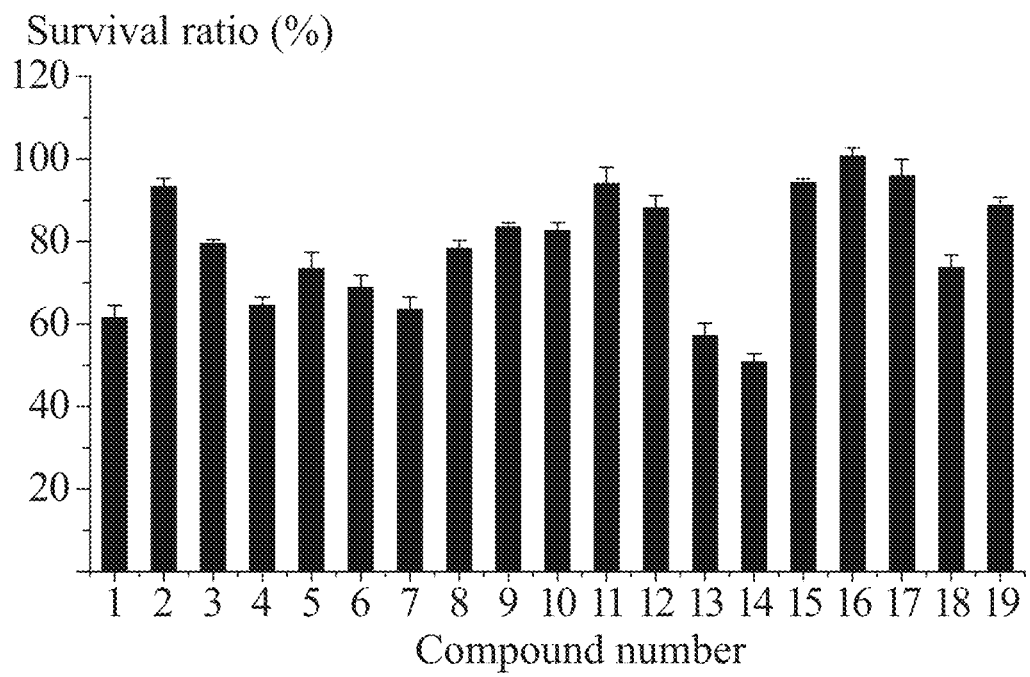

HK-2 cells in the logarithmic growth phase were digested with 0.25% (W/V) trypsin and 0.02% EDTA (W/V), diluted into $7.0\times10^4$ cell/mL cell suspension with DMEM/F12 medium containing 10% (V/V) FBS, and transferred into a 96-well plate for 200 μL per well. After incubation in the 37° C. incubator with 5% $CO_2$ for 24 hours, the medium comprising different concentration of test compounds were added into the wells. Under these conditions, the maximum final drug concentration in the assay was 30.00 μM. The experiment was performed in triplicate. After further incubation for 48 hours, other steps were the same as Example 1. The results were averaged, as shown in FIGS. 6A and 6B.

Figure 7A:
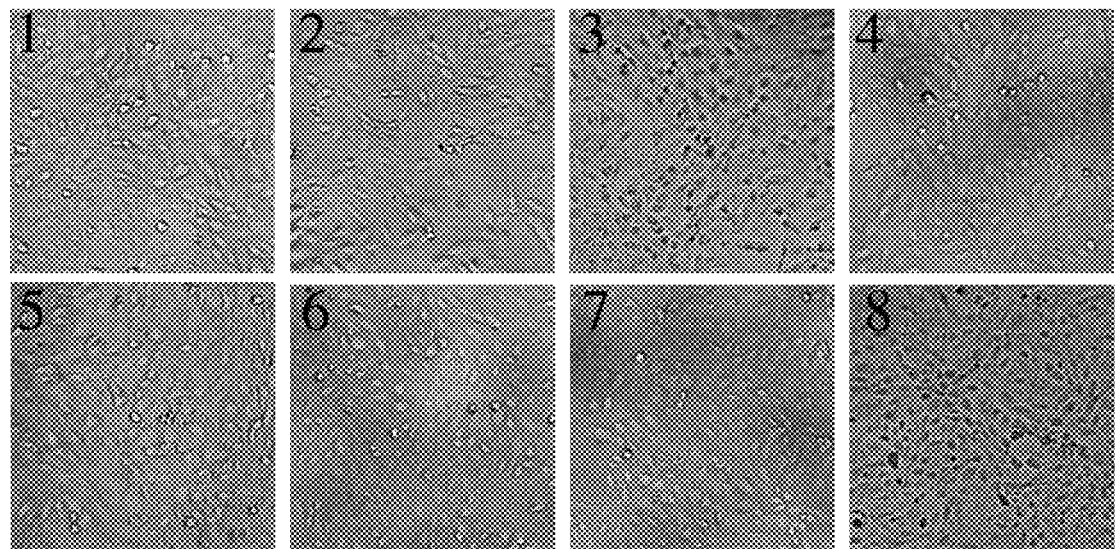
FIGS. 7A-7B show the effect (containing micrographs; ×100 times) of AD and the representative compounds of the disclosure on the EMT of human renal proximal tubule epithelial cells HK-2 induced by TGF-β$_1$. The representative compounds in FIG. 7A refer to ADY and derivatives thereof.
Figure 7B:
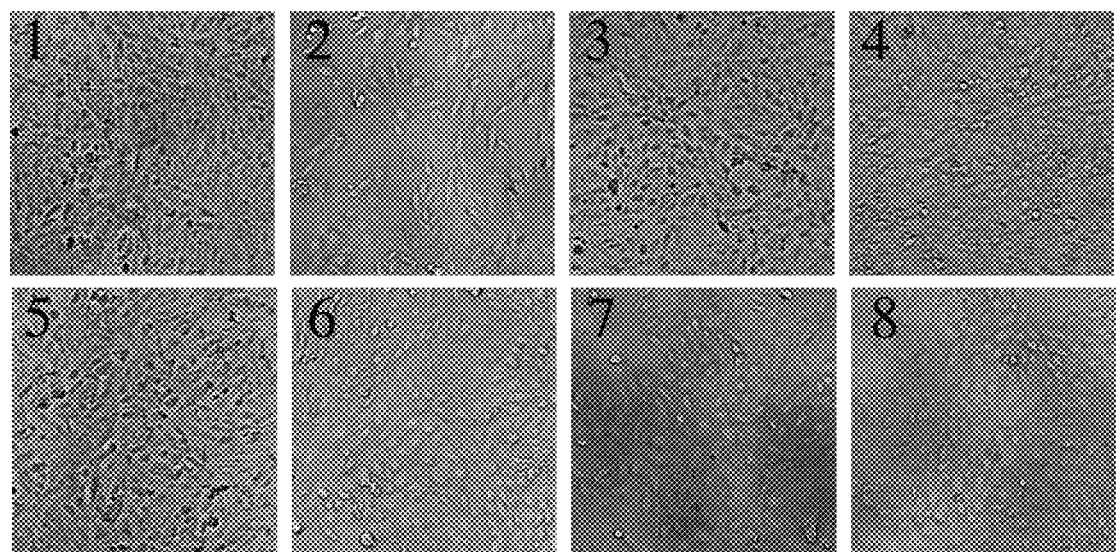

3. Morphological Observation to Detect the Effect of Test Compounds on Morphology of HK-2 Cells Stimulated by TGF-$\beta_1$ HK-2 cells in logarithmic growth phase were digested with 0.25% (W/V) trypsin and 0.02% EDTA (W/V), diluted into $5.0\times10^4$/mL cell suspension with DMEM/F12 medium containing 10% (V/V) FBS, and further transferred into a 96-well plate for 200 μL per well. The cells were cultured as monolayer for 24 hours, followed by removal of the medium and washing 2 times with 0.01 M PBS. The serum free medium was added and re-synchronized for 24 h. After removal of the serum free medium, 200 μL of DMEM/F12 medium containing different concentrations of the test compounds and TGF-$\beta_1$ (5 ng/mL) was added into every well. Each sample was assayed in triplicate and a control group was set up. Following 48 h of incubation, the cells were photographed and measured under a microscope. The results regarding the morphological observation of partial compounds were shown in FIGS. 7A and 7B.

4. In Vitro Wound Healing Assay to Detect the Effect of Test Compounds on Migration of HK-2 Cells.

Figure 8A:
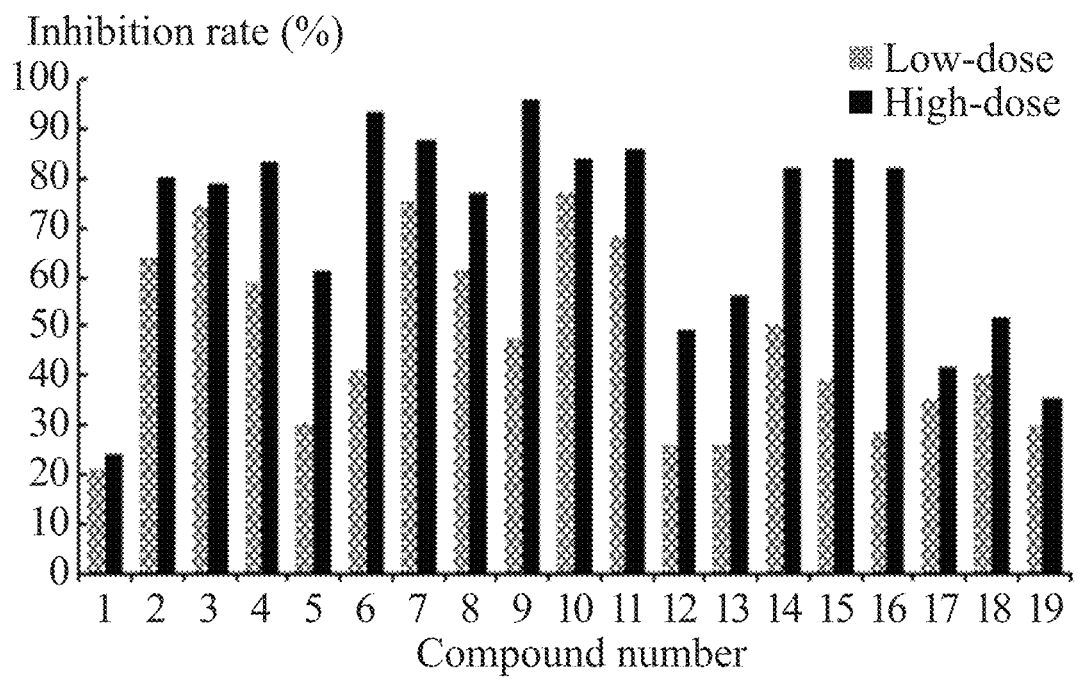
FIGS. 8A-8B show the results of inhibition of AD and the representative compound of the disclosure on the migration in human renal proximal tubule epithelial cells HK-2 induced by TGF-β$_1$. The representative compounds in FIG. 8A refer to ADY and derivatives thereof. The compounds AD, ADY-11, ADY-13, ADY-15, ADY-16, and ADY-17 each have a low dose of 0.08 μM and a high dose of 0.16 μM. Other compounds each have a low dose of 0.04 μM and a high dose of 0.08 μM.
Figure 8B:
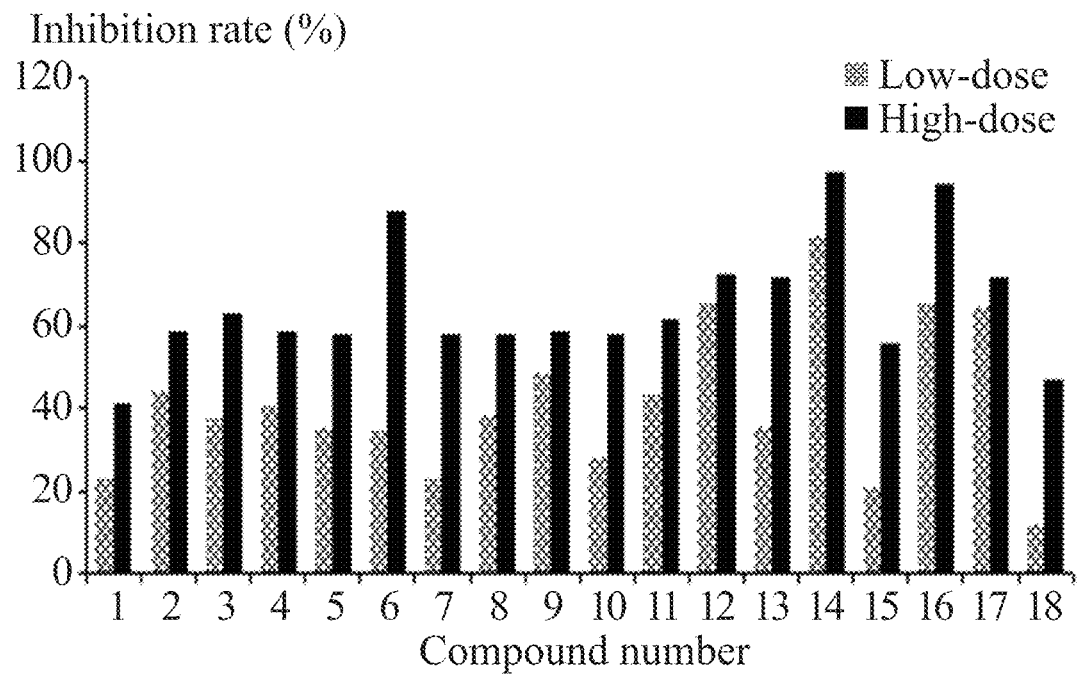

HK-2 cells in logarithmic growth phase were digested with 0.25% (W/V) trypsin and 0.02% EDTA (W/V), diluted into $2.0\times10^4$/mL cell suspension with DMEM/F12 medium containing 10% (V/V) FBS, and transferred into a 96-well plate for 200 μL per well. The cells were cultured as monolayer for 24 hours and grew to confluence, followed by removal of the medium and washing 2 times with 0.01 M PBS. The serum free medium was added to each well and re-synchronized for 24 h, followed by removal of the medium. The cell monolayer was scratched by using a 200 μL pipette tip and washed 2 times with PBS. After the line scratch, 200 μL of DMEM/F12 medium containing 2% FBS, different concentrations of the test compounds and TGF-$\beta_1$ (5 ng/mL) was added into every well. Each sample was assayed in triplicate and a control group was set up. Following 24 h of incubation, the cells were photographed and measured under a microscope. Migration distance=wound width at 0 h wound width at 24 h. As shown in FIGS. 8A and 8B, migration inhibitory rate=1−(migration distance in TGF-$\beta_1$ treatment group−migration distance in compound-administered group)/migration distance in TGF-$\beta_1$ treatment group−migration distance in control group)×100%.

5. Experimental Results

Results in FIGS. 6A and 6B showed that only 9 compounds had higher inhibitory effect on proliferation of HK-2 cells than the parent compound AD, i.e., ADY-2, ADY-5, ADY-6, ADY-8, ADY-11 and ADC-5, ADC-6, ADC-11 and ADC-12.

Results in FIGS. 6A, 6B, 7A, 7B, 8A and 8B showed that the compounds disclosed herein at a non-toxic concentration had higher inhibitory effect on EMT of HK-2 cells than the parent compound AD and had a higher safety index.

EXAMPLE 4

The compounds of the disclosure inhibit angiotensin II (AngII)-induced migration of human primary myocardial fibrosis cells HCFB.

Studies have shown that cardiac fibroblasts are the main effector cells of myocardial fibrosis, and they proliferate when stimulated by active substances such as AngII, and their phenotypes are transformed into myofibroblasts that secrete extracellular matrix. MTT assay was carried out to determine the effect of the compounds of the disclosure on the HCFB proliferation, and in vitro wound healing assay was used to evaluate the effect of the compounds of the disclosure on the AngII-induced HCFB migration.

1. Cell Culture

Human primary cardiac fibroblast HCFB (provided by Shangcheng Beina Chuanglian Biotech Co., Ltd.) was compared with andrographolide to study the in vitro anti-myocardial fibrosis effect of the compounds of the disclosure. HCFB cells were cultured in H-DMEM medium containing 8% (V/V) fetal bovine serum, 100 μg/mL streptomycin, and 100 IU/mL penicillin respectively, and then these mediums were incubated at 37° C. in a humidified atmosphere with 5% $CO_2$.

2. In Vitro Cytotoxicity MTT Assay

HCFB cells in the logarithmic growth phase were digested with 0.25% (W/V) trypsin, diluted into $5.0\times10^4$ cell/mL cell suspension with H-DMEM medium containing 8% FBS, and transferred into a 96-well plate for 7000 cells per well. After incubation in the 37° C. incubator with 5% $CO_2$ for 24 hours, a solution containing different concentrations of AD or test compounds were added to the wells. After further incubation for 48 hours, other steps were the same as Example 1. The results were averaged, as shown in FIGS. 9A and 9B.

Figure 10A:
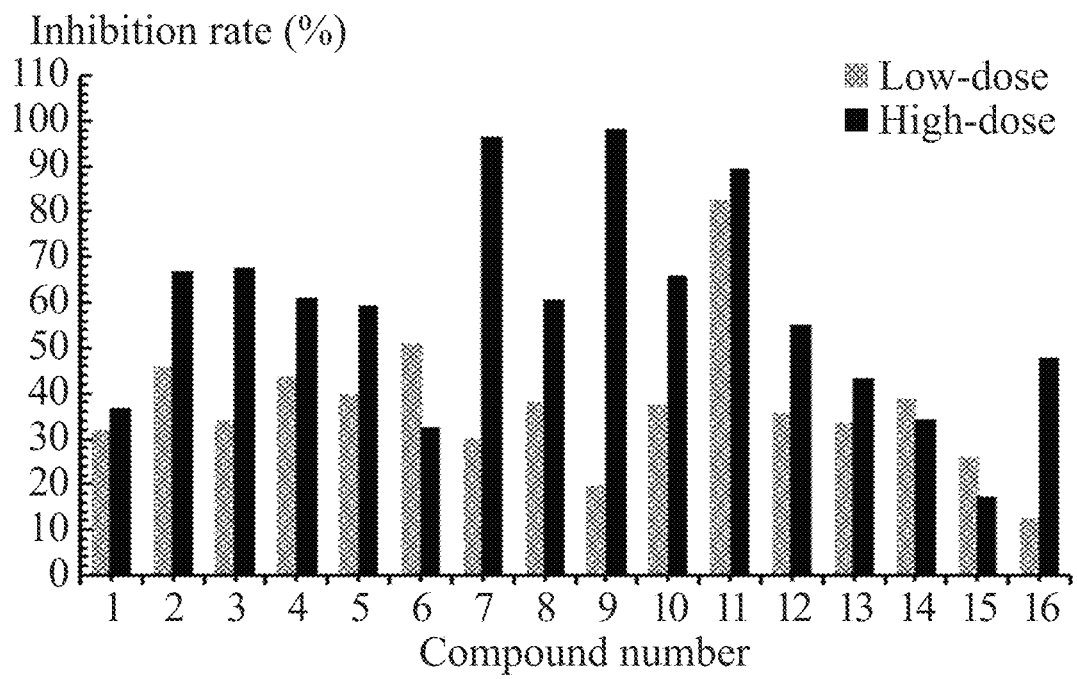
FIGS. 10A-10B show the results of inhibitory effect of AD and the representative compound of the disclosure on the migration in primary human cardiac fibroblasts HCFB induced by Ang II. The representative compounds in FIG. 10A refer to ADY and derivatives thereof. The compound AD and ADY have a low dose of 0.31 μM and a high dose of 0.63 Other compounds each have a low dose of 0.16 μM and a high dose of 0.31 In FIG. 10A: 1. Ang II ($10^{-7}$ mol/L)+AD; 2. Ang II+ADY; 3. Ang II+ADY-1; 4. Ang II+ADY-2; 5. Ang II+ADY-3; 6. Ang II+ADY-4; 7. Ang II+ADY-5; 8. Ang II+ADY-6; 9. Ang II+ADY-7; 10. Ang II+ADY-8; 11. Ang II+ADY-9; 12. Ang II+ADY-10; 13. Ang II+ADY-11; 14. Ang II+ADY-12; 15. Ang II+ADY-13; 16. Ang II+ADY-14. The representative compounds in FIG. 10B refer to ADC and derivatives thereof. The compound AD and ADC have a low dose of 0.31 μM and a high dose of 0.63 Other compounds each have a low dose of 0.16 μM and a high dose of 0.31 In FIG. 10B: 1. Ang II+AD; 2. Ang II+ADC; 3. Ang II+ADC-1; 4. Ang II+ADC-2; 5. Ang II+ADC-3; 6. Ang II+ADC-4; 7. Ang II+ADC-5; 8. Ang II+ADC-6; 9. Ang II+ADC-7; 10. Ang II+ADC-8; 11. Ang II+ADC-9; 12. Ang II+ADC-10; 13. Ang II+ADC-11; 14. Ang II+ADC-12; 15. Ang II+ADC-13; 16. Ang II+ADC-15; 17. Ang II+ADC-16; 18. Ang II+ADC-17.
Figure 10B:
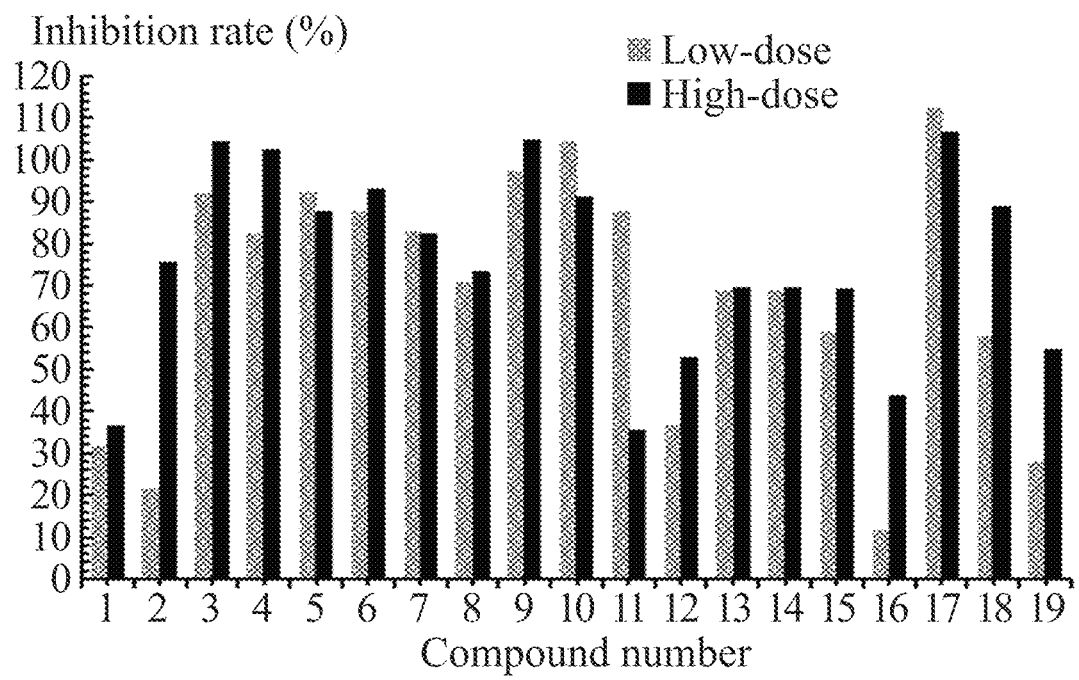
Figure 11A:
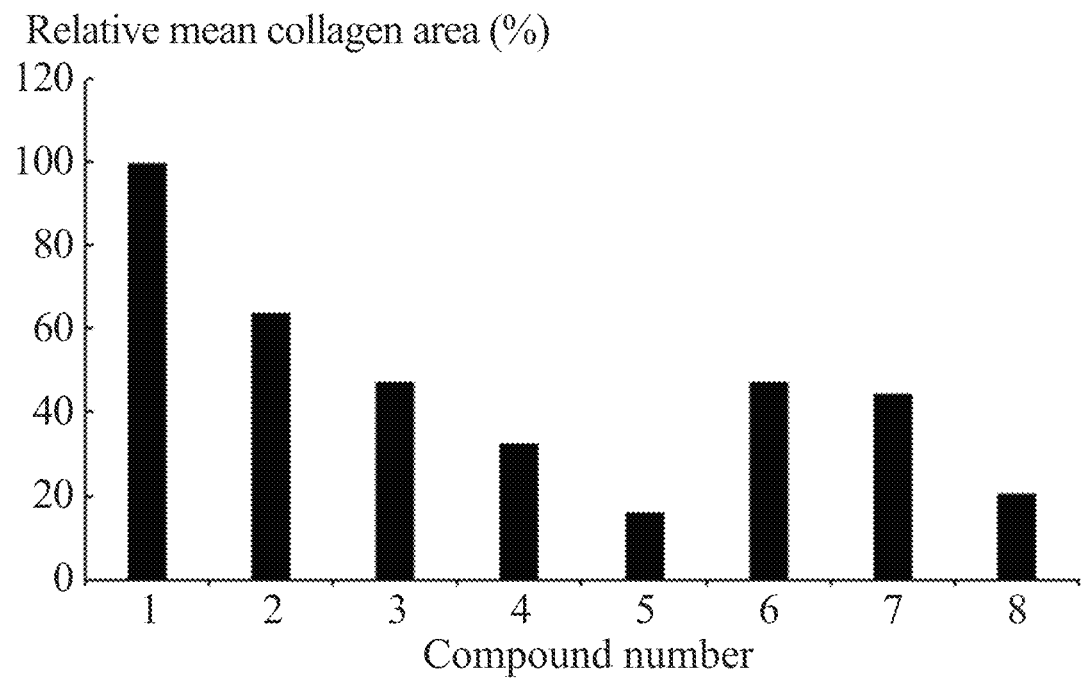
FIGS. 11A-11B show the effect of AD and compounds of the disclosure on reducing liver tissue collagen levels (Sirius red staining). The representative compounds in FIG. 11A refer to ADY and derivatives thereof.
Figure 11B:
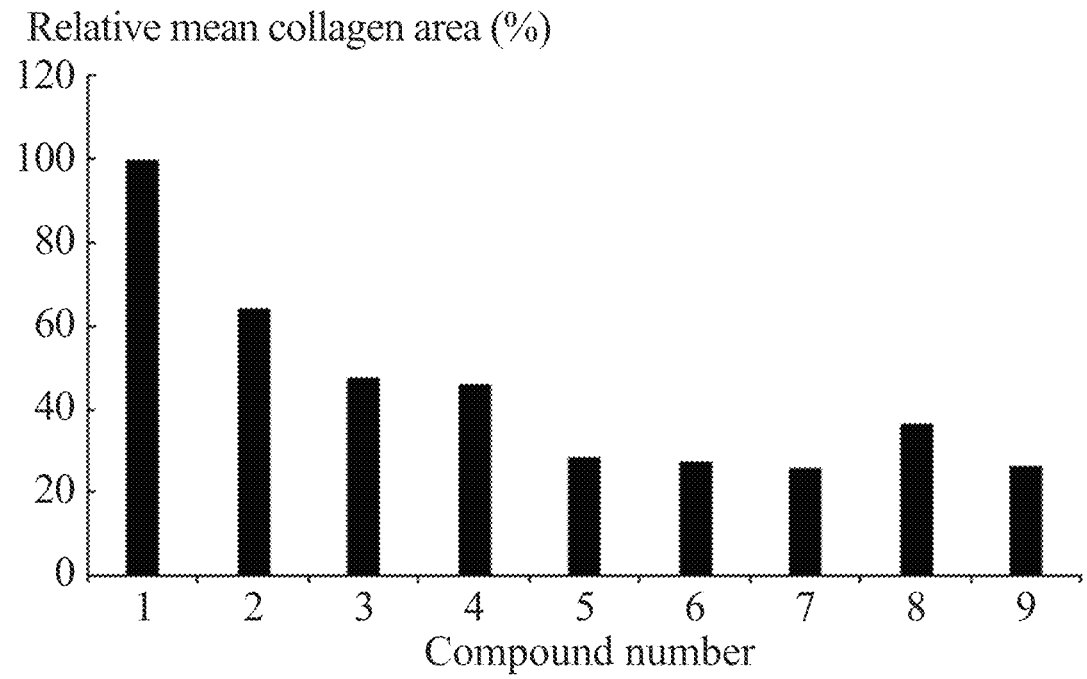
Figure 12A:
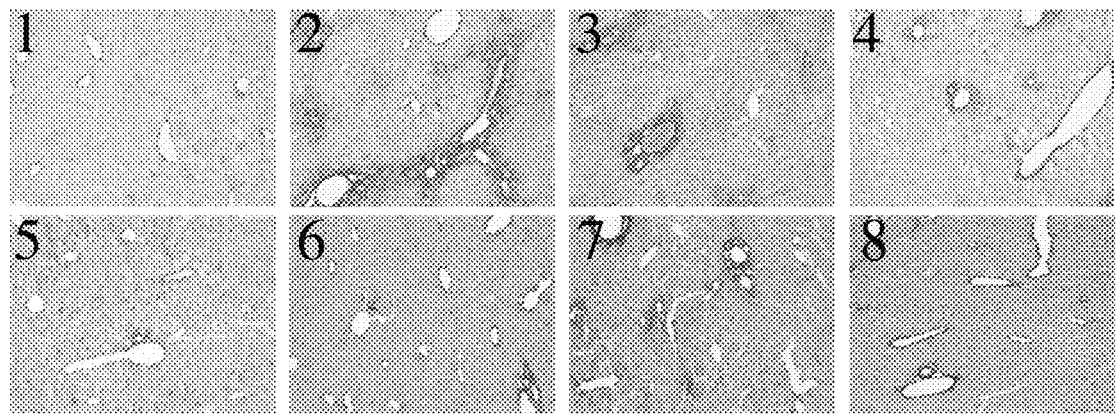
FIGS. 12A-12B show the effect of AD and compound of the disclosure on improvement in the hepatic fibrosis in KM mice induced by bile duct ligation (Sirius red staining; micrograph, ×100 times). The representative compounds in FIG. 12A refer to ADY and derivatives thereof.
Figure 12B:
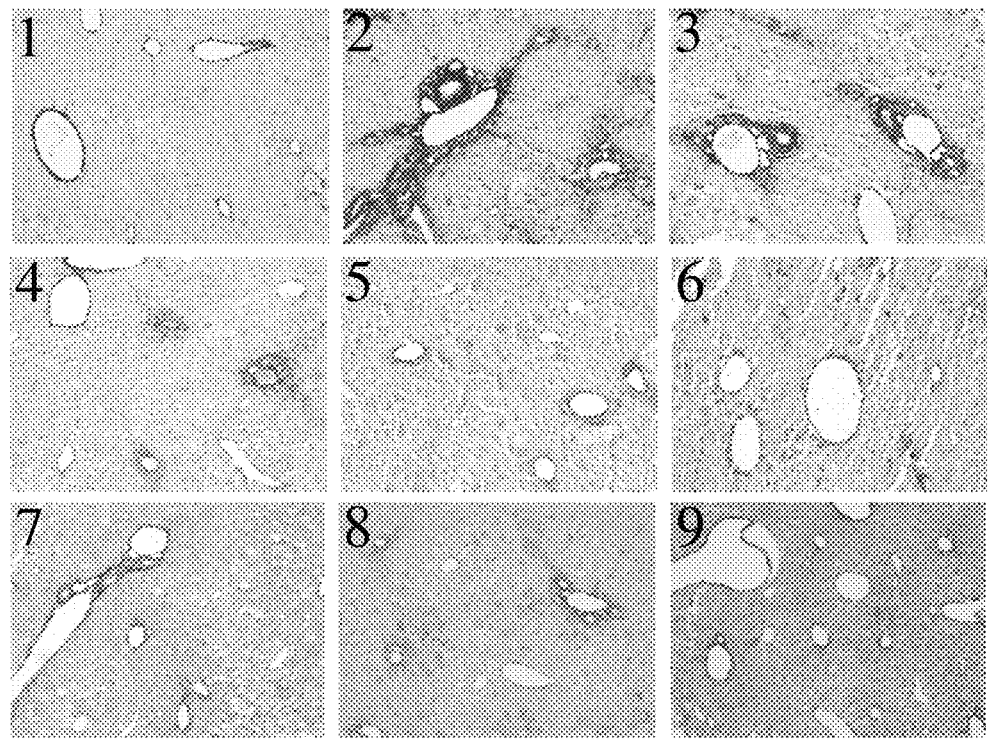

3. In Vitro Wound Healing Assay to Detect the Inhibitory Effect of Test Compounds on the Migration of HCFB Stimulated by AngII HK-2 cells in logarithmic growth phase were digested with 0.25% (W/V) trypsin, diluted into cell suspension with H-DMEM medium containing 8% (v/v) FBS, and further transferred into a 96-well plate for 20000 cells per well. The cells were cultured as monolayer for 24 hours and grew to confluence, followed by removal of the medium. The serum free medium was added and re-synchronized for 24 h. The cell monolayer was scratched by using a 200 μL pipette tip and washed 2 times with 0.01 M PBS. 200 μL of H-DMEM medium containing 0.5% DMSO, different concentrations of the test compounds and AngII ($10^{-7}$ mol/L) was added into every well. H-DMEM medium containing 0.5% DMSO was taken as control group, and H-DMEM medium containing Ang II and 0.5% DMSO was taken as Ang II group. Each sample was assayed in triplicate and a control group was set up. Following 24 h of incubation, the cells were photographed and measured under a microscope. Migration distance=wound width at 0 h wound width at 24 h. Migration inhibitory rate=1−(migration distance in AngII treatment group−migration distance in compound-administered group)/migration distance in AngII treatment group−migration distance in control group)×100%. The results were averaged, as shown in FIGS. 10A and 10B.

4. Experimental Results

Figure 9A:
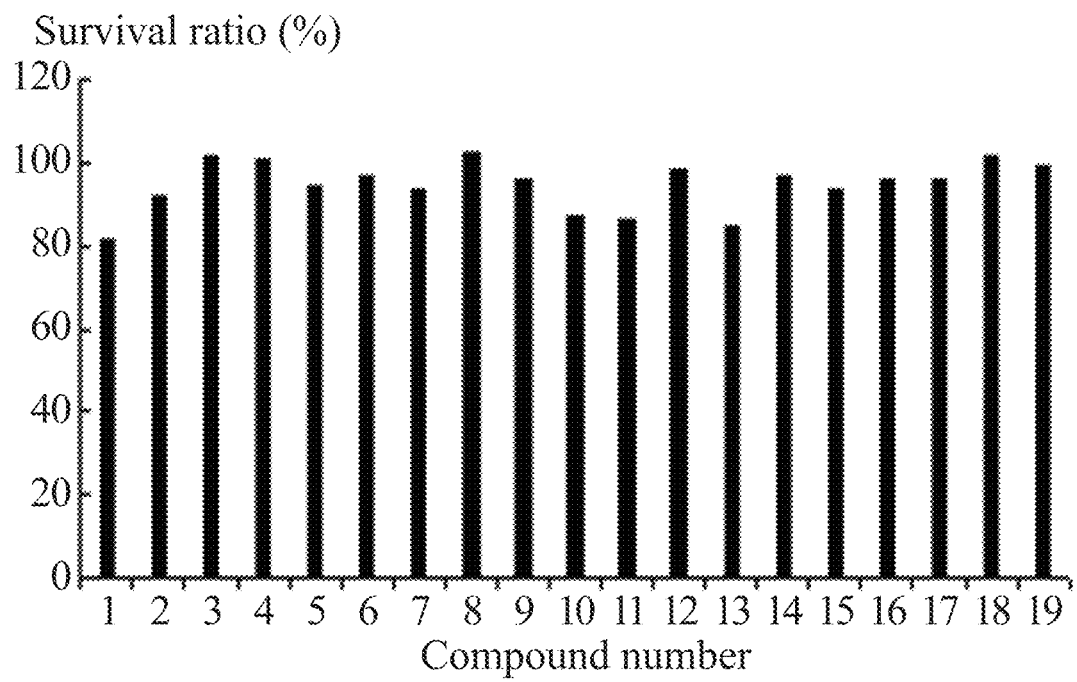
FIGS. 9A-9B show the effect of AD and the representative compounds (15.00 μM) of the disclosure on the viability of primary human cardiac fibroblasts HCFB. The representative compounds in FIG. 9A refer to ADY and derivatives thereof, where, 1. AD; 2. ADY; 3. ADY-1; 4. ADY-2; 5. ADY-3; 6. ADY-4; 7. ADY-5; 8. ADY-6; 9. ADY-7; 10. ADY-8; 11. ADY-9; 12. ADY-10; 13. ADY-11; 14. ADY-12; 15. ADY-13; 16. ADY-14; 17. ADY-15; 18. ADY-16; 19. ADY-17. The representative compounds in FIG. 9B refer to ADC and derivatives thereof, where, 1. AD; 2. ADC; 3. ADC-1; 4. ADC-2; 5. ADC-3; 6. ADC-4; 7. ADC-5; 8. ADC-6; 9. ADC-7; 10. ADC-8; 11. ADC-9; 12. ADC-10; 13. ADC-11; 14. ADC-12; 15. ADC-13; 16. ADC-14; 17. ADC-15; 18. ADC-16; 19. ADC-17.
Figure 9B:
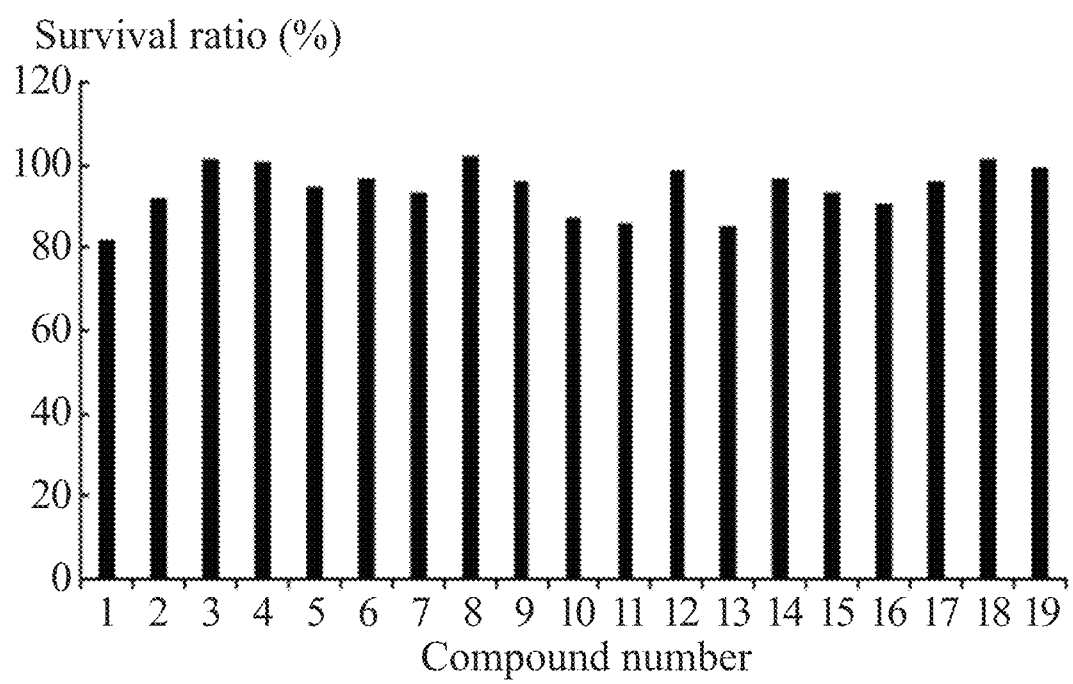

Results in FIGS. 9A and 9B showed that the HCFB cells treated with the compounds of the disclosure at a concentration of 15 μmol/L had higher cell viability than the equivalent dose of parent compound AD. Results in FIGS. 9A, 9B, 10A and 10B showed that the compounds disclosed herein within experimental concentration range had higher inhibitory effect on the migration of AngII-induced HCFB cells than the parent compound AD.

EXAMPLE 5

The compounds of the disclosure significantly improve the hepatic fibrosis in KM mice induced by bile duct ligation (BDL)

1. Experimental Animals

SPF grade KM mice, healthy, male, with a body weight of 20±2 g, were purchased from Henan Experimental Animal Center. (License No. SOCK (Yu) 2017-0001).

2. Experimental Methods

After KM mice were fed ad libitum for 3 days, they were randomly divided into multiple groups including a sham-operated control group, a model group, an AD control group, and different compound-administered groups, six mice per group. The sham operation group and the model group were administered with 0.5% Sodium CMC (Na CMC) via gavage, and the other administration groups were administered 0.5% CMC-Na suspension of the corresponding drug, and the administration lasted for 10 days. Mice should be strictly fasting with nothing but water 12 hours prior to surgery. The mice were anesthesia by intraperitoneally injecting with 0.5% sodium pentobarbital. After limb immobilization in a supine position, the anesthetized mice were prepared. The abdomen of the mice was shaved and then swabbed with iodine to sterilize the skin regions. After spreading of surgery cloth, the abdomen was opened along the abdominal wall in the midline. The duodenum was found along the stomach, then pull upwards to just separate from the common bile duct. Double-ligated with 4/0 silk thread and disconnected the common bile duct with a distance of 0.5 cm away from the hepatic hilum. Following the examination for no bleeding and bile leakage, the 3/0 silk thread continuous suture method was used to close the abdomen layer by layer. The wound was swabbed with iodine, and the mice rest in a 37° C. warm environment until the animals were fully awake. The sham-operated group only performed anesthesia, laparotomy and freed common bile duct, but did not ligate and break the common bile duct. Drugs were administrated by gavage on an empty stomach in the morning every day, and were given daily for 10 days. The liver was quickly excised after blood collection. The collected blood was allowed to stand in an incubator 37° C. for 45 min, and then the upper serum was collected by centrifugation at 3500 rpm for 15 min at 4° C. The liver of the lower left lobe of the mice was fixed in 10 times volume of 4% paraformaldehyde fixative, and the fixative was changed after 24 h. Pathological sections were obtained after fixation. Each section was stained with hematoxylin-eosin stain (HE) and Sirius red to observe fibrosis levels and pathological change in the liver. A histological scoring system for hepatic fibrosis: score 0: no fibrosis; stage 1: fibrous expansion of portal zones±short fibrous septa; score 2: fibrous expansion of most portal areas±short fibrous septa; score 3: fibrous expansion of most portal area (PF) with occasional portal to portal (P-P) bridging; score 4: fibrous expansion of portal areas with marked bridging (portal to portal (P-P) as well as portal to central (P-C)); score 5: Marked bridging (P-P and/or P-C), with occasional nodules (incomplete cirrhosis); score 6: cirrhosis, probable or definite. PF refers to portal fibrosis; P-P refers to portal to portal bridging fibrosis; P-C refers to portal to central bridging fibrosis. Collagen deposition was measured with Sirius red staining, and positive expression was semi-quantitatively analyzed by Image-Pro Plus. The relative collagen area=(average area of the compound-administered group−average area of the normal group)/(average area of the model group−average area of the normal group)×100%, and the results were shown in FIGS. 11A, 11B, 12A, and 12B.

3. Experimental Results

The results demonstrated that the fibrosis pathological score for liver tissue section in AD group decreased from the mean score 4.8 of model group to 2.83 (15 mg/kg; intragastric administration (ig)) and 2.10 (40 mg/kg; ig). The mean score 4.8 for the model group decreased to 0.6-1.4, which occurred to the liver tissue section in the groups administered respectively with (15 mg/kg; ig) compounds including ADY-8, ADY-6, ADY, ADC-2 and ADC-15, and (40 mg/kg; ig) compounds including ADC, ADC-4, ADC-10 and ADC-12. The mean score 4.25 for the model group decreased to 0.4 and 1.4, which occurred to the (15 mg/kg; ig) liver tissue section in the groups treated with (15 mg/kg; ig) compounds ADY-7 and ADY-12. The collagen area of liver tissues in each compound-administered group is significantly lower than that of the model group, and the effect of the compounds of the disclosure was better than that of the AD group.

Results in FIGS. 11A, 11B, 12A and 12B showed that the compounds disclosed herein exhibited higher anti-hepatic fibrosis than AD, in bile duct ligation mice.

EXAMPLE 6

The compounds of the disclosure significantly improve silica-induced pulmonary fibrosis in KM mice Pulmonary fibrosis is a lung injury caused by a variety of reasons, illustrating that the pathogenesis of pulmonary fibrosis is very complicated. Different pathogenic factors stimulate inflammation and immune response, involving a variety of cells including vascular endothelial cells, alveolar epithelial cells, fibroblasts and macrophages, and the interaction of various cytokines and inflammatory mediators. Silica is an inorganic dust that may cause severe silicosis and even threaten the human life when inhaled in large amounts. Studies have shown that the silica-induced pulmonary fibrosis is a classical model for researching pulmonary fibrosis, because there is a strong similarity in the histopathological changes between the pulmonary fibrosis caused by silicon and the human pulmonary fibrosis.

1. Experimental Animals

SPF grade KM mice, healthy, male, with a body weight of 20±2 g, were purchased from Henan Experimental Animal Center. (License No. SOCK (Yu) 2017-0001). Silica was heated at 250° C. for 1 hour to remove endotoxin. After autoclaving the heated silica was suspended in physiological saline to yield a final concentration of 75 mg/mL suspension, and stored at 4° C. for use. The suspension was shaken and sonicated for 30 minutes prior to injection.

2. Experimental Methods

After mice were fed ad libitum for 3 days, they were randomly divided into six groups including a sham-operated control group, a model group, different groups of the compounds of the disclosure, eight mice per group. The mice were anesthetized with intraperitoneal injection of 0.5% sodium pentobarbital (50 mg/kg). After the immobilization in a supine position, the anesthetized mice were prepared. The neck of the mice was shaved and then swabbed with iodine to sterilize the skin regions. An incision with a length of about 1 cm was made along the neck for separating bronchus. A silica suspension proportional (150 mg/kg) to the body weight, and 100 μL of air was immediately injected into the trachea through the cartilage space of mice. After the muscle was reset, the mice were quickly rotated for 2 minutes to evenly distribute the silica. The incision was sutured with silk thread, and the wound was subsequently swabbed with iodine. The sham operation group was injected with the same volume of normal saline. After 24 h of modeling, the mice were administered by gavage once every day. The sham operation group and the model group were administered with 0.5% CMC-Na via gavage, and the other administration groups were administered 0.5% CMC-Na suspension of the corresponding drug, and the administration lasted for 21 days. The mice should be strictly fasting with nothing but water 12 hours prior to surgery. After the last administration for 1 h, the whole blood from the eyeball of mice was collected, and use of cervical dislocation to euthanize the mice. Mice lung was collected, weighed and the pulmonary lesion was measured. The lung tissue fixation and paraffin section methods were the same as in Embodiment 5. Pathological sections were obtained after fixation. Sections were stained with hematoxylin-eosin stain (HE) and Masson' trichrome stain to observe the improvement of lung tissue inflammation and fibrosis levels, further selecting Hubner's histological scoring system to evaluate lung fibrosis: Score 0: no fibrotic burden, alveolar structure is normal; score 1: alveoli partly enlarged and rarefied, but no fibrosis masses was present; alveolar septa became thinner; isolated gentle fibrotic changes (septum≤3×thicker than normal); score 2: clearly fibrotic changes (septum>3×thicker than normal) with knot-like formation but not connected to each other; score 3: alveoli partly enlarged and rarefied, fibrotic masses, alveolar septa became thinner; contiguous fibrotic walls (septum>3×thicker than normal) predominantly in the whole microscopic field; score 4: single fibrotic masses (≤10% of microscopic field); score 5: confluent fibrotic masses (>10% and ≤50% of microscopic field), lung structure severely damaged but still preserved; score 6: large contiguous fibrotic masses (>50% of microscopic field), lung architecture mostly not preserved; alveolar septa, mostly not exist; score 7: alveoli nearly obliterated with fibrous masses; alveolar septa: nonexistent; score 8: fibrous masses were present through entire microscopic field of view.

3. Experimental Results

The results showed that the compounds of the disclosure at high-dose (120 mg/kg) and low-dose (40 mg/kg) significantly improve the silica-induced fibrosis levels of the pulmonary in KM mice. The mean pulmonary fibrosis score fell from 6.75 of the model group down to 1.5-2.7, which occurred in the groups treated with ADY, ADY-6 and ADY-8; the mean pulmonary fibrosis score fell to 2.2-2.7, which occurred in the groups treated with the low-dose of ADC-2 and ADC-12, as well as high-dose of ADC-15; the mean pulmonary fibrosis score fell from 5.5 of the model group down to 2.1-2.8, which occurred in the groups treated with ADY-4, ADY-7 and ADY-12; the mean pulmonary fibrosis score fell from 5.5 of the model group down to 2.1-1.9, which occurred in the groups treated with high-dose DAC-4 and low-dose ADC-10. The compounds of the disclosure had higher anti-pulmonary fibrosis effect than an equivalent dose of AD (score 3.8-4.9). The results of the improvement in the pulmonary fibrosis by partial representative compounds were shown in FIGS. 13A and 13B.

EXAMPLE 7

The compounds of the disclosure significantly improve the renal fibrosis induced by unilateral ureteral ligation in KM mice.

1. Experimental Animals

SPF grade KM mice, healthy, male, with a body weight of 20±2 g, were purchased from Henan Experimental Animal Center. (License No. SCXK (Yu) 2017-0001).

2. Experimental Methods

After KM mice were fed ad libitum for 3 days, they were randomly divided into six groups including a sham-operated control group, a model group, different groups of the compounds of the disclosure, seven mice per group. The preoperative preparation and anesthesia method were the same as in Embodiment 5. After the immobilization in a supine position, the mice were anesthetized. The hair from the lower edge of the sternum to the hind limbs was shaved, and then the surgery cloth was spread out and swabbed with iodine to sterilize the skin regions. An incision with a length of about 1 cm was made about 0.5 cm along the lower edge of the sternum. It was easy to extrude the kidney and then pull ureter upwards to separate from donor abdomen. Double-ligated with 5/0 silk thread and disconnected the ureter with a distance of about ⅓ of the ureter from the bladder. After the kidney was sent back to the abdomen, the 5/0 silk thread continuous suture method was used to close the abdomen layer by layer. The wound was swabbed with iodine and wrapped with sterile gauze. Then the rats rest in a 37° C. warm environment until the animals were fully awake. The sham-operated group only freed the ureter but did not ligature or segment. After 24 h of modeling, the mice were administered by gavage once every day. The administration method was the same as in Example 5, and the experiment was over after 7 days of administration. The mice should be strictly fasting with nothing but water 12 hours prior to surgery. After the last administration for 1 h, 3% barbital sodium (2 mL/kg) anesthetic were intraperitoneally injected to mice. Following the collection of blood, the left kidney was quickly and completely dissected. The kidney weight and kidney size were subsequently measured. The kidney of the mice was fixed in 4% paraformaldehyde fixative after photographing. The paraffin section method, serum preparation, HE staining and Masson staining, and statistical methods were the same as in Examples 5 and 6. Pathological sections were obtained after fixation. Sections were stained with hematoxylin-eosin (HE) or Masson' trichrome staining to observe the improvement of kidney tissue in inflammation and fibrosis, respectively. A pathological scoring system for renal interstitial fibrosis: score 1: basically normal interstitial, mild tubular degeneration; score 2: interstitial fibrosis, tubular atrophy <20%, scattered inflammatory cell infiltration; score 3: interstitial fibrosis, tubular atrophy accounted for 30%, scattered and/or diffused inflammatory cell infiltration; score 4; interstitial fibrosis, tubular atrophy >50%, scattered and/or diffused inflammatory cell infiltration.

3. Experimental Results

The results of FIGS. 14A, 14B, 15A, 15B, 16A and 16B showed that the sham operation group, the surface of the kidney tissue was moist and shiny, the structure of the glomerulus was intact, the renal tubules were tight and compact, and there was no visible lesion. In the model group, the kidney tissue became swollen, with a large amount of effusion in the middle and adhesion to the surrounding tissues. There was fibroproliferative tissue in the glomerulus and part of the necrosis. The renal interstitial fibrosis material was used to compress the renal tubules. The tubules were severely atrophied and a large number of inflammatory cells infiltrated in the renal interstitium. All intrinsic cells in some area of the renal tubules shed and form protein casts. Compared with the model group, the renal tissue damage of the animals in the compounds-administered groups was improved to some extent. The efficacy of disclosed compounds-administered group was significantly better than that of the AD treatment group, their pathological scores for renal interstitial fibrosis decreased from score 4 of the model group to score 1 or score 2.

It will be obvious to those skilled in the art that changes and modifications may be made, and therefore, the aim in the appended claims is to cover all such changes and modifications.

What is claimed is:

1. A compound represented by formula I or I':

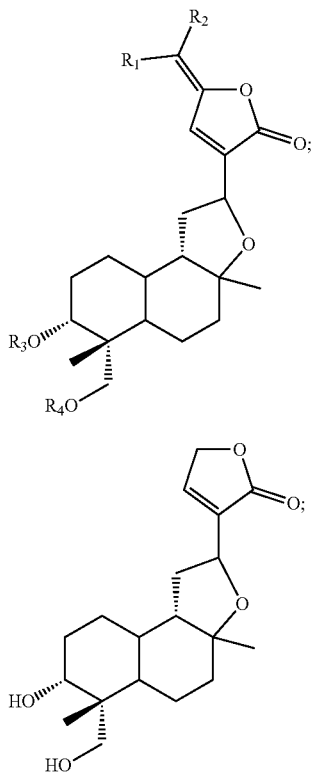

wherein:

$R_1$ and $R_2$ are at each occurrence selected from the group consisting of hydrogen, methyl, phenyl, 2-methoxyphenyl, 3-methoxyphenyl, 4-methoxyphenyl, 3,4,5-trimethoxyphenyl, 2-hydroxyphenyl, 3-hydroxyphenyl, 4-hydroxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromobenzene group, 3-fluoro-4-bromophenyl, 3-chloro-4-bromophenyl, 2,3,4-trichlorophenyl, 2-methoxy-4-chlorophenyl, 2-hydroxy-4-chlorophenyl, 2-hydroxy-4-methoxyphenyl, 3-fluoro-4-(4-methylpiperazinyl)phenyl, 4-(N,N-dimethylamino)phenyl, and 3-fluoro-4-(4-morpholinyl)phenyl; and $R_3$ and $R_4$ are hydrogen, or $R_3$ and $R_4$ are at each occurrence selected from the group consisting of —CH$_2$CH$_2$COOH, —CH$_2$CH$_2$CH$_2$CH$_2$COOH, —CH$_2$CH=CHCH$_2$COOH, and —CH$_2$CH$_2$CH$_2$CH$_2$CH$_2$CH$_2$CH$_2$COOH; or $R_3$ and $R_4$ are —COR$_5$, and $R_5$ is selected from the group consisting of 3-pyridyl, —CH$_2$CH$_2$COOH, —CH$_2$CH$_2$CH$_2$CH$_2$COOH, —CH$_2$CH=CHCH$_2$COOH, and —CH$_2$CH$_2$CH$_2$CH$_2$CH$_2$CH$_2$CH$_2$COOH.

2. The compound of claim 1, wherein:

$R_1$ and $R_2$ are at each occurrence selected from the group consisting of hydrogen, phenyl, 2-methoxyphenyl, 3-methoxyphenyl, 4-methoxyphenyl, 3,4,5-trimethoxyphenyl, 2-hydroxyphenyl, 3-hydroxyphenyl, 4-hydroxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorobenzene group, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromophenyl, 3-fluoro-4-bromophenyl, 3-chloro-4-bromophenyl, 2,3,4-trichlorophenyl, 2-methoxy-4-chlorophenyl, 2-hydroxy-4-chlorophenyl, 2-hydroxy-4-methoxyphenyl, 3-fluoro-4-(4-methylpiperazinyl)phenyl, 4-(N,N-dimethylamino)phenyl, and 3-fluoro-4-(4-morpholinyl)phenyl; and $R_1$ is different from $R_2$; and $R_3$ and $R_4$ are hydrogen; or $R_3$ and $R_4$ are at each occurrence selected from the group consisting of CH$_2$CH$_2$COOH, CH$_2$CH$_2$CH$_2$CH$_2$COOH, CH$_2$CH=CHCH$_2$COOH, and CH$_2$CH$_2$CH$_2$CH$_2$CH$_2$CH$_2$CH$_2$CH$_2$COOH; or $R_3$ and $R_4$ are COR$_5$, wherein $R_5$ is 3-pyridyl or CH$_2$CH$_2$COOH; and $R_3$ is the same as $R_4$.

3. The compound of claim 1, wherein:

one of $R_1$ and $R_2$ is hydrogen, and the other is selected from the group consisting of phenyl, 2-methoxyphenyl, 3-methoxyphenyl, 4-methoxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromophenyl, 3-fluoro-4-bromophenyl, 2-methoxy-4-chlorophenyl, 4-hydroxyphenyl, 3,4,5-trimethoxyphenyl, 3-fluoro-4-

(4-methylpiperazinyl)phenyl, 4-(N,N-dimethylamino) phenyl, and 3-fluoro-4-(4-morpholinyl)phenyl; and $R_3$ and $R_4$ are hydrogen; or $R_3$ and $R_4$ are at each occurrence selected from the group consisting of —$CH_2CH_2COOH$, —$CH_2CH_2CH_2CH_2COOH$, —$CH_2CH=CHCH_2COOH$, and —$CH_2CH_2CH_2CH_2CH_2CH_2CH_2COOH$; or $R_3$ and $R_4$ are —$COR_5$; where $R_5$ is selected from 3-pyridyl and —$CH_2CH_2COOH$; and $R_3$ is the same as $R_4$.

4. The compound of claim 1, being one of the following compounds:
ADY-1: $R_1$=H, $R_2$=4-Cl—$C_6H_4$, $R_3$=$R_4$=H;
ADY-2: $R_1$=H, $R_2$=4-Br—$C_6H_4$, $R_3$=$R_4$=H;
ADY-3: $R_1$=H, $R_2$=4-F—$C_6H_4$, $R_3$=$R_4$=H;
ADY-4: $R_1$=H, $R_2$=2-Cl—$C_6H_4$, $R_3$=$R_4$=H;
ADY-5: $R_1$=H, $R_2$=$C_6H_5$, $R_3$=$R_4$=H;
ADY-6: $R_1$=H, $R_2$=3,4-difluorophenyl, $R_3$=$R_4$=H;
ADY-7: $R_1$=H, $R_2$=3-$CH_3$O—$C_6H_4$, $R_3$=$R_4$=H;
ADY-8: $R_1$=H, $R_2$=4-OH—$C_6H_4$, $R_3$=$R_4$=H;
ADY-9: $R_1$=H, $R_2$=3,4,5-trimethoxyphenyl, $R_3$=$R_4$=H;
ADY-10: $R_1$=H, $R_2$=3-Cl—$C_6H_4$, $R_3$=$R_4$=H;
ADY-11: $R_1$=H, $R_2$=3-F-4-(N-methylpiperidine)-$C_6H_3$, $R_3$=$R_4$=H;
ADY-12: $R_1$=H, $R_2$=4-$CH_3$O—$C_6H_4$, $R_3$=$R_4$=H;
ADY-13: $R_1$=H, $R_2$=3-F-4-morpholine-$C_6H_3$, $R_3$=$R_4$=H;
ADY-14: $R_1$=H, $R_2$=4-(N—$(CH_3)_2$)—$C_6H_4$, $R_3$=$R_4$=H;
ADY-15: $R_1$=H, $R_2$=3,4-difluorophenyl, $R_3$=$R_4$=$COR_5$, $R_5$=3-pyridyl;
ADY-16: $R_1$=H, $R_2$=$C_6H_5$, $R_3$=$R_4$=$COR_5$, $R_5$=3-pyridyl; and
ADY-17: $R_1$=H, $R_2$=4-Cl—$C_6H_4$, $R_3$=$R_4$=$COR_5$, $R_5$=$CH_2CH_2COOH$.

5. A compound represented by formula II or II':

wherein:
$R_1$ and $R_2$ are at each occurrence selected from the group consisting of hydrogen, phenyl, methyl, 2-furyl, 2-methoxyphenyl, 3-methoxyphenyl, 4-methoxyphenyl, 3,4,5-trimethoxyphenyl, 2-hydroxyphenyl, 3-hydroxyphenyl, 4-hydroxyphenyl, 2-nitrophenyl, 3-nitrophenyl, 4-nitrophenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromobenzene group, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromophenyl, 3-fluoro-4-bromophenyl, 3-chloro-4-bromophenyl, 2,3,4-trichlorophenyl, 2-methoxy-4-chlorophenyl, 2-hydroxy-4-chlorophenyl, 2-hydroxy-4-methoxyphenyl, 3-amino-4-chlorophenyl, 2-amino-4-chlorophenyl, 4-(N,N-dimethylamino)phenyl, 3-fluoro-4-(4-morpholinyl)phenyl, and 3-fluoro-4-(4-methylpiperazinyl)phenyl; or $R_1$ is connected to $R_2$ to form a cyclohexyl or cyclopentyl.

6. The compound of claim 5, wherein one of $R_1$ and $R_2$ is hydrogen, and the other is selected from the group consisting of methyl, 2-furyl, phenyl, 2-methoxyphenyl, 3-methoxyphenyl, 4-methoxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 3,4,5-trimethoxybenzene group, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromophenyl, 3-fluoro-4-bromophenyl, 3-chloro-4-bromophenyl, 2-methoxy-4-chlorophenyl, 4-(N,N-dimethylamino)phenyl, 3-fluoro-4-(4-morpholinyl)phenyl, 3-fluoro-4-(4-methylpiperazinyl)phenyl, 2-hydroxyphenyl, 3-hydroxyphenyl, 4-hydroxyphenyl, 2-nitrophenyl, 3-nitrophenyl, and 4-nitrophenyl; or $R_1$ is connected to $R_2$ to form a cyclohexyl.

7. The compound of claim 5, being one of the following compounds:
ADC-1: $R_1$=H, $R_2$=4-Cl—$C_6H_4$;
ADC-2: $R_1$=H, $R_2$=$C_6H_5$;
ADC-3: $R_1$=H, $R_2$=3-Cl—$C_6H_4$;
ADC-4: $R_1$=H, $R_2$=4-Br—$C_6H_4$;
ADC-5: $R_1$=H, $R_2$=4-F—$C_6H_4$;
ADC-6: $R_1$=H, $R_2$=3,4-difluorophenyl;
ADC-7: $R_1$=H, $R_2$=2-Cl—$C_6H_4$;
ADC-8: $R_1$=H, $R_2$=3-$CH_3$O—$C_6H_4$;
ADC-9: $R_1$=H, $R_2$=4-$N(CH_3)_2$—$C_6H_4$;
ADC-10: $R_1$=H, $R_2$=3-F-4-(4-morpholinyl)-$C_6H_3$;
ADC-11: $R_1$=H, $R_2$=4-$CH_3$O—$C_6H_4$;
ADC-12: $R_1$=H, $R_2$=2-HO—$C_6H_4$;
ADC-13: $R_1$=H, $R_2$=4-HO—$C_6H_4$;
ADC-14: $R_1$=H, $R_2$=3-$NO_2$—$C_6H_4$;
ADC-15: $R_1$=H, $R_2$=3,4,5-trimethoxyphenyl;
ADC-16: $R_1$=H, $R_2$=2-furyl; and
ADC-17: $R_1$ is connected toltzto form a cyclohexyl.

8. A method for treatment or slowing progression of a fibrotic disease, the method comprising administering to a patient in need thereof the compound of claim 1.

9. The method of claim 8, wherein the fibrotic disease is liver fibrosis, pulmonary fibrosis, renal fibrosis, or myocardial fibrosis.

10. A method for treatment of a fibrotic disease comprising administering to a patient in need thereof the compound of claim 5.

11. The method of claim 10, wherein the fibrotic disease is liver fibrosis, pulmonary fibrosis, renal fibrosis, or myocardial fibrosis.

12. The method of claim 10, further comprising mixing the compound and a pharmaceutically acceptable excipient to yield an oral preparation or parenteral formulation prior to being administered to the patient.

13. The method of claim 12, wherein the oral preparation is a tablet, a pill, a capsule, a granule or syrup; or the parenteral formulation is a solution injection or lyophilized powder injection.

* * * * *